(12) United States Patent
Piehowski et al.

(10) Patent No.: US 11,719,702 B2
(45) Date of Patent: Aug. 8, 2023

(54) METHODS AND SYSTEMS OF PROTEOME ANALYSIS AND IMAGING

(71) Applicant: BATTELLE MEMORIAL INSTITUTE, Richland, WA (US)

(72) Inventors: Paul D. Piehowski, West Richland, WA (US); Ying Zhu, Richland, WA (US); Ryan T. Kelly, West Richland, WA (US); Kristin E. Burnum-Johnson, Richland, WA (US); Ronald J. Moore, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/993,949

(22) Filed: May 31, 2018

(65) Prior Publication Data

US 2018/0299463 A1   Oct. 18, 2018

Related U.S. Application Data

(63) Continuation-in-part of application No. 15/897,022, filed on Feb. 14, 2018, which is a continuation-in-part
(Continued)

(51) Int. Cl.
*G01N 33/68* (2006.01)
*G16B 45/00* (2019.01)

(52) U.S. Cl.
CPC ..... *G01N 33/6842* (2013.01); *G01N 33/6848* (2013.01); *G16B 45/00* (2019.02); *G01N 2333/4716* (2013.01); *G01N 2570/00* (2013.01)

(58) Field of Classification Search
None
See application file for complete search history.

(56) References Cited

U.S. PATENT DOCUMENTS

| 6,565,813 B1 * | 5/2003 | Garyantes | B01F 33/3021 |
| | | | 422/553 |
| 2006/0154230 A1 * | 7/2006 | Cunanan | A01N 1/0226 |
| | | | 435/1.1 |

(Continued)

FOREIGN PATENT DOCUMENTS

| DE | 10 2004 041941 | 3/2006 | |
| EP | 0 290 125 | * 3/1988 | ............... G02B 1/10 |

(Continued)

OTHER PUBLICATIONS

Chang, Y-H, et al. New Mass-Spectrometry-Compatible Degradable Surfactant for Tissue Proteomics, Journal of Proteome Research, vol. 14, pp. 1587-1599 (Year: 2015).*

(Continued)

*Primary Examiner* — Xiaoyun R Xu
(74) *Attorney, Agent, or Firm* — Klarquist Sparkman, LLP

(57) ABSTRACT

Provided herein are methods and systems for proteome analysis that are at least partially automated and/or performed robotically. In some aspects, the methods and systems described herein can rapidly and efficiently provide protein identification of each of the proteins from a proteome, or a complement of proteins, obtained from extremely small amounts of biological samples. The identified proteins can be imaged quantitatively over a spatial region. Automation and robotics facilitates the throughput of the methods and systems, which enables protein imaging and/or rapid proteome analysis.

39 Claims, 53 Drawing Sheets

Related U.S. Application Data of application No. PCT/US2017/060399, filed on Nov. 7, 2017.

(60) Provisional application No. 62/418,544, filed on Nov. 7, 2016.

(56) References Cited

U.S. PATENT DOCUMENTS

| | | | |
|---|---|---|---|
| 2007/0004044 A1* | 1/2007 | Ramsay | G01N 33/5005 436/86 |
| 2010/0261159 A1 | 10/2010 | Hess et al. | |
| 2011/0272405 A1* | 11/2011 | Thurman | B65D 47/0838 220/260 |
| 2013/0109024 A1 | 5/2013 | Rajagopalan et al. | |
| 2014/0235468 A1 | 8/2014 | Cheng et al. | |

FOREIGN PATENT DOCUMENTS

| | | |
|---|---|---|
| WO | 2013010134 A2 | 1/2013 |
| WO | 2013138767 A1 | 9/2013 |
| WO | WO 2017/144886 | 8/2017 |
| WO | WO 2017/205687 | 11/2017 |
| WO | WO 2018/085835 | 5/2018 |

OTHER PUBLICATIONS

Seeley, E.H. et al. Molecular imaging of proteins in tissues by mass spectrometry, PNAS, vol. 105(47), pp. 18126-18131 (Year: 2008).*
Kowalski et al. Mitigating Matrix Effects: Examination of Dilution, QuEChERS, and Calibration Strategies for LC-MS/MS Analysis of Pesticide Residues in Diverse Food Types, Restek Corporation. (Year: 2014).*
Dixon, R.B. Sample Preparation—A Practical Approach for Robust Analyses, AACC's fifth annual Mass Spectrometry Conference, Oct. 1-2, 2015, Chicago. (Year: 2015) retrieved from internet site:https://www.aacc.org/~/media/files/meetings-andevents/resources-from-past-events/conferences/2015/oct1/dixon_slides_day1.pdf?la=en.*
Morrogh, M. et al. Tissue preparation for laser capture microdissection and RNA extraction from fresh frozen breast tissue, BioTechniques 43:41-48 (Year: 2007).*
Achim, K., et al., High-through-put spatial mapping of single-cell RNA-seq data to tissue of origin, Nature Biotechnology, 33, 5, 2014, 503-509.
Bendall, S. C., et al., Single-Cell Mass Cytometry of Differential Immune and Drug Responses Across a Human Hematopoietic Continuum, Science, 332, 2011, 687-696.
Chen, Q., et al., Ultrasensitive Proteome Profiling for 100 Living Cells by Direct Cell Injection, Online Digestion and Nano-LC-MS/MS Analysis, Analytical Chemistry, 87, 2015, 6674-6680.
Chen, W., et al., Simple and Integrated Spintip-Based Technology Applied for Deep Proteome Profiling, Analytical Chemistry, 88, 2016, 4864-4871.
Clair, G., et al., Spatially-Resolved Proteomics: Rapid Quantitative Analysis of Laser Caputre Microdissected Alveolar Tissue Samples, Scientific Reports, 6, 2016, 39223.
Goebel-Stengel, M., et al., The importance of using the optimal plasticware and glassware in studies involving peptides, Analytical Biochemistry, 414, 2011, 38-46.
Huang, E. L., et al., SNaPP: Simplified Nanoproteomics Platform for Reproducible Global Proteomic Analysis of Nanogram Protein Quantities, Endocrinology, 157, 2016, 1307-1317.
Jatain, D. A., et al., Massively Parallel Single-Cell RNA-Seq for Marker-Free Decomposition of Tissues into Cell Types, Science, 343, 2016, 776-779.
Kelly, R. T., et al., The Ion Funnel: Theory, Implementations, and Applications, Mass Spectometry Reviews, 29, 2010, 294-312.

Li, S., et al., An Integrated Platfor for Isolation, Processing, and Mass Spectrometry-based Proteomic Profiling of Rare Cells in Whole Blood, Mol Cell Proteomics, 14, 2015, 1672-1683.
Lombard-Banek, C., et al., Single-Cell Mass Spectrometry for Discovery Proteomics: Quantifying Translational Cell Heterogeneity in the 16-Cell Frog (Xenopus) Embryo, Agnew Chem Int Ed, 55, 2106, 2454-2458.
Pisania, A., et al., Quantitative analysis of cell composition and purity of human pancreatic islet preparations, Lab Investig, 90, 2010, 1661-1675.
Richardson, S. J., et al., Islet cell hyperexpression of HLA class I antigens: a defining feature in type 1 diabetes, Diabetologia, 59, 2016, 2448-2458.
Rodriguez-Calvo, T., et al., Heterogeneity and Lobularity of Pancreatic Pathology in Type I Diabetes during the Prediabetic Phase, Journal of Histochemistry & Cytochemistry, 63, 2015, 626-636.
Rowe, P. A., et al., The pancrease in human type diabetes, Semin Immunopathol, 33, 2011, 29-43.
Shapiro, E., et al., Single-cell sequencing-based technologies will revolutionize whole-organism science, Nature Reviews Genetics, 14, 2013, 618-630.
Schneider, C. A., et al., NIH Image to ImageJ: 25 years of image analysis, Nature Methods, 9, 7, 2012, 671-675.
Shen, Y., et al., High-Efficiency On-Line Solid-Phase Extraction Coupling to 15-150 μm-i.d. Column Liquid Chromatography for Proteomic Analysis, Analytical Chemistry, 75, 14, 2003, 3596-3605.
Shen, Y., et al., Ultrasensitive Proteomics Using High-Efficiency On-Line Micro-SPE-NanoLC-NanoESI MS and MS/MS, Analytical Chemistry, 76, 2004, 144-154.
Smith, R. D., et al., Ultrasensitive and Quantitative Analyses from Combined Separations—Mass Spectrometry for the Characterization of Preteomes, Acc Chem Res, 37, 2004, 269-278.
Spitzer, M., et al, BoxPltsR: a web tool for generation of box plots, Nature Methods, 11, 2, 2014, 121-122.
Sun, L., et al., Ultrasensitive and Fast Bottom-up Analysis of Femtogram Amounts of Complex Proteome Digests, Agnew Chem Int Ed, 52, 2013, 13661-13664.
Sun, L., et al., Single Cell Using Frog (Xenopus laevis) Blastomeres Isolated from Early Stage Embryos, Which Form a Geometric Progression in Protein Content, Analytical Chemistry, 88, 2016, 6653-6657.
Sun, X., et al., Ultrasensitive nanoelectrospray ionization-mass spectrometry using poly(dimethylsiloxane) microchips with monolithically intregrated emitters, Analyst, 135, 2010, 2296-2302.
Tyanova, S., et al., The Perseus computational platform for comprehensive analysis of (prote)omics data, Nature Methods, 13, 9, 2016, 731-740.
Tyanova, S., et al., The MaxQuant computational platform for mass spectrometry-based shotgun proteomics, Nature Protocols, 11, 12, 2016, 2301-2319.
Vandermarliere, E., et al., Getting Intimate with Trypsin, the Leading Protease in Proteomics, Mass Spectrometry Reviews, 32, 2013, 453-465.
Volpe, P., et al., Quantitative Studies on Cell Proteins in Suspension Cultures, Eur J Biochem, 1970, 195-200.
Waanders, L. F., et al., Quantitative proteomic analysis of single pancreatic islets, PNAS, 106, 2009, 18902-18907.
Wang, H., et al., Development and Evaluation of a Micro- and Nanoscale Proteomic Sample Preparation Method, Journal of Proteome Research, 4, 2005, 2397-2403.
Wang, N., et al., Development of Mass Spectrometry-Based Shotgun Method for Proteome Analysis of 500 to 5000 Cancer Cells, Anal Chem, 82, 2010, 2262-2271.
White, A. K., et al., High-throughput microfluidic single-cell RT-qPCR, PNAS, 108, 34, 13999-14004.
Wisniewski, J. R., et al., High Recovery FASP Applied to the Proteomic Analysis of Microdissected Formalin Fixed Paraffin Embedded Cancer Tissues Retrieves Known Colon Cancer Markers, Journal of Proteome Research, 10, 2011, 3040-3049.
Wisniewski, J. R., A "Proteomic Ruler" for Protein Copy Number and Concentration Estimation without Spike-in Standards, Molecular & Cellular Proteomics, 13, 2014, 3497-3506.
Yu, Y-Q., et al., Enzyme-Friendly, Mass Spectrometry-Compatible Surfactant for In-Solution Enzymatic Digestion of Proteins, Anal Chem, 75, 2003, 6023-6028.

(56) References Cited

OTHER PUBLICATIONS

Zeiler, M., et al., A Protein Epitope Signature Tag (PrEST) Library Allows SILAC-based Absolute Quantification and Multiplexed Determination of Protein Copy Numbers in Cell Lines, Molecular & Cellular Proteomics, 11, 2012, O111.009613.

Zhu, Y., et al., Integrated Droplet Analysis System with Electrospray Ionization-Mass Spectrometry Using a Hydrophilic Tongue-Based Droplet Extraction Interface, Analytical Chemistry, 82, 19, 2010, 8361-8366.

Zhu, Y., et al., Sequential Operation Droplet Array: An Automated Microfluidic Platform for Picoliter-Scale Liquid Handling, Analysis, and Screening, Analytical Chemistry, 85, 2013, 6723-6731.

Zhu, Y., et al., Nanoliter-Scale Protein Crystallization and Screening with a Microfluidic Droplet Robot, Scientific Reports, 4, 2014, 5046.

Zhu, Y., et al, Printing 2-Dimentional Droplet Array for Single-Cell Reverse Transcription Quantitative PCR Assay with a Microfluidic Robot, Scientific Reports, 5, 2015, 9551.

International Search Report and Written Opinion issued for International Application No. PCT/US2017/060399 dated Jan. 11, 2018.

Chen, X., et al., High-Precision Dispensing of Nanoliter Biofluids on Glass Pedestal Arrays for Ultrasensitive Biomolecule Detection, Applied Materials & Interfaces, 8, 2016, 10788-10799.

Deng, L., et al., Ultra-High Resolution Ion Mobility Separations Utilizing Traveling Waves in a 13 m Serpentine Path Length Structures for Lossless Ion Manipulations Module, Analytical Chemistry, 88, 2016, 8957-8964.

Kelly, R. T., et al., Nanowell Sample Processing Combined with Ultrasensitive LC-MS Towards Single Cell Proteomics, SciX Conference presentation, Sep. 22, 2016.

Kilimnik, G. et al., Quantification of Islet Size and Architecture, iSLETS, 4(2), 2012, 167-172.

Li, Q., et al., Automatic Combination of Microfluidic Nanoliter-Scale Droplet Array with High-Speed Capillary Electrophoresis, Scientific Reports, 6(1), 2016, 1-9.

Rauniyar, N., et al., Isobaric Labeling-Based Relative Quantification in Shotgun Proteomics, Journal of Proteome Research, 13(12), 2014, 5293-5309.

Zhang, L., et al., Proteomic profiling of human islets collected from frozen pancreata using layer capture microdissection, Journal of Proteomics, 150(6), 2017, 149-159.

Zhu, Y., et al., Printing 2-Dimentional Droplet Array for Single-Cell Reverse Transcription Quantitative PCR Assay with a Microfluidic Robot, Scientific Reports, 5, 2015, 1-7.

U.S. Appl. No. 15/897,022, filed Feb. 14, 2018.

Zhu et al., "Nanodroplet processing platform for deep and quantitative proteome profiling of 10-100 mammalian cells," *Nature Communications*, vol. 9, pp. 882-891, Feb. 28, 2018.

International Search Report and Written Opinion issued for International Application No. PCT/US2019/017009 dated Sep. 18, 2019.

International Search Report and Written Opinion issued for International Application No. PCT/US2019/034677 dated Aug. 22, 2019.

Non-Final Office Action issued in U.S. Appl. No. 15/897,022, dated Jul. 28, 2020, 20 pages.

\* cited by examiner

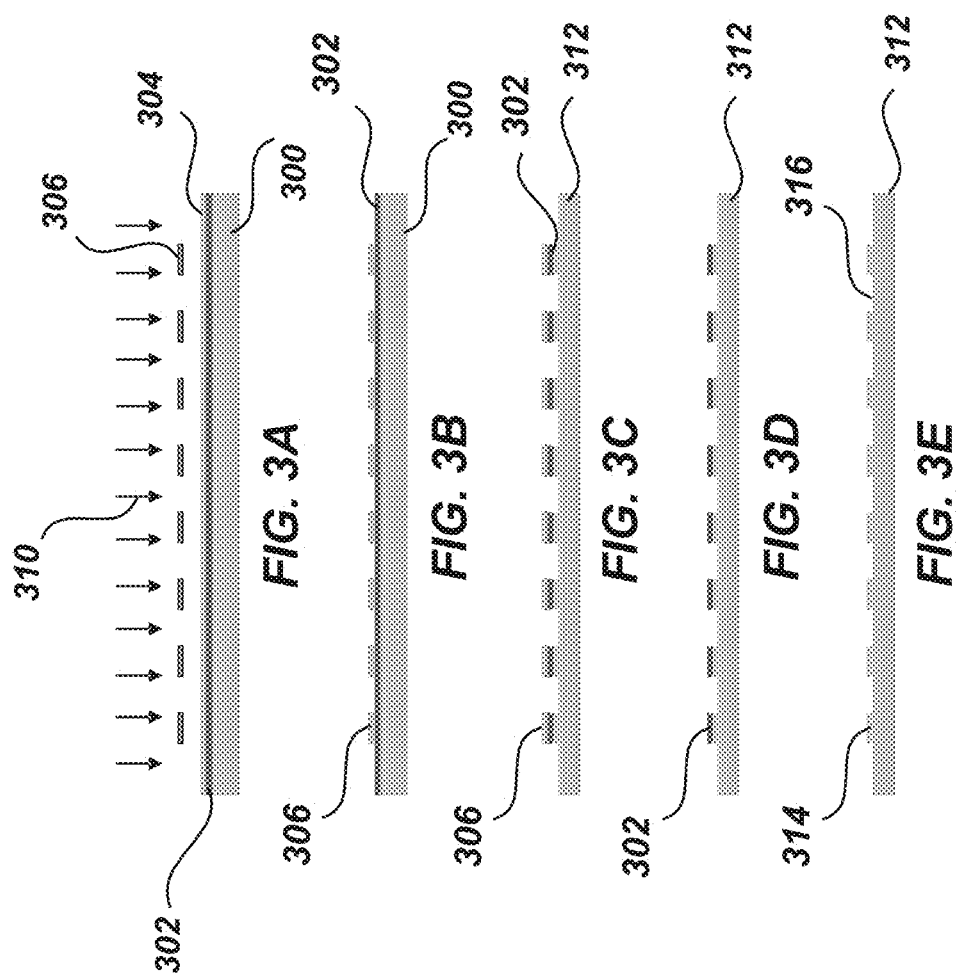

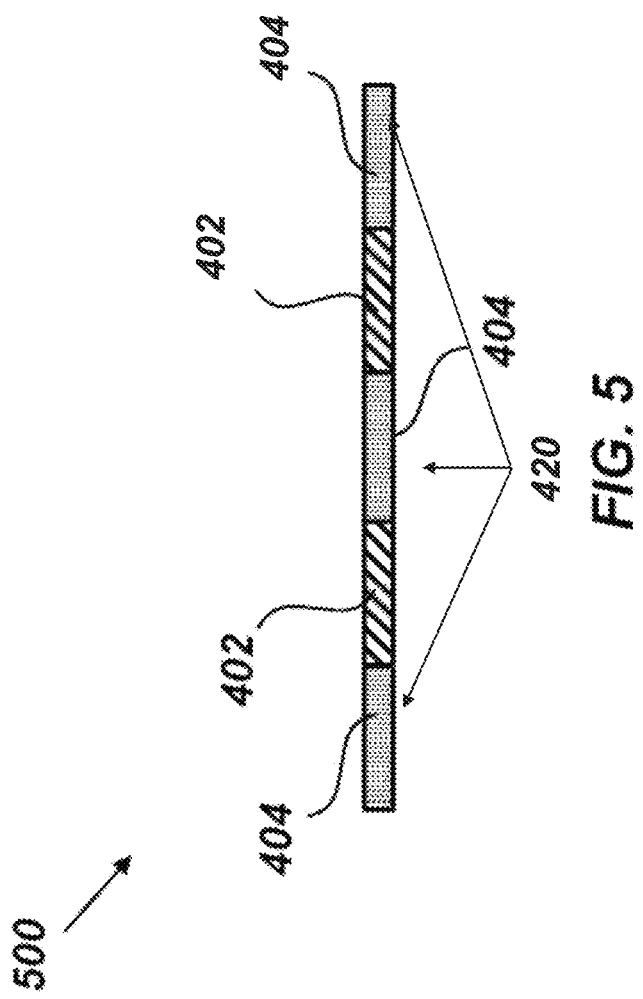

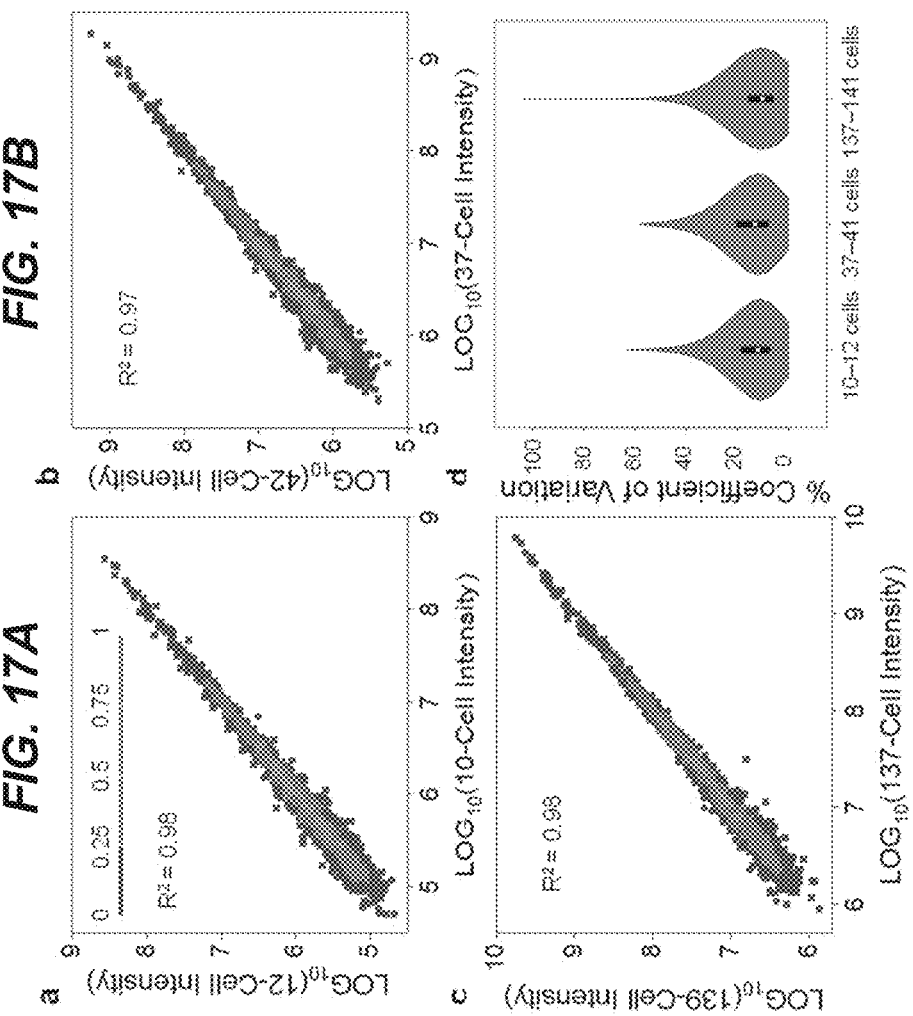

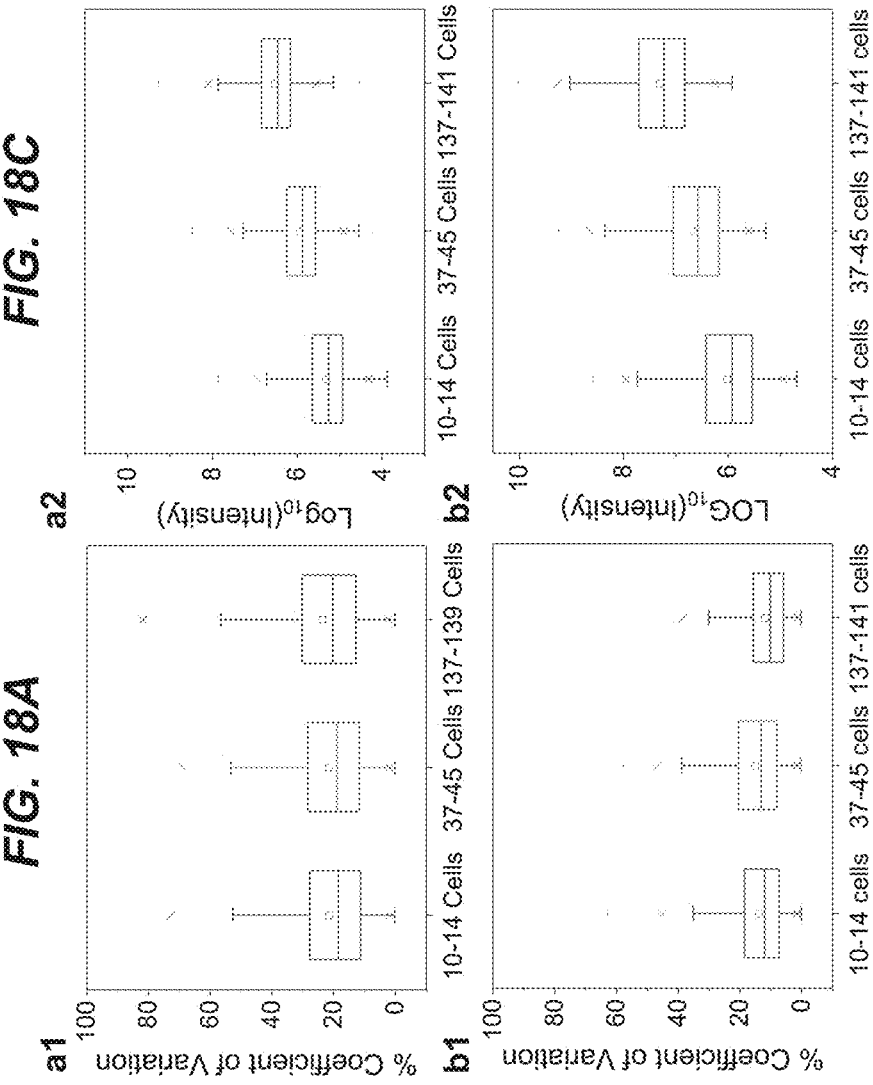

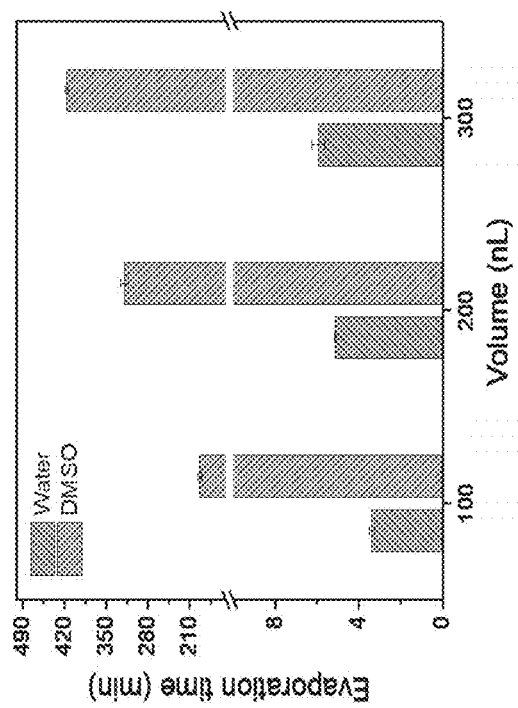
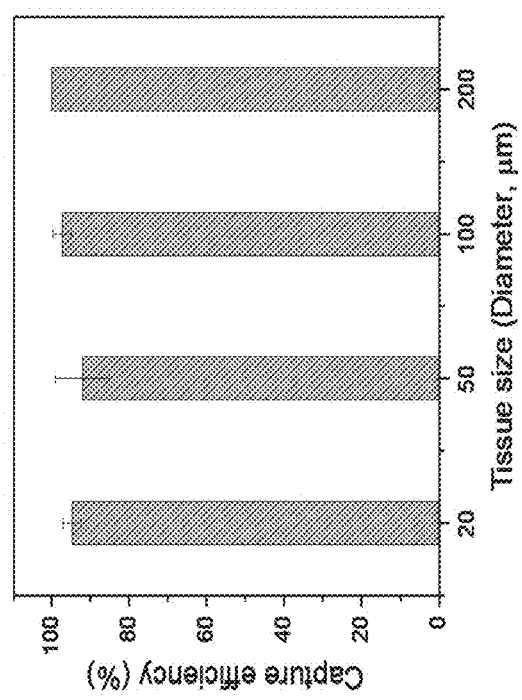
FIG. 30A
FIG. 30B

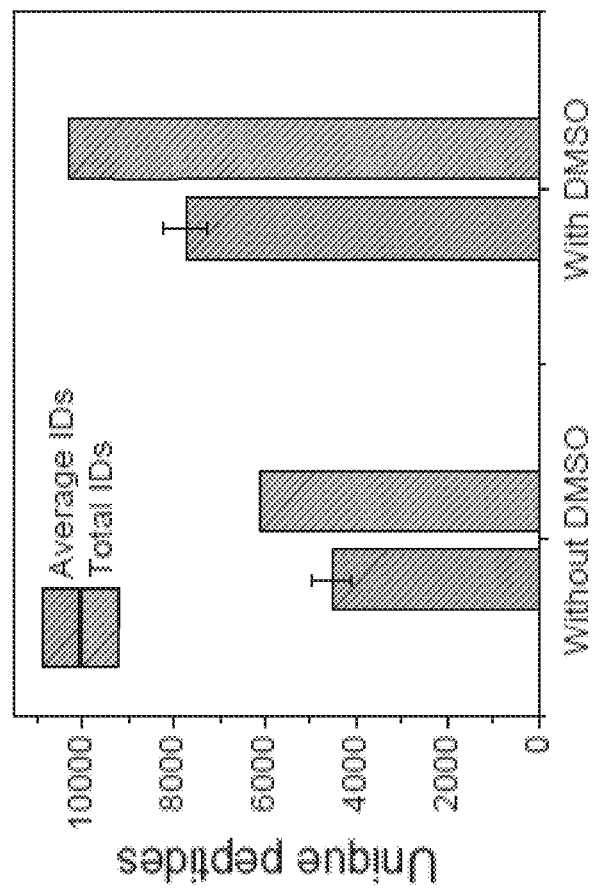

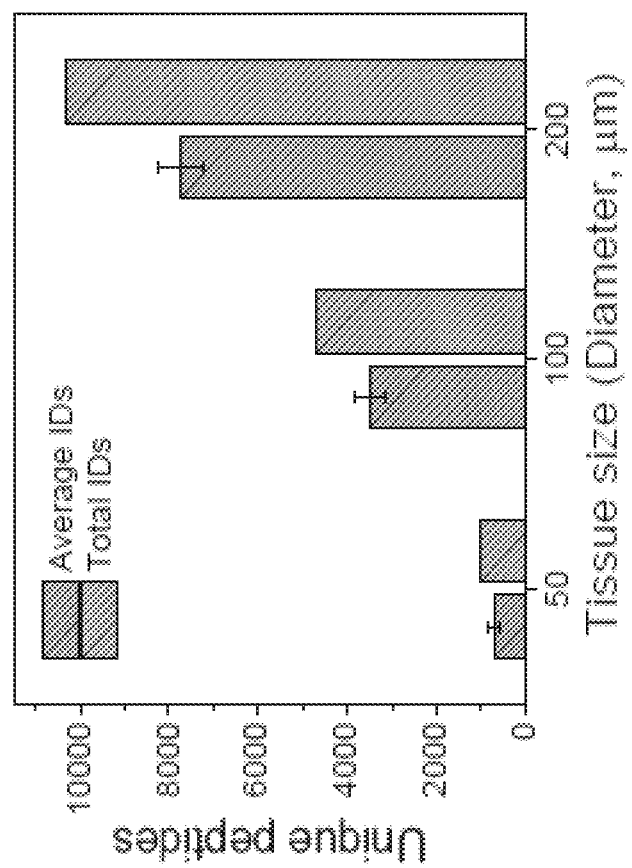

METHODS AND SYSTEMS OF PROTEOME ANALYSIS AND IMAGING

CROSS-REFERENCE TO RELATED APPLICATIONS

This application is a continuation-in-part of U.S. application Ser. No. 15/897,022, filed Feb. 14, 2018, which is a continuation-in-part of International Application No. PCT/US2017/060399, filed Nov. 7, 2017, which claims the benefit of priority to U.S. Provisional Application No. 62/418,544, filed Nov. 7, 2016, all of which are hereby incorporated in their entirety.

STATEMENT UNDER FEDERALLY SPONSORED RESEARCH AND DEVELOPMENT

This invention was made with Government support under grant nos. R21EB020976, P41GM103493, R33CA225248, and R21HD084788 awarded by the National Institutes of Health and under contract number DE-AC05-76RL01830 awarded by the Department of Energy. The government has certain rights in the invention.

FIELD

Embodiments of the disclosure relate generally to systems and methods for proteome analysis and particularly to proteome high-throughput analysis and/or imaging.

BACKGROUND

Human tissues are often highly heterogeneous, consisting of intermixed cellular populations and morphological substructures. Mass spectrometry (MS)-based proteomic analyses can require samples comprising thousands to millions of cells to provide an in-depth profile of protein expression, which can severely limit the ability to analyze small samples and resolve microheterogeneity within tissues. While MS sensitivity has steadily improved, the inability to effectively prepare and deliver such trace samples to the analytical platform has proven limiting.

Furthermore, there is an absence of effective analytical tools for performing high-throughput proteome analysis and/or probing the spatial distribution of the proteome without the use of labels and/or antibodies. The use of labels and/or antibodies requires a priori knowledge of the protein targets, long/expensive lead times, and introduction of undesirable artefacts. While mass spectrometry imaging (MSI) has emerged as a powerful tool for mapping the spatial distribution of metabolites and lipids across tissue surfaces, significant technical hurdles have limited the effective application of MSI techniques to the analysis of proteomes.

As the primary product of the genome, proteome information is critical to elucidating the processes being carried out in complex biological assemblies. Accordingly, there is a need for systems and methods of at least partially automated and/or robotic proteome analysis, particularly for those that can provide proteome imaging.

SUMMARY

Provided herein, inter alia, are compositions and methods for processing and analysis of small cell populations and biological samples (e.g., a robotically controlled chip-based nanodroplet platform). In particular aspects, the methods described herein can reduce total processing volumes from conventional volumes to nanoliter volumes within a single reactor vessel (e.g., within a single droplet reactor) while minimizing losses, such as due to sample evaporation.

Embodiments described herein can provide advantages over existing methods, which can require samples including a minimum of thousands of cells to provide in-depth proteome profiling. As described herein, embodiments of the disclosure can dramatically enhance the efficiency and recovery of sample processing through downscaling total processing volumes to the nanoliter range, while substantially avoiding sample loss.

Described herein are methods for preparing a biological sample, comprising obtaining a biological sample, and providing a platform. In embodiments, the platform may include at least one reactor vessel having one or more hydrophilic surfaces configured for containment of the biological sample, wherein the hydrophilic surfaces have a non-zero, total surface area less than 25 $mm^2$. In other embodiments, the hydrophilic surfaces of the at least one reactor vessel have a total surface area of less than 1 $mm^2$.

In further embodiments, the method includes transferring a first volume (e.g., a non-zero amount less than 1000 nL) of the biological sample to a single reactor vessel. In further embodiments, the methods include processing the biological sample in the single reactor vessel to yield a processed sample, and collecting a second volume of the processed sample (e.g., the second volume is a fraction of the first volume ranging from about 10 to about 100%).

In aspects, the biological sample can include at least one of tissues, biopsies, cell homogenates, cell fractions, cultured cells, non-cultured cells, whole blood, plasma, and biological fluids. In embodiments, the biological sample is less than 1000 nL. In other embodiments, the biological sample is less than 100 nL.

In various aspects, the methods of obtaining the biological sample may include, for example, dispensing cellular material from suspension and fluorescence-activated cell sorting.

In further aspects, the method may further comprise at least two reactor vessels, wherein the at least two reactor vessels are separated by a hydrophobic surface.

In embodiments, the biological sample for the methods described herein may include a non-zero amount of cells less than 5000 cells, less than 100 cells or less than 10 cells.

In other embodiments, the methods described herein further include analyzing the collected second volume (e.g., the second volume is a fraction of the first volume ranging from about 10 to about 100%) of the processed biological sample, and the analyzing step is configured to identify at least one unique species within the processed biological sample. In other embodiments, the analyzing step identifies at least 1,000 unique species, at least 3,000 unique species, or at least 5,000 unique species. In various embodiments, analyzing can identify greater than 3,000 unique species from 10 or less cells.

In embodiments, the unique species may include at least one of proteins or fragments thereof, lipids, or metabolites.

In other embodiments, the methods described herein further include analyzing the collected second volume, and wherein the analyzing step comprises mass spectrometry or flow cytometry.

In aspects, the platform of the methods described herein includes a glass chip. In other aspects, the glass chip is pre-coated, e.g., with chromium, aluminum, or gold. In other aspects, the glass chip includes a substrate containing the at least one reactor vessel, a spacer containing an aperture positioned on the substrate, and a cover positioned on the spacer, wherein the aperture is dimensioned to surround the at least one reactor vessel when the spacer is positioned on the substrate. In other aspects, the steps involving dispensing and aspiration of sample and processing reagents are performed in a humidity-controlled chamber (e.g., which is maintained from about 80% to about 95%.

In further embodiments, the methods described herein include processing the biological sample. Processing the biological sample may include at least one of cell lysis, analyte extraction and solubilization, denaturation, reduction, alkylation, chemical and enzymatic reactions, concentration, and incubation.

In aspects, the methods described herein include collecting the processed sample into a capillary. In other aspects, collecting the processed sample into a capillary includes aspirating the processed sample into the capillary and washing the single reactor vessel with a solvent. Additionally, the capillary may be sealed from the external environment after the processed sample is collected therein.

In alternative embodiments, the methods described herein include biological samples comprising of tissues. The tissue can include laser-capture microdissected tissues, e.g., having dimensions less than about 1 mm.

In embodiments, provided herein is a platform for biological sample preparation, including a substrate with at least one reactor vessel having one or more hydrophilic surfaces configured for containment of a biological sample. In embodiments, the hydrophilic surfaces have a non-zero total surface area less than 25 mm$^2$ or less than 5 mm$^2$. In further embodiments, the platform includes a spacer containing an aperture, wherein the aperture is dimensioned to surround the at least one reactor vessel when the spacer is positioned on the substrate; and a cover positioned on the spacer.

In embodiments, the platform further includes a membrane interposed between the spacer and the cover, the membrane configured to form a gas-tight seal between the spacer and the cover to minimize evaporation. The platform may be formed from a material that is substantially optically transparent (e.g., glass). In further embodiments, the platform may include at least one hydrophobic surface surrounding the at least one reactor vessel.

The platform described herein may further include at least two reactor vessels, wherein the at least two reactor vessels are separated by a hydrophobic surface. Alternatively, the hydrophilic surface is formed on an upper surface of the pillar and defines the lateral boundary of the least one reactor vessel. Additionally, the at least one reactor vessel is a well having a depth extending below a plane of the substrate that is defined by one or more sidewalls and a base, wherein one or more hydrophilic surfaces are formed on the base. The platform described herein may include that the at least one reactor vessel is a hydrophilic surface positioned on the plane of the substrate and a hydrophobic surface positioned on the plane of the substrate that surrounds the hydrophilic surface.

Also provided herein, inter alia, are methods and systems for proteome analysis that are at least partially automated and/or performed robotically. In particular aspects, the methods and systems described herein can rapidly and efficiently provide protein identification of each of the proteins from a proteome or a complement of proteins obtained from extremely small amounts of biological samples. In some embodiments, the identified proteins can be imaged quantitatively over a spatial region. Automation and robotics facilitates the throughput of the methods and systems, which enables proteome analysis and imaging. However, the small sample size poses a challenge to automation that is overcome by the embodiments described herein. In one example, dilution of a processed sample with buffer yields a diluted sample having sufficient volume to be handled by a MS-based analytical instrument autosampler. Unexpectedly, the dilution of the processed sample still yields sufficient signal-to-noise ratio for analysis.

In some embodiments, a method of proteome analysis comprises the steps of extracting from one NanoPOTS reactor vessel, a processed sample comprising less than 500 ng of a complement of proteins, peptides related to the complement of proteins, or both in a liquid buffer solution. The NanoPOTS reactor vessel can be one of a plurality of vessels on a NanoPOTS plate. The method can further comprise dispensing the processed sample into one well on a well plate having a plurality of wells, wherein the one well is pre-loaded with a volume of a liquid carrier buffer. In certain embodiments, the volume of the liquid carrier buffer is a non-zero amount that is less than 50 µL, 35 µL, 25 µL, or 15 µL. The processed sample can be diluted, thereby yielding in the one well a diluted sample. The diluted sample is then transferred from the one well to a mass-spectrometry-based (MS-based) analytical instrument. Examples of MS-based analytical instruments can include, but are not limited to, electrospray ionization-MS (ESI-MS), liquid chromatography-electrospray ionization-MS (LC-ESI-MS), capillary electrophoresis-electrospray ionization-MS (CE-ESI-MS), electrospray ionization-ion mobility spectrometry-MS (ESI-IMS-MS), and solid-phase extraction-ESI-MS (SPE-ESI-MS).

In certain embodiments, the complement of proteins comprises at least 1000 proteins. Alternatively, the complement of proteins can comprise at least 2000 proteins.

Embodiments can further comprise the step of co-registering a spatial region of a biological sample with a NanoPOTS reactor vessel, and with a well. In certain embodiments, the spatial region has dimensions less than or equal to 500 µm. In further embodiments, the spatial region has dimensions less than or equal to 100 µm.

Examples of liquid carrier buffers can include, but are not limited to phosphate-buffered saline, ammonium bicarbonate, tris(hydroxymethyl)aminomethane, liquid chromatography mobile phase, and combinations thereof. In certain embodiments, the liquid carrier buffer contains an MS-compatible surfactant. Examples of the MS-compatible surfactant can include, but are not limited to, ProteaseMAX, RapiGest, PPS Silent Surfactant, oxtyl β-D-glucopyranoside, n-dodecyl β-D-maltoside (DDM), digitonin, Span 80, Span 20, sodium deoxycholate, or a combination thereof.

In certain embodiments, methods can further comprise the step of providing protein identification for each of a plurality of proteins composing the complement of proteins. In other embodiments, the methods and systems can provide a quantification of the protein amount for each protein identification. For example, a mass spectrum is generated for each diluted sample. Accordingly, a MS intensity value exists for every identified protein in each diluted sample. The intensity value can be correlated with a quantity based on a calibration in order to yield a quantification of the identified protein. In further embodiments, the plurality of proteins can comprise at least 1000 proteins. In still further embodiments, the plurality of proteins comprises at least 2000 proteins. In certain embodiments, methods can further comprise generating a visual representation of the protein identifications. In embodiments, the visual representation comprises one or more of the protein identifications mapped to a spatial region of a tissue sample. As used herein, protein identifications refer to identifications based on accurate mass and retention time, or ion fragments by matching to protein sequence database.

In embodiments, the diluted sample volume can be at least 5 μL to enable handling by an autosampler associated with a MS-based analytical instrument. If the volume is too small, the autosampler is incapable of transfer. In certain embodiments, the diluting step further comprises dispensing a volume of a wash solution into the one reactor vessel and subsequently transferring the one reactor vessel's contents to the one well. In further embodiments, said steps of dispensing a volume of a wash solution and said transferring the one reactor vessel's contents are repeated at least once.

In certain embodiments, said transferring the diluted sample from the one well to a MS-based analytical instrument comprises contacting the well plate with a notched tip of a syringe, extracting the diluted sample from the one well into the syringe, and dispensing into the MS-based analytical instrument via the syringe. In certain embodiments, the notched syringe tip is in close proximity to the well plate but does not actually contact. Examples of distances between the notched syringe tip and the well plate include, but are not limited to, less than 0.5 mm, less than 0.1 mm, less than 0.05 mm, and less than 0.01 mm.

In some embodiments, a proteome analysis system comprises a receiver for a nanoPOTS platform plate, the plate comprising a plurality of reactor vessels having a non-zero footprint area less than 25 mm$^2$; a receiver for a microwell plate comprising a plurality of microwells; a sample transfer sub-system comprising a transfer syringe; a motorized translation stage configured to position the transfer syringe and each of the reactor vessels in alignment to facilitate sample extraction from the reactor vessel and further configured to position the transfer syringe and each of the microwells in alignment to facilitate sample dispensing into the microwells; an autosampler comprising an autosampler syringe having a notched syringe tip, wherein the autosampler is configured to position the notched syringe tip in contact with a bottom surface of the microwell; and an MS-based analytical instrument receiving sample injections from the autosampler syringe. Examples of transfer syringes can include, but are not limited to, microliter syringes and nanoliter syringes. Examples of the volume of liquid that is transferred from the nanoPOTS plate to the microwell plate can include, but is not limited to, a non-zero amount that is less than 50 μL, 25 μL, or 15 μL.

In certain embodiments, systems can further comprise a data processing sub-system comprising processing circuitry configured to identify each of at least 250 proteins related to a proteome based on data from the MS-based analytical instrument. In some instances the sub-system is configured to identify each of at least 500, 1000, or 2000 proteins. In other embodiments, systems can further comprise a control sub-system operably connected to the motorized translation sub-system and the autosampler, the control sub-system comprising processing circuitry configured to maintain co-registration between a spatial region of a tissue sample, a processed sample in a reactor vessel, and a diluted sample in a microwell. In still other embodiments, systems can further comprise a data processing sub-system comprising processing circuitry configured to identify each protein related to a proteome based on data from the MS-based analytical instrument, wherein the processing circuitry is further configured to generate a visual representation comprising a mapping of protein identifications to spatial regions of the tissue sample based on the co-registration. In some embodiments there are at least 250, 500, 1000, or 2000 proteins.

Each of the aspects and embodiments described herein are capable of being used together, unless excluded either explicitly or clearly from the context of the embodiment or aspect.

BRIEF DESCRIPTION OF THE DRAWINGS

These and other features will be more readily understood from the following detailed description taken in conjunction with the accompanying drawings, in which:

FIGS. 3A-3E are schematics depicting embodiments of procedures for fabrication and surface modification of a substrate of the chip of FIG. 2. FIG. 3A depicts a schematic of the fabrication and assembly of the chip, where the chip may be pre-coated with an anti-reflective coating (e.g., chromium) and photoresist. FIG. 3B depicts a chip after etching the photomask. FIG. 3C depicts the chip after etching the anti-reflective coating and the substrate to form a patterned substrate. FIG. 3D depicts the patterned substrate including the anti-reflective coating after removal of the photoresist. FIG. 3E depicts the chip after removal of the anti-reflective coating, showing a pattern of pillars and wells.

FIGS. 4A-4B are diagrams illustrating exemplary embodiments of reactor vessels defined by the chip patterned substrate of the chip including pillars and wells formed there between. FIG. 4A depicts one exemplary embodiment of the patterned substrate where the one or more reactor vessels is defined by the upper surfaces of the pillars. The pillars can include hydrophilic upper surfaces and the wells can include hydrophobic upper surfaces.

FIG. 4B depicts another exemplary embodiment of the patterned substrate where the one or more reactor vessels is defined by the wells, between the pillars. In each of FIGS. 4A-4B, the hydrophilic surfaces can be provided by the bare surface of the substrate (e.g., glass surfaces) or hydrophilic coatings. The hydrophobic surfaces can be provided by hydrophobic coatings.

FIG. 5 depicts another exemplary embodiment of a patterned chip substrate in a substantially planar configuration, where the reactor vessels are flush with the substrate surface and defined within first regions of the substrate having hydrophilic surfaces and bounded by adjacent second regions having hydrophobic surfaces.

FIG. 7 depicts exemplary workflow of a sample, including, extraction/reduction, alkylation, Lys-C digestion, trypsin digestion, surfactant cleavage and peptide collection. FIG. 8 depicts an exemplary workflow of a sample (e.g., cells) that are lysed, alkylated, digested—by Lys C and trypsin.

FIG. 11A depicts a base peak chromatogram acquired from 160 cells; an embodiment of a nanowell with cells positioned therein is shown in the insert. FIG. 11B is a bar graph depicting peptide spectral matches (PSMs), unique peptides and identified proteins from duplicate runs of the 160 cells. FIG. 11C depicts a schematic showing the protein overlap from duplicate runs.

FIG. 12A depicts 12 HeLa cells. FIG. 12B depicts 42 HeLa cells. FIG. 12C depicts 139 HeLa cells.

FIGS. 14A-14B are bar graphs depicting the number of unique peptides (FIG. 14A) and protein groups identified from different cell loadings (FIG. 14B).

FIGS. 17A-17D are images depicting the label-free quantification (LFQ) reproducibility. Pairwise correlation of protein LFQ intensities, between, 10-cell and 12-cell samples (FIG. 17A), 37-cell and 42-cell samples (FIG. 17B), 137-cell and 141-cell samples (FIG. 17C). The densities correspond to the greyscale code in FIG. 17A. FIG. 17D depicts a violin plot showing the distributions of coefficients of variance of protein LFQ intensities for the three cell loading groups (10-12 cells, 37-41 cells, and 137-141 cells).

FIGS. 18A-18D depict box charts showing the distributions of (a1 FIG. 18A, b1 FIG. 18B) coefficients of variance and (a2 FIG. 18C, b2 FIG. 18D) log intensities at (a1, a2) peptide and (b1, b2) protein level for three cell loading groups. Peptide intensities were normalized based on global normalization approach in each cell loading group. LFQ intensities generated by Maxquant were used for protein quantification.

(FIG. 23C-23D) Overlap of protein groups identified from similar cell loadings of 10, 12, and 14 cells with (FIG. 23C) MS/MS only method, and (FIG. 23D) combined MS/MS and MBR method.

(FIG. 29B) Image of a nanowell chip with an array of 200-nL pre-populated DMSO droplets. (FIG. 29C) Direct mounting of a nanowell chip on a slide adapter for a PALM microbeam LCM system. (FIG. 29D) Microdissected tissue section and (FIG. 29E) the corresponding tissue pieces collected in nanowells with square side lengths from 20 μm to 200 μm. A 12-μm-thick breast cancer tissue was used as a model sample.

FIGS. 30A-30B (FIG. 30A) Comparison of evaporation time of water and DMSO droplets with different volumes. Each condition was measured with five replicates. (FIG. 30B) Evaluation of the capture efficiency of LCM tissue samples using DMSO droplets. A breast tissue section (12 μm thick) was used as a model sample. The replicates were 75, 75, 75, and 27 for the tissues having side lengths of 20

μm, 50 μm, 100 μm, and 200 μm, respectively. 200 nL DMSO droplets pre-deposited in nanowells with a diameter of 1.2 mm were used for tissue collection.

FIGS. 31A-31G Unique peptides (FIG. 31A) and protein identifications (FIG. 31B) of rat brain cortex tissue samples obtained with laser capture microdissection followed by DMSO and DMSO-free-based sample collection methods. (FIG. 31C) Venn diagram of the total protein identifications. Tissue size: 200 μm in diameter and 12 μm in depth. (FIGS. 31D-31F) Evaluation of the sensitivity of the LCM-DMSO-nanoPOTS system in proteomic analysis of small rat cortex tissue samples. The relationship of tissue sizes with unique peptides (FIG. 31D) and protein (FIG. 31E) identifications, and (FIG. 31F) the overlap of total protein identifications in different sizes. (FIG. 31G) GOCC analysis of the 1918 proteins identified from 200-μm cortex tissues using an online tool DAVID. All peptide and protein identifications were based on MS/MS spectra (Match Between Runs was disabled). Each condition was analyzed in triplicate.

Figure 32A:
Figure 32B:
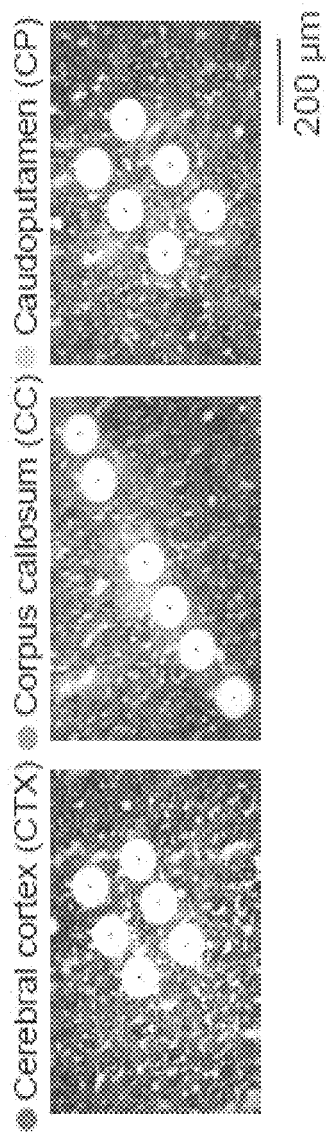
Figure 32C:
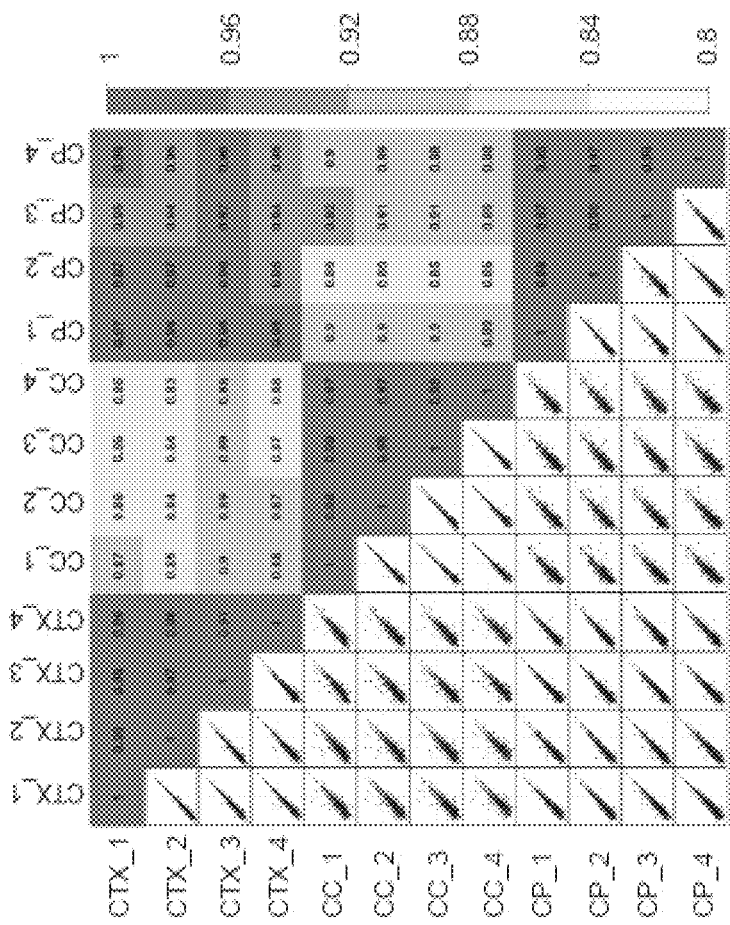

FIGS. 32A-32C. (FIG. 32A) The rat brain coronal section (12 μm thick) used in the study. Three distinct regions including cerebral cortex (CTX), corpus callosum (CC), and caudoputamen (CP) were dissected with a spatial resolution of 100 μm in diameter. (FIG. 32B) The corresponding microscopic images of the tissue regions after dissection. (FIG. 32C) Pair wise correlation plots with $\log_2$-transformed LFQ intensities between total 12 tissue samples from the three regions. The color codes indicate the relatively high correlations between the same tissue regions and relatively low correlations between different regions.

Figure 33A:
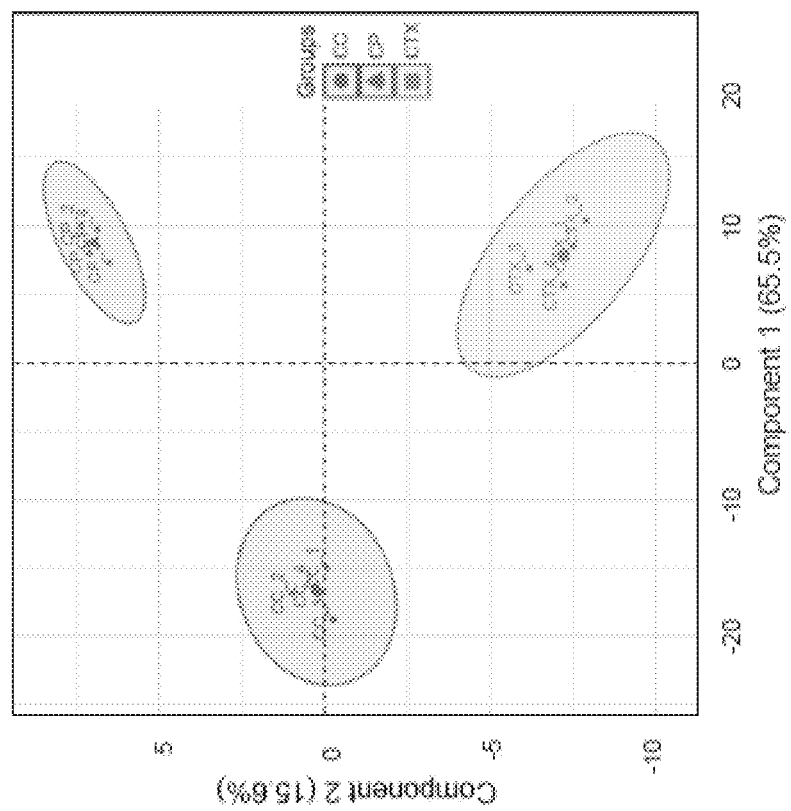
Figure 33B:
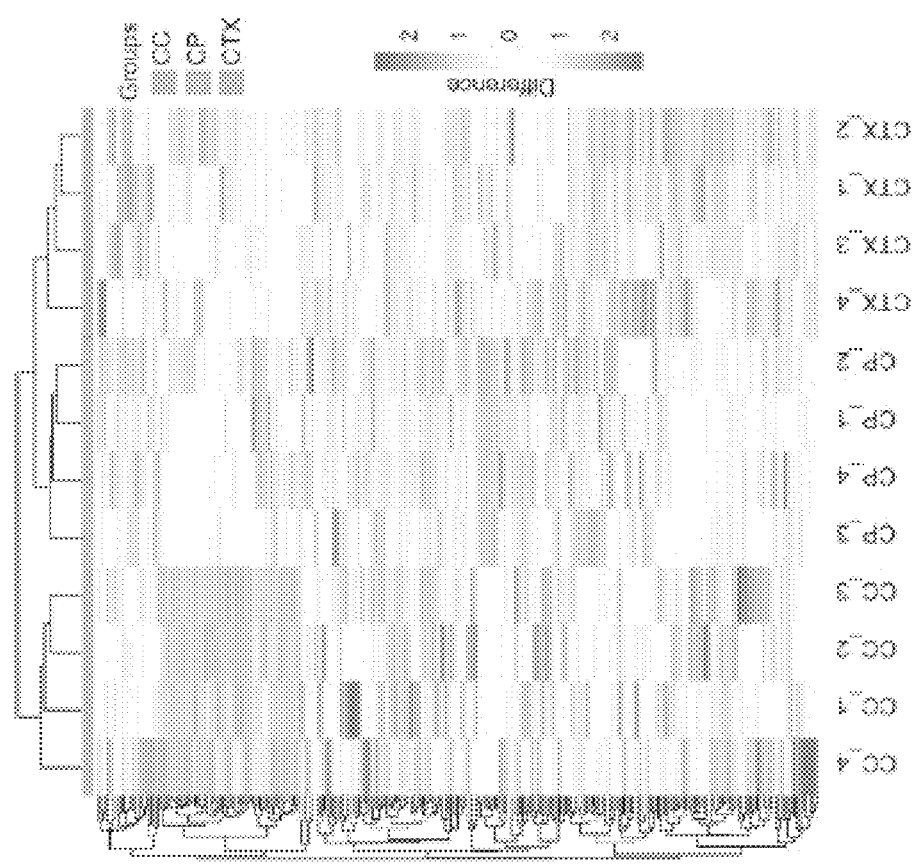

FIGS. 33A-33B. (FIG. 33A) Principle component analysis (PCA) of protein expressions in CTX, CC, and CP regions of rat brain section as shown in FIGS. 32A-32C. (FIG. 33B) Hierarchical clustering analysis (HCA) of the significant proteins.

Figures 34A, 34B:
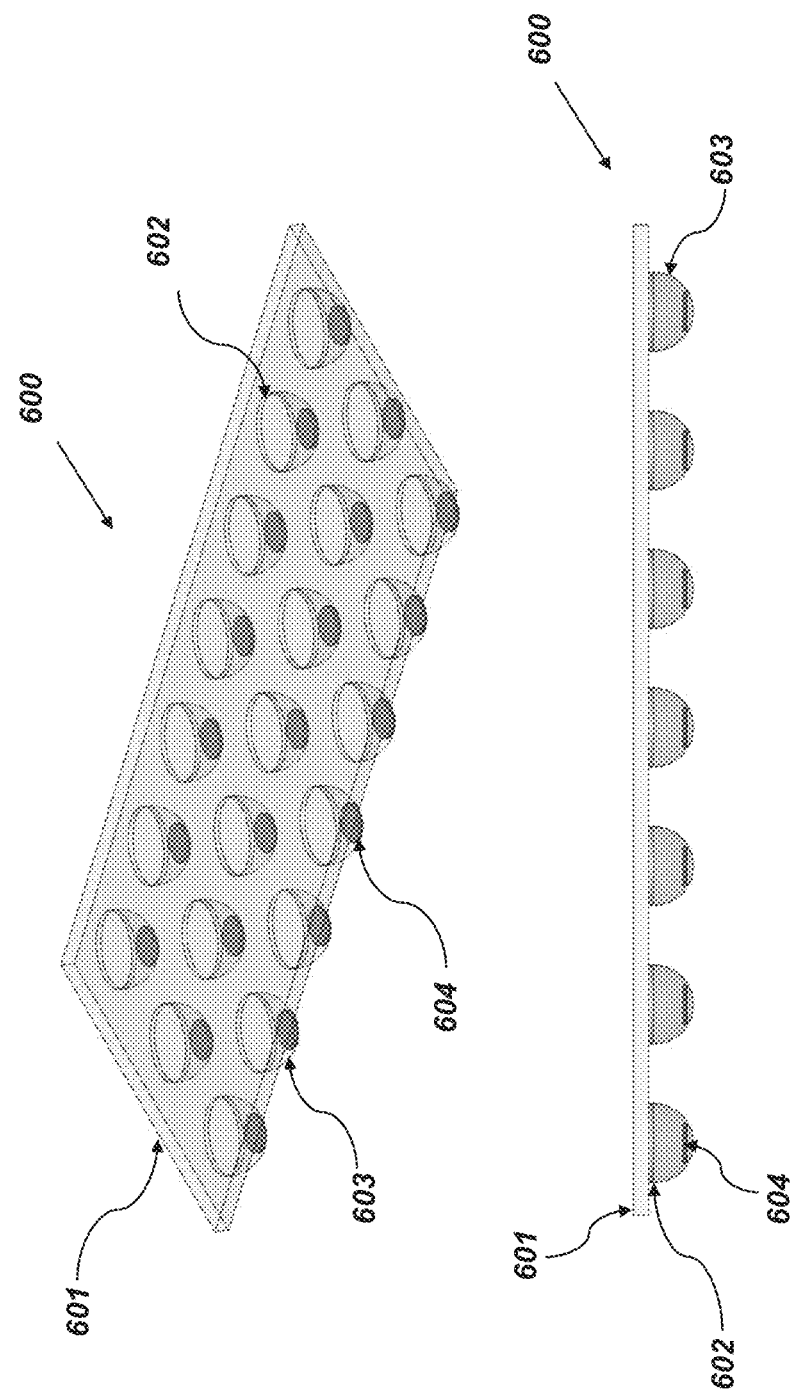

FIG. 34A depicts a top front view of a chip showing droplets hanging from the individual reactor vessels during incubation.

FIG. 34B depicts a side view of a chip showing droplets hanging from the individual reactor vessels during incubation.

Figure 35:
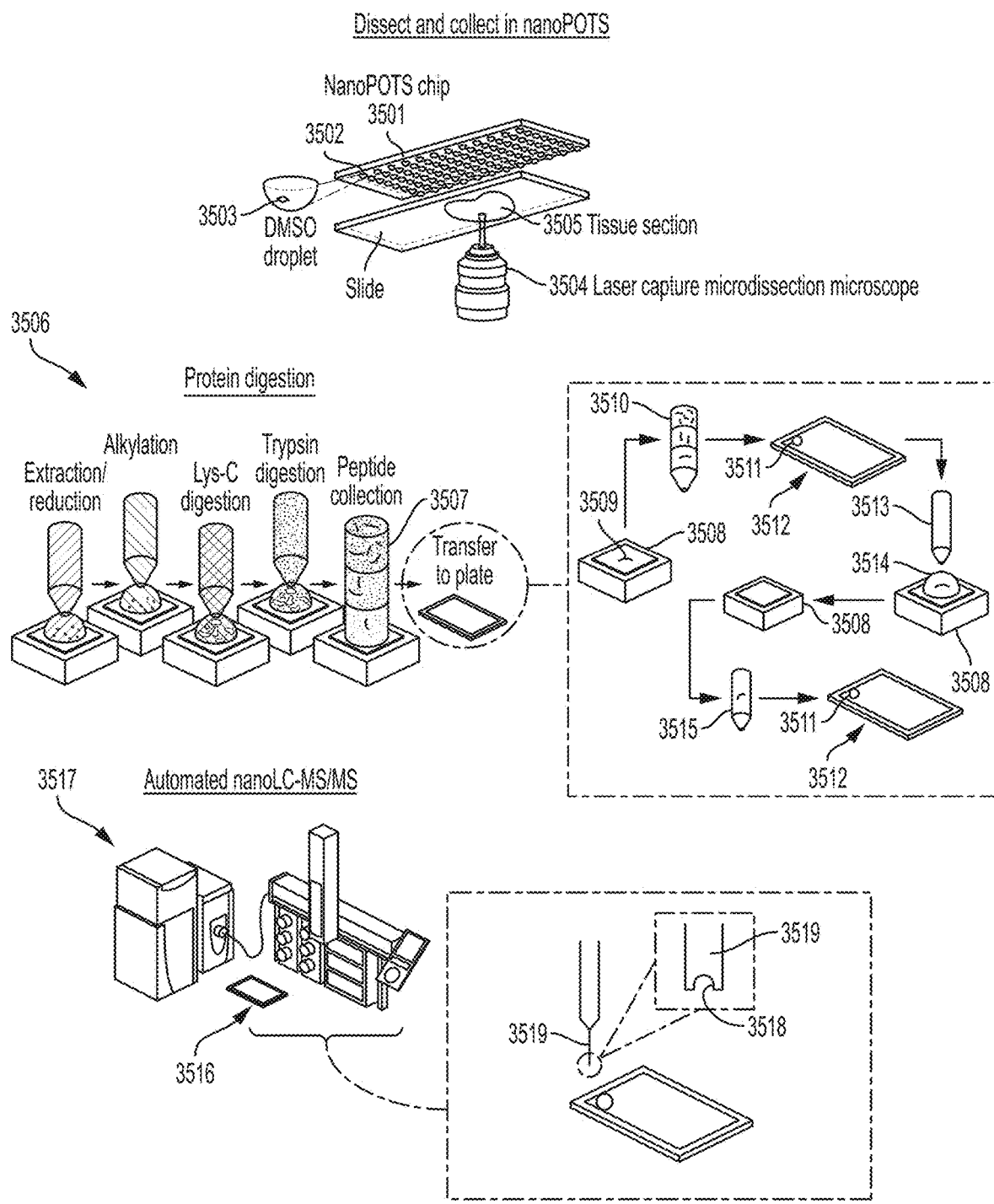

FIG. 35 depicts various aspects of methods and systems for automated proteome analysis according to embodiments described herein.

Figure 36A:
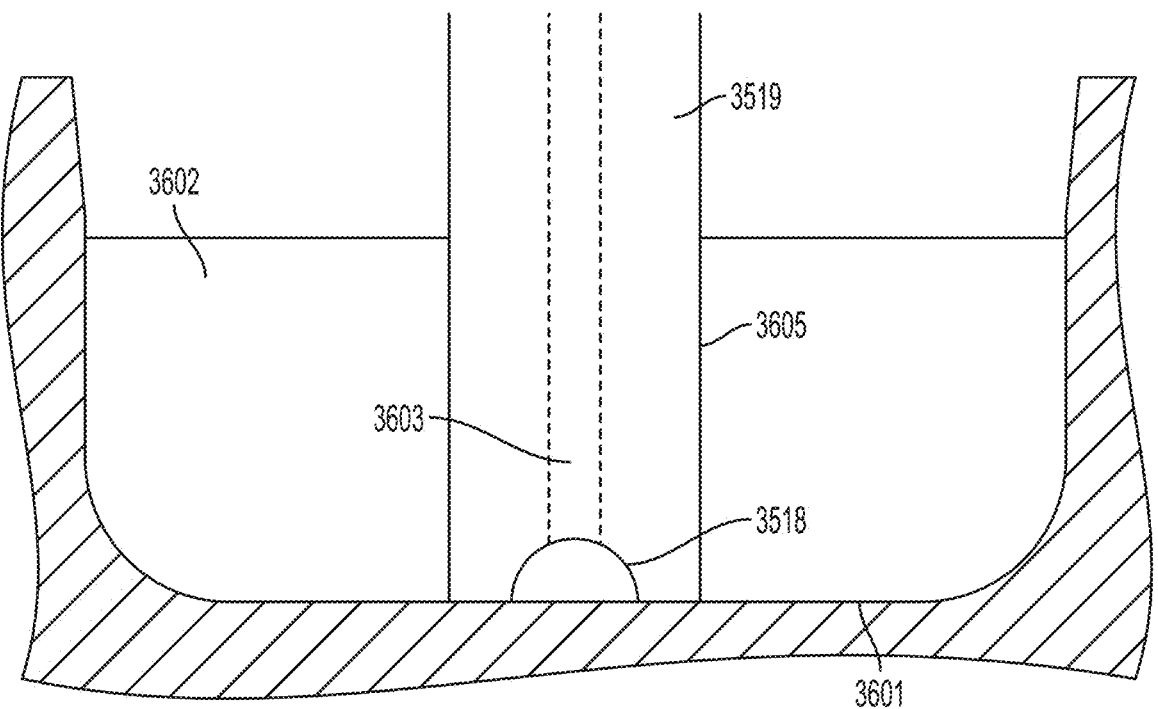
Figure 36B:
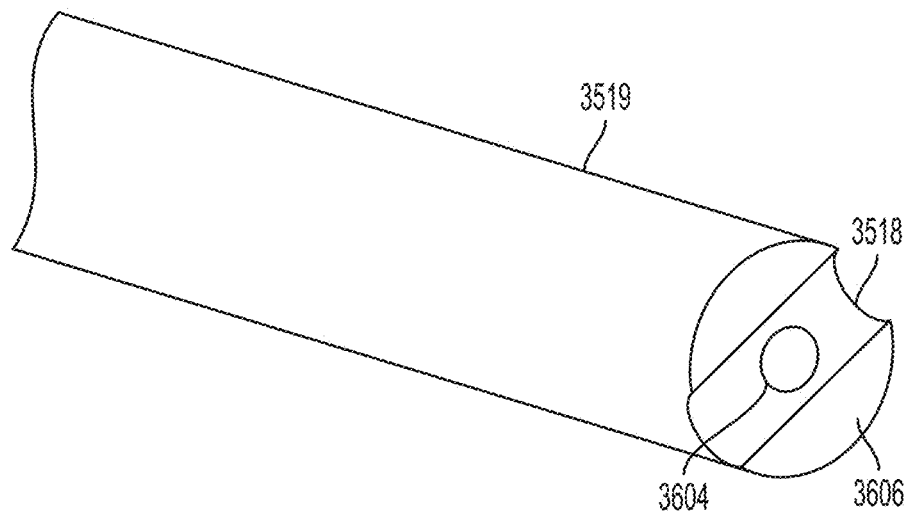

FIGS. 36A and 36B are different perspective views of a notched syringe tip.

Figure 37:
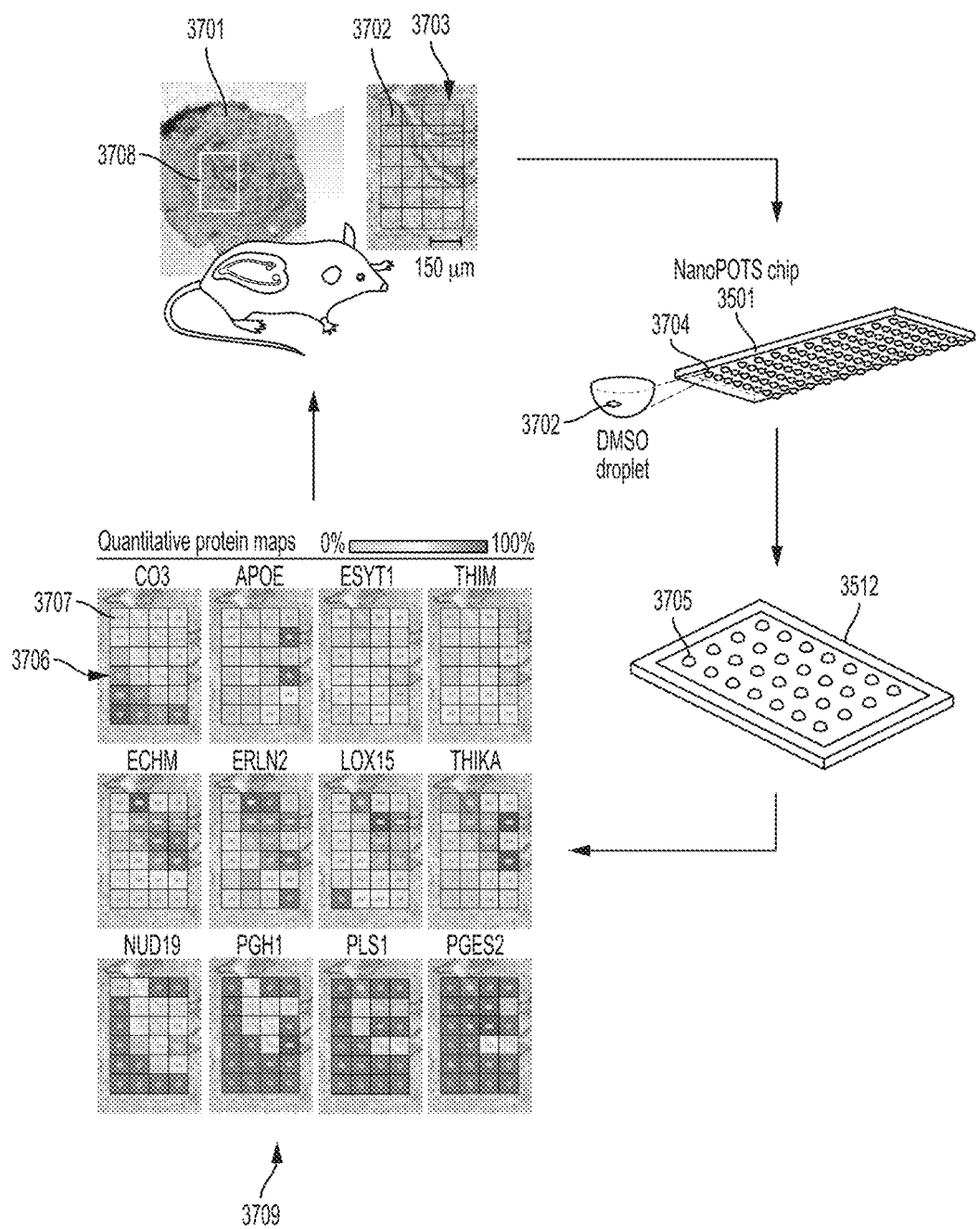

FIG. 37 depicts co-registration of a spatial region of a biological sample with a nanoPOTS reactor vessel and a well-plate well, which facilitates proteome mapping.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the disclosed embodiments is defined solely by the claims.

DETAILED DESCRIPTION

Embodiments of the present disclosure relate to systems and methods for preparation and analytical analysis of biological samples. More particularly, embodiments of the present disclosure relate to preparation and analysis of biological samples having nanoscale volumes, interchangeably referred to herein as nanoPOTS: Nanowell-based Preparation in One-pot for Trace Samples. As discussed in detail below, increased efficiency and recovery of proteomic sample processing by downscaling total preparation volumes to the nanoliter range (e.g., from the range of about 100 μL to about less than 5 μL).

Described herein, proteomic sample preparation and analysis for small cell populations can be improved, for example by reducing the total processing volume to the nanoliter range within a single reactor vessel. The present platform, NanoPOTS, can enable each sample to be processed within a 200 nL or smaller droplet that is contained in a wall-less glass reactor having a diameter of approximately 1 mm (e.g., total surface area of about 0.8 mm$^2$). Compared with a 100 μL typical sample preparation volume in 0.5 mL-centrifuge tubes (127.4 mm$^2$), the surface area was reduced by a factor of ~160, greatly reducing adsorptive losses.

When combined with analysis by ultrasensitive liquid chromatography-mass spectroscopy (LC-MS), biological samples prepared using nanoPOTS can enable deep profiling of greater than about 3000 proteins from as few as about 10 HeLa cells, a level of proteome coverage that has not been previously achieved for fewer than 10,000 mammalian cells. Beneficially, NanoPOTS can enable robust, quantitative and reproducible analyses and provide in-depth characterization of tissue substructures by profiling thin sections of single human islets isolated from clinical pancreatic specimens.

Current State of Molecular Profiling

One of the most dramatic technological advances in biological research has been the development of broad "omics-based" molecular profiling capabilities and their scaling to much smaller sample sizes than were previously feasible, including single cells. Highly sensitive genome amplification and sequencing techniques have been developed for the analysis of rare cell populations, interrogation of specific cells and substructures of interest within heterogeneous clinical tissues, and profiling of fine needle aspiration biopsies (Achim, K. et al., Jaitin, D. et al., and Shapiro E. et al). However, genomic and transcriptomic technologies can fail to comprehensively inform on cellular state (e.g., phenotype) (Bendall, S. et al.). Broad proteome measurements provide more direct characterization of the phenotypes and are crucial for understanding cellular functions and regulatory networks. Flow cytometry (FC) and mass cytometry (MC) (Smith, R. et al.) approaches can utilize antibody-bound reporter species to enable the detection of up to tens of surface markers and intracellular proteins from single cells. As with other antibody-based technologies, these methods can be fully dependent on the availability, quality and delivery of functional antibody probes. FC and MC are also inherently targeted techniques with limited multiplexing capacity. Mass spectrometry (MS)-based proteomics is capable of broadly revealing protein expression as well as protein post-translational modifications (PTMs) within complex samples, but thousands to millions of cells are typically required to achieve deep proteome coverage.

In the absence of methods for global protein amplification, considerable efforts have been devoted to enhancing the overall analytical sensitivity of MS-based proteomics.[6] For example, liquid-phase separations including liquid chromatography (LC) and capillary electrophoresis (CE) have been miniaturized to reduce the total flow rate, leading to enhanced efficiencies at the electrospray ionization (ESI) source (Sun, L et al., and Kelly, R. et al.). Advanced ion focusing approaches and optics such as the electrodynamic ion funnel (Li, S. et al) can minimize ion losses in the transfer from the atmospheric pressure ESI source to the high-vacuum mass analyzer, and are now incorporated into many biological MS platforms. As a result of these and other improvements, mass detection limits as low as 10 zmol for MS and 50 zmol for tandem MS analysis of peptides can be been achieved (Shen, Y. et al., Sun, L. et al. Kelly, R. et al, Sun, X. et al. and Wang, H. et al). This analytical sensitivity can be sufficient to detect many proteins at levels expressed in single mammalian cells (Sun, L. et al. and Kelly, R. et al). However, despite this capability, such performance for 'real' application to such small samples remains largely ineffective.

The major gap between demonstrated single-cell analytical sensitivity and the present practical need for orders of magnitude more starting material largely can derive from limitations in required sample preparation, including sample isolation, cell lysis, protein extraction, proteolytic digestion, cleanup and delivery to the analytical platform. As sample sizes decrease without a concomitant reduction in reaction volume (often limited by evaporation and the microliter volumes addressable by pipet), the nonspecific adsorption of proteins and peptides to the surfaces of reactor vessels, along with inefficient digestion kinetics, can become increasingly problematic.

Efforts to improve sample preparation procedures include the use of low-binding sample tubes and 'one pot' digestion protocols to limit total surface exposure (Sun, X, et al., Wisniewski, J et al, Chen, Q et al, Chen W. et al, Waanders, L. et al, Huang, E. et al, and Wang, N. et al). In addition, trifluoroethanol-based protein extraction and denaturation (Wisniewski, J. et al 2011), filter-aided sample preparation, [13] MS-friendly surfactants (Waanders, L. et al, and Huang E., et al), high-temperature trypsin digestion (Chen, W. et al), adaptive focused acoustic-assisted protein extraction (Sun, X. et al), and immobilized digestion protocols (Wisniewski, J. et al 2011) have further advanced processing of small samples. Using methods such as these, previous work has shown that ~600 to 1500 proteins can be identified from samples comprising 100 to 2000 cells (Table 1 below) (Sun, X, et al, Chen, Q. et al, Chen, W. et al, Waanders, L. et al, Huang, E. et al. and Wang, N. et al).

Recently, single-cell proteomics has been used to explore protein expression heterogeneity in individual blastomeres isolated from *Xenopus laevis* embryos (Lombard-Banek, C. et al, and Sun, L. et al). These measurements were enabled by the fact each of these large cells contained micrograms of proteins, compared to the ~0.1 ng (Wisniewski, J, et al. 2014) of protein found in typical mammalian cells, and were thus compatible with conventional sample preparation protocols.

While progress has been made in enabling the proteomic analysis of trace samples, it is clear that further reducing sample requirements to biological samples containing low- or sub-nanogram amounts of protein while maintaining or increasing proteome coverage can enable many new applications.

Samples

Samples employed in embodiments of the systems and methods described herein may be any liquid, semi-solid or solid substance (or material). In certain embodiments, a sample can be a biological sample or a sample obtained from a biological material. A biological sample can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease).

A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample can be a nuclear extract. In some examples, a biological sample can be bacterial cytoplasm. In other examples, a sample can be a test sample. For example, a test sample can be a cell, a tissue or cell pellet section prepared from a biological sample obtained from a subject. In an example, the subject can be one that is at risk or has acquired a particular condition or disease. In certain embodiments, the sample can be cells isolated from whole blood or cell isolated from histological thin sections. Illustrative biological samples include nanoscale biological samples (e.g., containing low- or subnanogram (e.g., less than about 1 ng) amounts of protein which may be processed in a single nanowell or subdivided into multiple nanowells).

In other examples, the biological sample is a tissue, and the tissue may be fixed. Tissues may be fixed by either perfusion with or submersion in a fixative, such as an aldehyde (such as formaldehyde, paraformaldehyde, glutaraldehyde, and the like). Other fixatives include oxidizing agents (for example, metallic ions and complexes, such as osmium tetroxide and chromic acid), protein-denaturing agents (for example, acetic acid, methanol, and ethanol), fixatives of unknown mechanism (for example, mercuric chloride, acetone, and picric acid), combination reagents (for example, Carnoy's fixative, methacarn, Bouin's fluid, B5 fixative, Rossman's fluid, and Gendre's fluid), microwaves, and miscellaneous (for example, excluded volume fixation and vapor fixation). Additives also may be included in the fixative, such as buffers, detergents, tannic acid, phenol, metal salts (for example, zinc chloride, zinc sulfate, and lithium salts), and lanthanum.

In embodiments, the method for preparing a biological sample may include displacing a volume of biological sample to a single reactor vessel. In embodiments, the volume of biological sample can be a non-zero amount less than 5 µL. In exemplary embodiments, the volume of biological sample may a non-zero amount less than about 4 less than about 3 less than about 2 less than about 1 less than about 500 nL, less than about 400 nL, less than about 300 nL, less than about 200 nL, less than about 190 nL, less than about 180 nL, less than about 170 nL, less than about 160 nL, less than about 150 nL less than about 140 nL, less than about 130 nL, less than about 120 nL, less than about 110 nL, less than about 100 nL, less than about 90 nL, less than about 80 nL, less than about 70 nL, less than about 60 nL, less than about 50 nL, less than about 40 nL, less than about 30 nL, less than about 20 nL, less than about 10 nL, or less than about 1 nL. In particular embodiments, the biological sample comprises about 50 nL.

In other embodiments, the biological sample (e.g., cultured cells or non-cultured cells) may be measured by their confluence. Confluency refers to cells in contact with one another on a surface (e.g., a tissue culture vessel, a petri dish, a well, and the like). For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel.

In embodiments, the biological sample may include HeLa cells, A549 cells, CHO cells or MCF7 cells, K562 cells, or THP-1 cells, microbial cells, plant cells, or virtually any other biological material.

In other embodiments, the biological sample may include of primary or immortalized cells. Examples include but are not limited to, mesenchymal stem cells, lung cells, neuronal cells, fibroblasts, human umbilical vein (HUVEC) cells, and human embryonic kidney (HEK) cells, primary or immortalized hematopoietic stem cell (HSC), T cells, natural killer (NK) cells, cytokine-induced killer (CIK) cells, human cord blood CD34+ cells, B cells. Non limiting examples of T cells may include CD8+ or CD4+ T cells. In some aspects, the CD8+ subpopulation of the CD3+ T cells are used. CD8+ T cells may be purified from the PBMC population by positive isolation using anti-CD8 beads.

In other aspects, the biological sample may include tissues, including but not limited, liver tissue, brain tissue, pancreatic tissue, breast cancer tissue, or plant tissue.

Biological Sample Pre-Preparation

In embodiments, the biological sample is collected and prepared using standard techniques. In aspects, cultured cells are collected and centrifuged. The pellet is then washed and re-suspended. The suspended cells are concentration to obtain desired cell numbers. In embodiments, the desired number of cells can be readily optimized. In certain aspects, the number of cells is 1 cell, 2 cells, 3 cells, 4 cells, 5 cells, 6 cells, 7 cells, 8 cells, 9 cells, 10 cells, 15 cells, 20 cells, 30 cells, 40 cells, 50 cells, 100 cells, 200 cells. In further embodiments, the sample is then adjusted to obtain a nano liter cell suspension (e.g., a 50 nL cell suspension).

In other aspects, the biological sample is a laser microdissected tissue, wherein the tissue is less than about 1000 µm, less than about 900 µm, less than about 800 µm, less than about 700 µm, less than about 600 µm, less than about 500 µm, less than about 400 µm, less than about 300 µm, less than about 200 µm, less than about 100 µm, less than about 50 µm, less than about 40 µm, less than about 30 µm, less than about 20 µm, less than about 10 µm, less than about 5 µm.

Processing the Biological Sample

Figure 1:
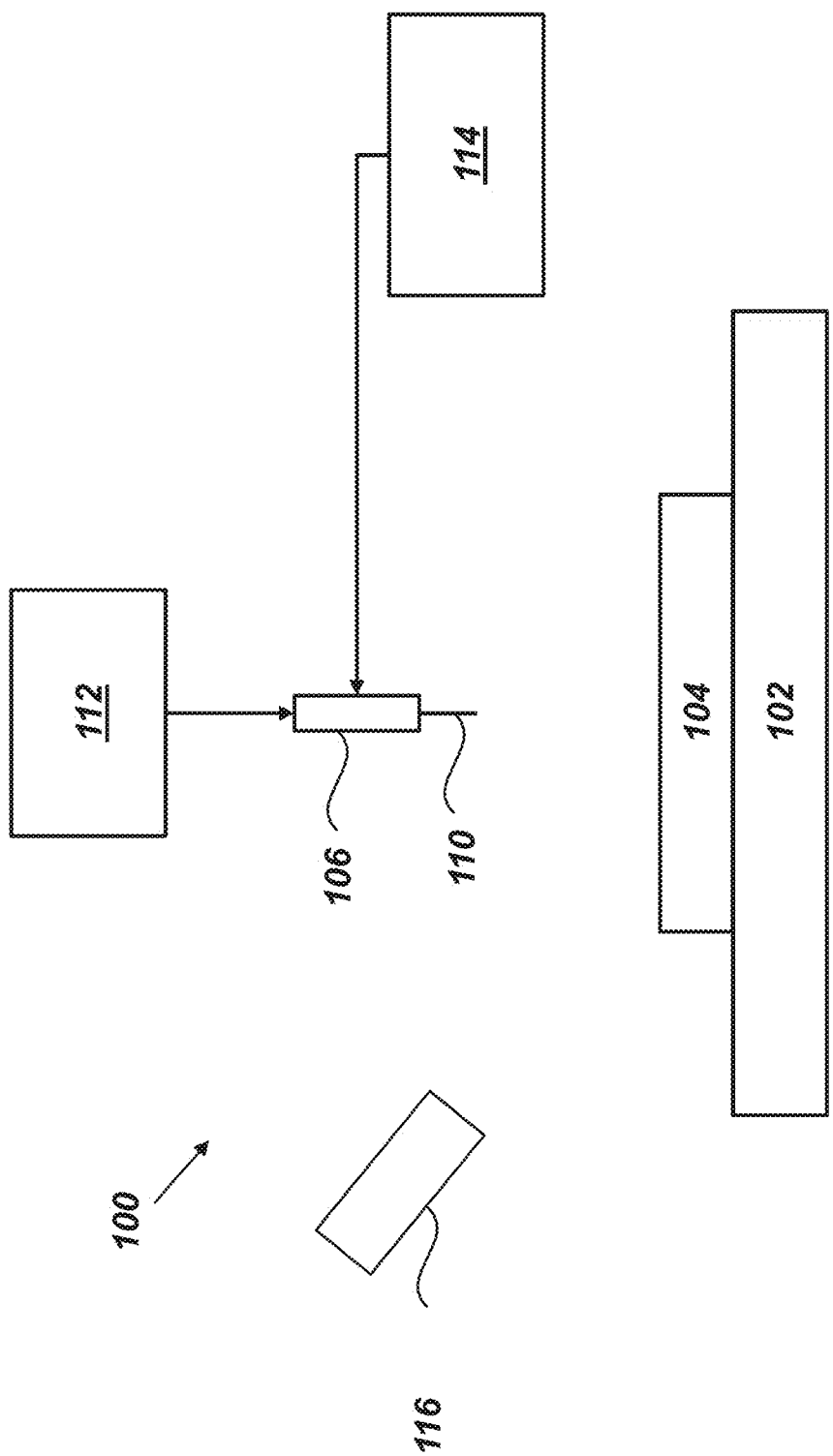
FIG. 1 is a schematic depicting an exemplary embodiment of an operating environment including a robotic platform configured to dispense biological samples and reagents into a chip containing one or more reactor vessels (e.g., nanovessel) for nanoscale sample preparation.

As described herein, a robotic nanoliter dispensing platform 100 can be employed to perform sample processing steps associated with bottom-up proteomics (e.g., robotic platform (Vandermarlier, E et al)). As shown in FIG. 1, dispensing platform 100 can include a translatable stage 102 configured to receive a chip 104. The chip 104 can be configured to retain biological samples and reagents dispensed therein for further processing. The robotic platform 100 can be configured to provide submicron positioning accuracy and capacity for accurately handling picoliter volumes to dispense cells and reagents into reactor vessels formed in the chip 104 for further processing (e.g., to yield a processed sample). and to retrieve samples for subsequent analysis.

Biological samples and/or reagents can be dispensed in the chip 104 via a syringe pump 206 including a picoliter dispensing tip 110 under the control of a controller, which can include one or more user interfaces for receiving commands from a user. The syringe pump 106 can be in fluid communication with a source of the biological samples (not shown) and one or more reservoirs 114 containing reagents. The platform 100 can further include a camera 116 or other imaging device for viewing dispensing of the biological samples and/or reagents.

In embodiments, the total volume of biological samples and/or reagents can be less than 200 nL (in particular embodiments, a non-zero amount of less than 200 nL). Embodiments of the method can dramatically reduce surface contact to minimize sample loss while also enhancing reaction kinetics.

In certain embodiments, the nanoPOTS platform described herein can reduce the total processing volumes (for example, the volume of the biological sample plus the total volume of all the reagents for processing) from the conventional tens or hundreds of microliters to less than 5,000 nL, less than 3,000 nL, less than 2,000 nL, less than 1,000 nL, less than 500 nL, less than 400 nL, less than 300 nL, less than 200 nL, less than 100 nL, less than 50 nL, less than 20 nL, less than 10 nL, less than 5 nL.

As described herein, the biological sample may be processed in a single reactor vessel to yield a processed sample. The single reactor vessel avoids the need to transfer samples to multiple reactor vessels for processing and therefore avoids the corresponding sample losses that such steps incur.

In embodiment, and as described herein the biological sample is processed in a single reactor vessel, a cocktail containing a reducing agent (e.g., dithiothreitol) is added and the sample is incubated. This allows for lysing, extraction, and denaturation of the proteins, and to reduce disulfide bonds in a single step.

In certain aspects, the pH is between 5 and 10, preferably 5, 5.5, 6, 6.5, 7, 7.5, 8, 8.5, 9, 9.5 or 10. More preferably, a solution pH value of 8 may be used.

In an exemplary processing step, a protease is then added to the single reactor vessel (e.g., trypsin or LysC). The addition of a protease allows digestion of the polypeptides.

In some examples, the process may be performed in a humidity-controlled chamber. In some examples, the humidity-controlled chamber is maintained at a relative humidity within the range from about 80% to about 100%, e.g., at about 95% humidity. For chemical or enzymatic processing steps that require extended reaction times at room temperature or elevated temperatures, a cover plate may be employed to minimize evaporation.

In some aspects, the single reactor vessel is sealed during incubation times (e.g., after the addition of a reducing agent). The sealed single reactor vessel aids in minimizing evaporation and therefore sample loss.

Optionally, methods disclosed herein may include steps such as washing steps to maximize recovery (e.g., into a capillary). In aspects, the capillary can be fused or sealed from the external environment and stored. In an example, the processed biological sample is washed with a buffer (e.g., with water containing formic acid), and in some examples, multiple washing steps are performed, for example, 2 washing steps. Storage of the processed biological sample in the capillary may be short term (e.g., at about −20° C. for less than 6 months) or long term (e.g., at about −70° C. for greater than 12 months).

In certain aspects, the chip can be inverted during sample incubation to prevent the sample from settling on the reactor vessel surface (see FIGS. 34A and 34B). For example, droplets containing the biological sample may hang below the reactor vessel surface.

In a further embodiment of the disclosed methods, the processed biological sample can be subjected to mass spectrometry for identification, characterization, quantification, purification, concentration and/or separation of polypeptides without further steps of sample preparation. Since embodiments of the disclosed sample preparation methods can be performed in a single reactor vessel without filtering, precipitation or resolubilization steps, it can facilitate efficient analysis of cell-limited samples.

Analysis of the Biological Sample

Embodiments of the disclosed systems and methods, as described herein, can have broad application in the fields of proteomics, metabolomics, and lipidomics, as such robust analysis from small samples have not been achievable using previously developed procedures. However this description of potential applications is non-limiting and one skilled in the art will appreciate that embodiments of the disclosure can be employed in other applications without limit.

As described herein, biological samples processed according to embodiments of the disclosed systems and methods may be analyzed using a variety of methods. In particular examples, the methods used to analyze the processed biological sample can include, but are not limited to, quantitative proteomic analysis methods. In embodiments, the processed biological sample may be analyzed mass spectrometry.

Mass spectrometry can utilize matrix-assisted laser desorption/ionization (MALDI), electrospray ionization (ESI), and other specialized mass spectrometry techniques. For example, MALDI mass spectrometry is a technique for the analysis of peptide mixtures resulting from proteolysis (e.g., digestion of proteins by trypsin). Embodiments of the methods disclosed herein can be used for top-down or bottom-up proteomics.

Chromatography can also be employed for peptide separation. Liquid chromatography or capillary electrophoresis can be coupled to mass spectrometry, particularly with an electrospray ionization source. In the case of proteomic analysis using liquid chromatography/mass spectrometry, a transfer device (e.g., a transfer capillary) can be directly coupled to a solid-phase microextraction column. The microextraction column can, in turn, be coupled to the head of the liquid chromatography column. Alternatively, the transfer capillary may also be directly coupled to the head of the liquid chromatography column.

In embodiments, the analyzing the processed biological sample can identify unique species, including but not limited to proteins or fragments thereof, lipids, or metabolites.

In embodiments, analyzing the processed biological sample can identify at least about 1,000 unique species (e.g., proteins or fragments thereof, lipids, and/or metabolites). In additional embodiments, the processed biological sample can identify at least 2,000 unique species, at least 3,000 unique species, at least 4,000 unique species, at least 5,000 unique species, at least 7,000 unique species. In other embodiments, the number of unique species identified can be at least 500 or more proteins and/or 100 or more metabolites or lipids.

In embodiments, the methods described herein can allow for the identification and quantitative measurements from less than about 200 cells (e.g., from the range of about 1 to about 50 mammalian cells). In particular embodiments, method described herein enables for identification of over 3,000 unique species from about 10-50 mammalian cells.

In another embodiment, nanowell sample processing can be coupled with laser-capture microdissection (LCM) for deep proteome analysis of heterogeneous tissue thin sections with <100 µm resolution. Deciphering the cellular interactions that drive disease within tissue microenvironment can be beneficial for understanding tumor formation and propagation, developing drug targets, and designing personalized treatment regimens.

While LCM can differentiate and isolate subsections of tissue with high specificity, sample requirements for proteomics can limit the resolution of LCM to large or pooled thin sections comprising thousands or tens of thousands of cells and millimeter or larger dimensions. Such heterogeneous tissues can confound molecular analysis due to a blurring of cellular constituents and their respective contributions. In contrast, embodiments of the presently disclosed systems and methods can provide proteomic analysis of LCM-isolated tissues by reducing sample size by approximately 2 orders of magnitude, to less than about 50 cells, which can enable both high resolution proteomic imaging (e.g., less than about 100 µm) as well as isolation of specific tissues from much smaller samples, such as smears from fine needle aspiration biopsies.

LCM can be used to excise and transfer select tissue from thin section to embodiments of the nanowell. As an example, an LCM (e.g., Zeiss PALM Microbeam LCM®) can be used to excise selected tissue from fresh frozen or archived formalin-fixed, paraffin embedded (FFPE) thin sections (e.g., obtained from Conversant Bio, Inc.). The Zeiss system can provide submicron resolution and it can be equipped with laser-pressure catapulting to eject excised samples to a variety of substrates, including centrifuge tube lids and slides (e.g., 25×75 mm). The Zeiss LCM can be compatible with standard glass slides for archived specimens as well as LCM-dedicated polymer membrane-coated slides.

Embodiments of the nanowells can be configured for compatibility with the 25×75 mm form factor. This can allow for direct coupling and facilitate transfer from thin sections to the nanowells. As discussed in greater detail below, the nanowells can have a diameter of about 0.5 mm to about 1.5 mm. The spacing between the nanowell slide and the thin section slide may be adjusted to achieve the requisite transfer accuracy. Nanowell surface treatments may be implemented as needed to ensure adhesion of the catapulted tissue upon contact. As an alternative approach, excised samples can be catapulted into centrifuge tube caps and micromanipulation-based strategies can be used to transfer the sample to the nanowell.

In embodiments sample processing can be seamlessly integrated with LCM by providing a capture liquid in or on a reactor vessel. This method can avoid manual transfer of dissected tissues to the nanowells that is required in a conventional LCM system. In a conventional LCM system, after being dissected, tissue pieces may be collected into microtubes by gravity or catapulted into tube caps prefilled with extraction solution or adhesive coating, depending on the instrument vendor and configuration. However, these collection approaches cannot be automatically integrated with a nanoPOTS system because the rapid evaporation of nanoliter-scale extraction solution and the prohibitive absorptive losses of proteins on the adhesive silicone coating. Utilizing a sacrificial capture medium in the nanowells addresses this challenge.

The capture liquid may have an ultra-low vapor pressure (for example, less than or equal to 0.8 mbar at room temperature), and evaporates very slowly under ambient conditions, which allows for long working times and uninterrupted sample collection. For example, as shown in FIG. 30A, the evaporation times of 100 nL to 300 nL dimethyl sulfoxide (DMSO) droplets were 194 min to 416 min, which were >50 times longer than for water droplets. Such prolonged times are sufficient to collect up to hundreds of tissue samples in each chip. The capture liquid can be completely removed by gentle heating or vacuum, eliminating any possible interference during subsequent sample processing and analysis steps. Compared with other low-vapor-pressure solvents such as dimethylformamide, the capture liquid should have a lower toxicity, thus enabling its use as a storage solvent for cells. An illustrative capture liquid is dimethyl sulfoxide (DMSO). In addition to having an ultra-low vapor pressure and lower toxicity, the freezing point of DMSO is 18.5° C., which should facilitate chip and sample transfer between histology and analytical labs without the risk of sample mixing or losses during shipping. In addition, it has been presently found that DMSO significantly increases the sensitivity of protein identification of brain tissues, which may be ascribed to improved protein extraction efficiency as explained in more detail below. The amount of capture liquid provided in each nanowell may be sufficient to cover a portion of, or the entire surface, of the nanowell. For example, the capture liquid may be present in an amount of at least 1 nL to 1000 nL.

Molecular Characterization and Disease Profiles

Embodiments of the methods described herein can be used for molecular characterization of tissue cellular heterogeneity or pathology in a variety of diseases. Exemplary diseases can include, but are not limited to, inflammatory diseases, metabolic diseases, cancers, neoplasias, and the like.

As used herein, metabolic disease can include its customary and ordinary meaning and can refer to diabetes, including type II diabetes, insulin-deficiency, insulin-resistance, insulin-resistance related disorders, glucose intolerance, syndrome X, inflammatory and immune disorders, osteoarthritis, dyslipidemia, metabolic syndrome, non-alcoholic fatty liver, abnormal lipid metabolism, neurodegenerative disorders, sleep apnea, hypertension, high cholesterol, atherogenic dyslipidemia, hyperlipidemic conditions such as atherosclerosis, hypercholesterolemia, and other coronary artery diseases in mammals, and other disorders of metabolism. For example, the methods as used herein can be used in characterizing type 1 or type 2 diabetes.

As used herein, neoplasia can include its customary and ordinary meaning and can refer to a disease or disorder characterized by excess proliferation or reduced apoptosis. Illustrative neoplasms for which the embodiment may be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

Definitions

While various embodiments and aspects of the present disclosure are shown and described herein, it will be obvious to those skilled in the art that such embodiments and aspects are provided by way of example only. Numerous variations, changes, and substitutions can occur to those skilled in the art without departing from the disclosed embodiments. It should be understood that various alternatives to the embodiments described herein may be employed.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise herein, all technical and scientific terms used herein have the same meaning as commonly understood by one of ordinary skill in the art to which embodiments of the disclosure pertains.

As used herein, the term "biological sample" can include its customary and ordinary meaning and can refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

A biological sample may be of prokaryotic origin or eukaryotic origin (e.g., insects, protozoa, birds, fish, or reptiles). In some embodiments, the biological sample can be mammalian (e.g., rat, mouse, cow, dog, donkey, guinea pig, or rabbit). In certain embodiments, the biological sample can be of primate origin (e.g., example, chimpanzee, or human).

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed embodiments.

"Detectable moiety" or a "label" can include its customary and ordinary meaning and it can refer to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety can generate a measurable signal, such as a radioactive, chromogenic, or fluorescent signal, that can be used to quantify the amount of bound detectable moiety in a sample. Quantitation of the signal can be achieved by, e.g., scintillation counting, densitometry, mass spectrometry, and/or flow cytometry.

By "FFPE" can refer to formalin fixed paraffin embedded tissue. FFPE samples can be derived from tissues (often suspected tumor samples) that are fixed with formalin to preserve structural-spatial and biomolecule characteristics (e.g., cytoskeletal and protein structure) and then embedded in a type of paraffin wax so the tissue can be sliced. Formalin can irreversibly cross-link proteins via the amino groups, thus preserving the structural integrity of the cells so they can be stained with dyes or with immunostains used to analyze for abnormalities in the tissue that indicate altered cellular conditions, e.g., cancer. However, the effect of these cross-linking fixatives on the RNA and DNA nucleic acids within the sample can be detrimental to the sensitivity and specificity achievable in current molecular assays e.g., molecular assays which use DNA or RNA derived from FFPE samples. Additionally, samples may be prepared using non-formalin reagents, including, for example, glutaraldehyde, mercurial, oxidizing agents, alcohols, and picrates.

The term "hydrophilic surface" can include its customary and ordinary meaning and it can refer to a surface to have native hydrophilic property such as glass or fused silica, or which either hydrophilic compounds are covalently or non-covalently attached or which is formed of a polymer that has hydrophilic properties. In embodiments, the polymer with hydrophilic properties can be an organic polymer, (e.g., polyacrylamide, polyacrylic acid, polyacrylimide, polyelectrolytes, polyethylenimin, polyethylenglycol, polyethylenoxid, polyvinylalcohol, polyvinylpyrrolidon polystyrenesulfonic acid, copolymers of styrene and maleic acid, vinyl methyl ether malic acid copolymer, and polyvinylsulfonic acid.

As used herein, the singular terms "a," "an," and "the" include the plural reference unless the context clearly indicates otherwise.

EXAMPLES

Example 1: Nanodroplet

NanoPOTS Platform Design and Operation

Figure 2:
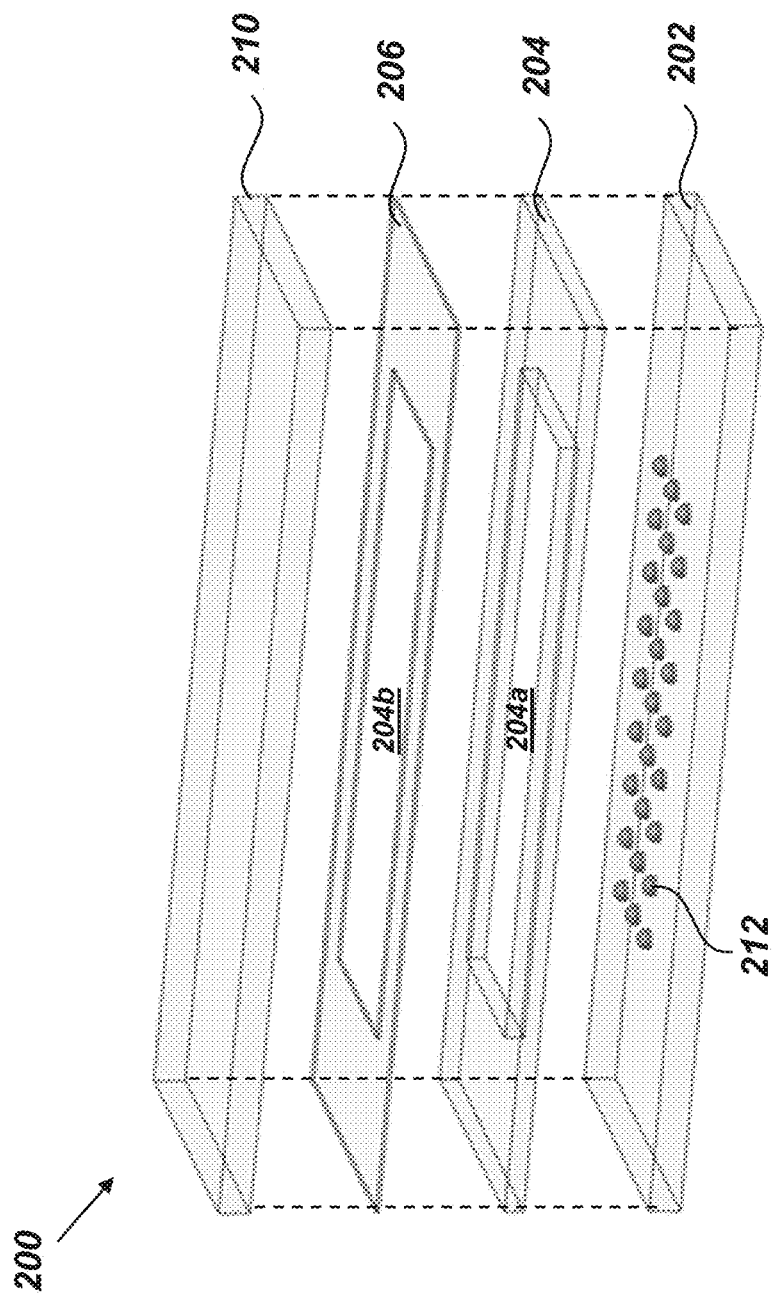
FIG. 2 is a schematic of the chip of FIG. 1 including a substrate, a spacer, a sealing membrane, and a cover slide. The cover slide can be reversibly secured to the spacer for dispensing and incubation

An exemplary embodiment of a nanoPOTS chip, also referred to as a platform or chip 200, is illustrated in FIG. 2. The chip 200 can include a substrate 202, a spacer 204, one or more sealing membrane 206, and a cover 210. When the chip is assembled, the spacer 204 can overlie the substrate 202, the sealing membrane 206 can overlie the spacer 204, and the cover 210 can overlie the sealing membrane 206.

In certain embodiments, the substrate 202, the spacer 204, and the cover 210 can be formed from a material that is transparent to optical light (e.g., glass). Forming the substrate 202 from glass can facilitate microscopic imaging of samples and minimize protein and peptide adsorption relative to many other materials due to its hydrophilicity and reduced surface charge at low pH (Zhu, Y, et al.).

As discussed in greater detail below, the substrate 202 can include a physical and/or chemical pattern 212 that defines at least one reactor vessel having one or more hydrophilic and/or hydrophobic surfaces configured for containment of a biological sample. In certain embodiments, the hydrophilic surfaces can have a non-zero total surface area less than 5 mm$^2$.

The spacer 204 can contain a first aperture 204a and the sealing membrane 206 can include a second aperture 206a. The first and second apertures 204a, 206a can be dimensioned to accommodate the pattern 212 of reactor vessels when the chip 200 is assembled. As an example, at least the first aperture 204a of the spacer can surround the pattern 212 of reactor vessels.

The sealing membrane 206 can be interposed between the spacer 204 and the cover 210 and it can be configured to form a fluid-tight seal between the spacer 204 and the cover 210. In other embodiments, not shown, the sealing membrane can be interposed between the substrate and the spacer. Formation of fluid-tight seals using the sealing membrane can minimize evaporation of reactor vessel contents when performing incubation during sample preparation, as discussed below. Optionally, other sealing mechanisms can be employed and the sealing membrane can be omitted. For example, the cover 210 can be pre-coated with a layer of sealing membrane such as PDMS (polydimethylsiloxane).

FIGS. 3A-3E illustrate an exemplary embodiment of forming the pattern 212 by photolithography. In FIG. 3A, a substrate 300 coated with an anti-reflective coating 302 and photoresist 304 is illustrated. A photomask 306 can be used in conjunction with light 310 (e.g., ultraviolet light) to transfer a geometric pattern of the photomask 306 to the photoresist 304. The anti-reflective coating 302 can be configured to control reflection and absorption of the light 310. As shown in FIGS. 3B-3C, the portions of the photomask 306 and anti-reflective coating 302 outside the transferred pattern can be removed by a chemical etching to yield a patterned substrate 312 that includes pillars 314 defining wells 316 therebetween of predetermined depth within the substrate 300. The photomask 306 and anti-reflective coating 302 remaining on the upper surface of the pillars 312 are removed with further chemical etching, as shown in FIGS. 3D-3E.

Figure 4A:
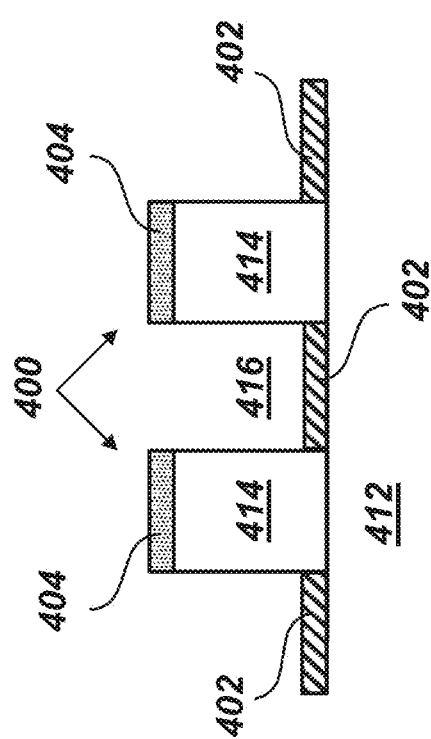
Figure 4B:
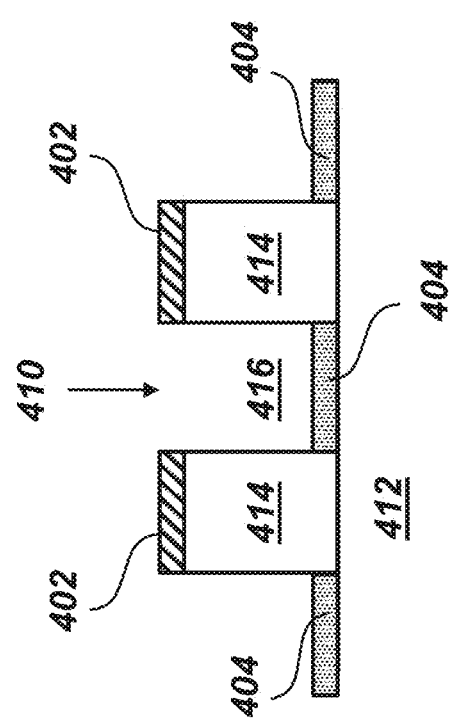
Figure 6:
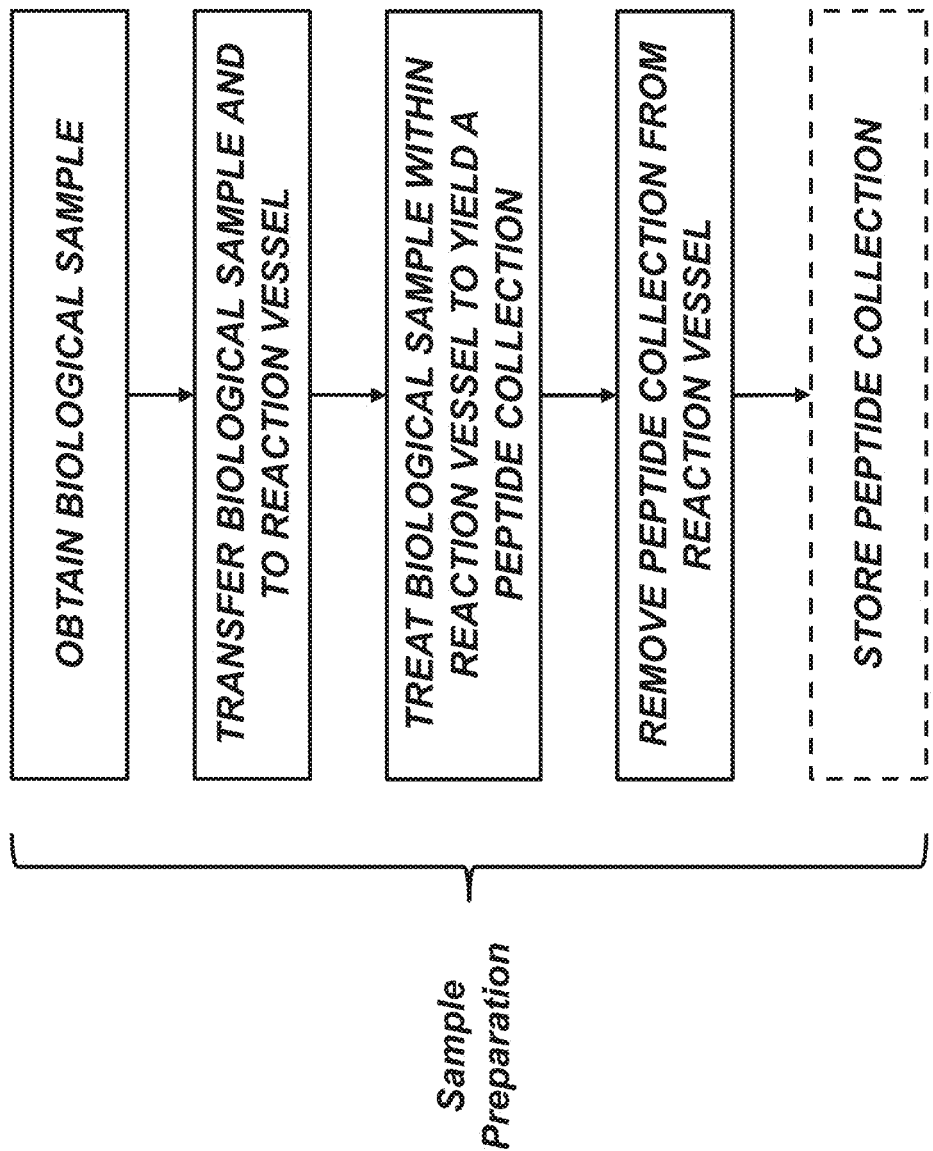
FIG. 6 depicts a flow diagram illustrating one exemplary embodiment of a sample preparation protocol for the methods described herein including a biological sample treatment operation.

FIGS. 4A-4B illustrate embodiments of the patterned substrate 412 defining reactor vessels configured for multiple-step proteomic sample processing. As shown in FIG. 4A, a hydrophobic coating can be deposited on the patterned substrate 412, adjacent to the pillars 414, to form a hydrophobic surface 402. A hydrophilic coating can be deposited on the patterned substrate 412 on the upper surface of the pillars 414 to form a hydrophilic surface 404. Alternatively, when the substrate is formed from a hydrophilic material, a hydrophobic coating can be omitted and the bare surface of the substrate can form the hydrophilic surface 404. So configured, the upper surface of each pillar 414 with the hydrophilic surface 404 can define the lateral boundary of respective reactor vessels 400. In certain embodiments, the patterned pillars 414 can reduce surface area contact relative to the use of concave wells.

Conversely, as shown in FIG. 4B, the locations of the hydrophobic and hydrophilic coatings can be reversed. That is, the hydrophilic coating can be deposited on the patterned substrate 412 adjacent to the pillars 414 (e.g., within the wells 416) to form the hydrophilic surface 404. Alternatively, as discussed above, when the substrate is formed from a hydrophilic material, a hydrophobic coating can be omitted and the bare surface of the substrate can form the hydrophilic surface 404. Likewise, the hydrophobic coating can be deposited on the patterned substrate 412 on the upper surface of the pillars 414 to form the hydrophobic surface 402. So configured, the wells 416 with the hydrophilic surface 404 can define the lateral boundary of respective reactor vessels 410.

In another embodiment, as illustrated in FIG. 5, a patterned substrate 500 can be formed by a pattern of hydrophobic surfaces 402 and hydrophilic surfaces 404 alone, without pillars 414 or wells 416. The hydrophobic surfaces 402 and the hydrophilic surfaces can be provided as discussed above and they can define the lateral extent of the one or more reactor vessels 420.

In certain embodiments, as illustrated in FIGS. 34A and 34B, a chip 600 that includes a substrate 601 and reactor vessel pillars 602 is inverted during processing of a biological sample. A droplet 603 of a capture liquid suspends from the hydrophilic surface of the reactor vessel pillar 602. The capture liquid droplet 603 contains a biological sample 604 that can be subjected to processing.

Figure 7:
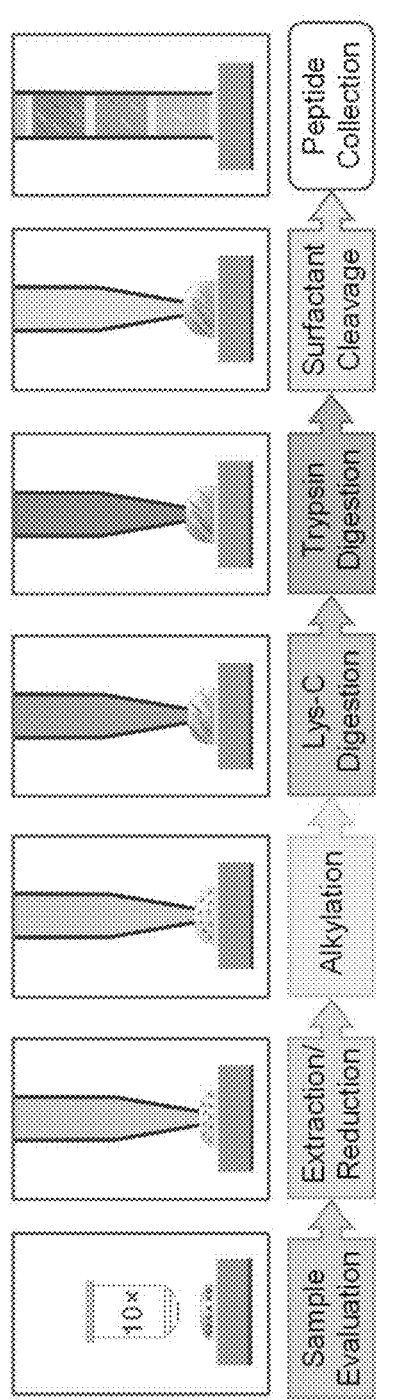
FIGS. 7-8 depict schematics of exemplary embodiments of the sample preparation of the methods described herein.
Figure 8:
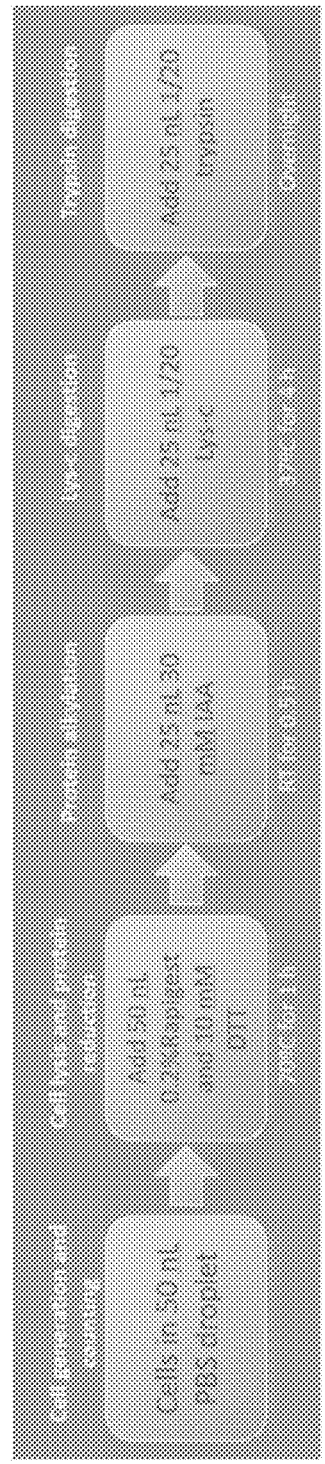
Figure 9:
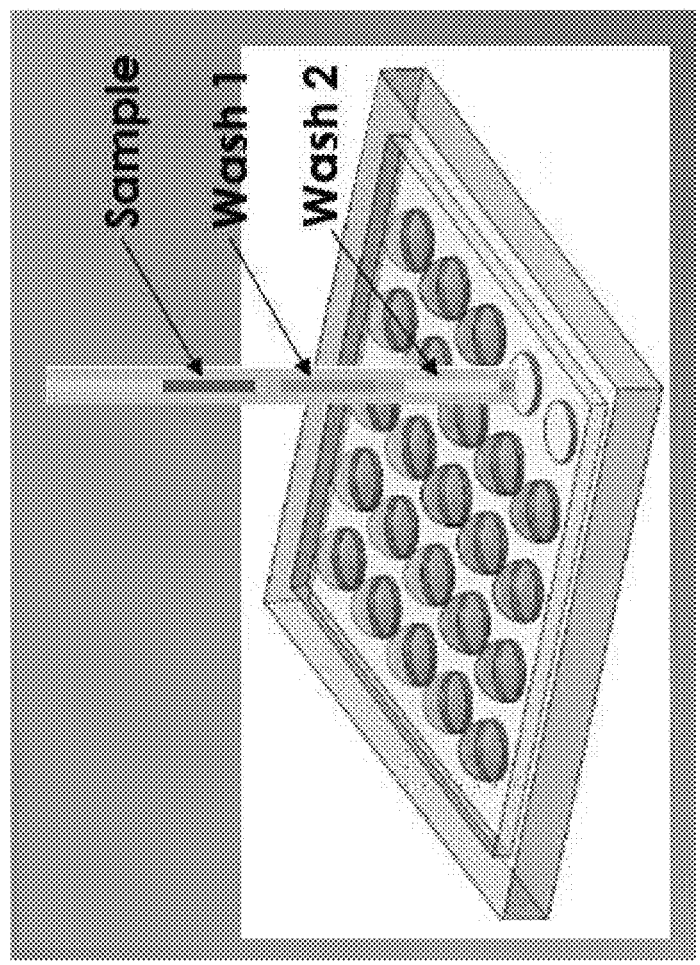
FIG. 9 illustrates an exemplary operating environment including a transfer vessel in the form of a capillary collecting a processed biological sample via aspiration from the nanowell chip.
Figure 10:
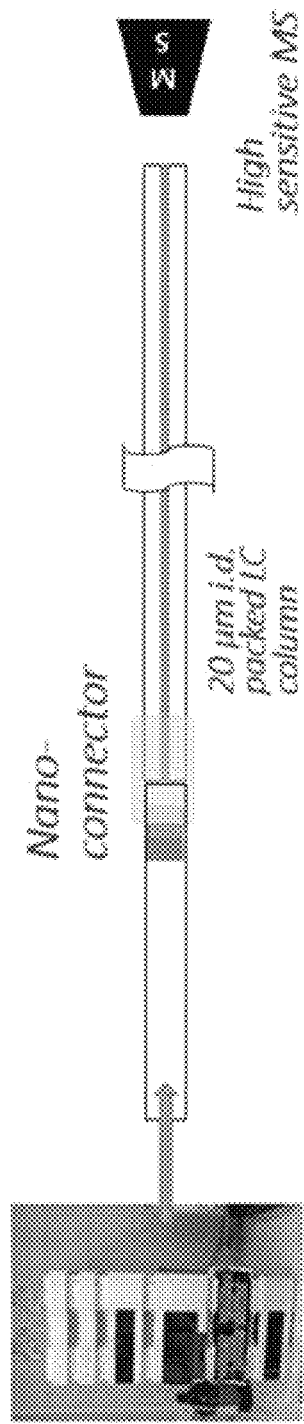
FIG. 10 is a schematic of a capillary used to collect processed sample which can be readily connected to an analytical instrument, such as a mass spectrometer.
Figure 11A:
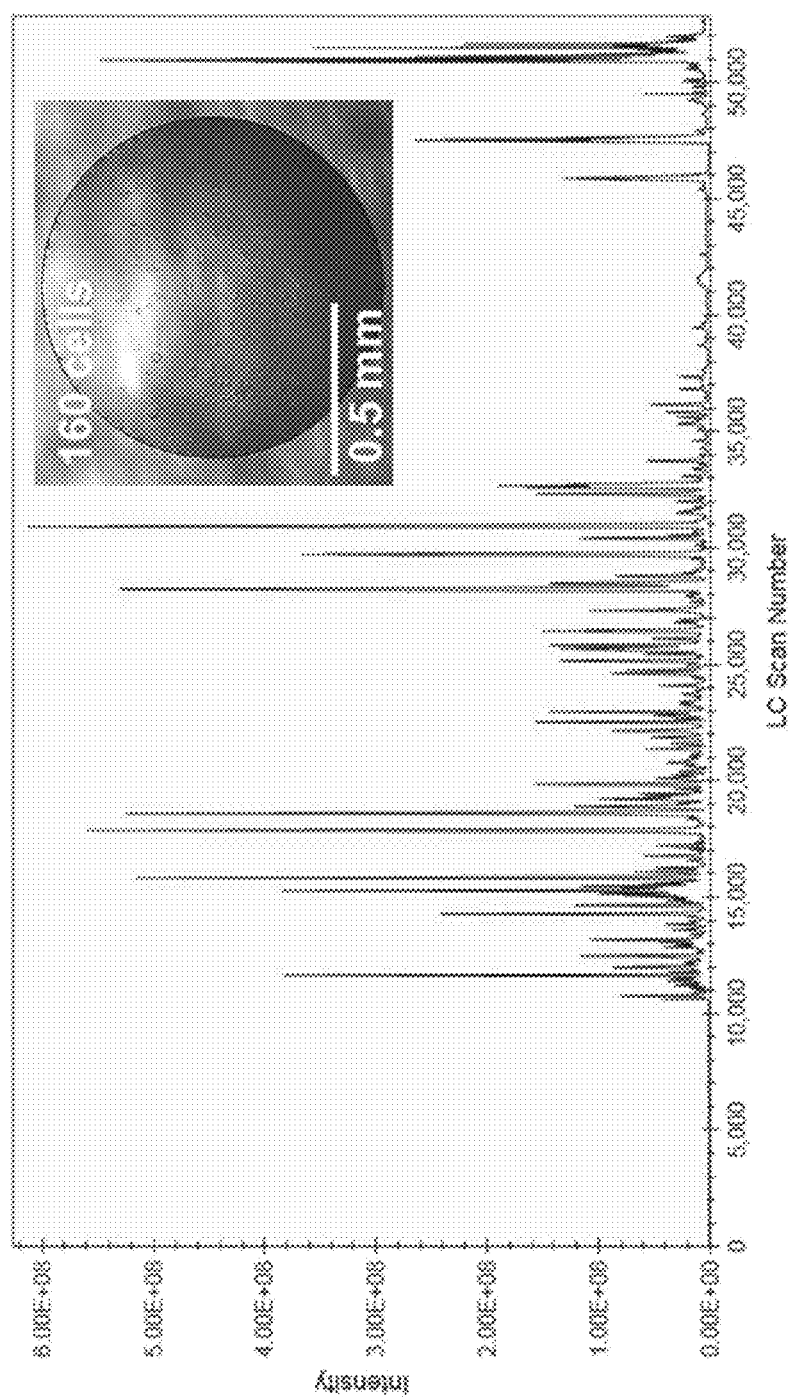
FIGS. 11A-11C depict preliminary proteomic results employing embodiments of the sample preparation method of FIG. 6.
Figure 11C:
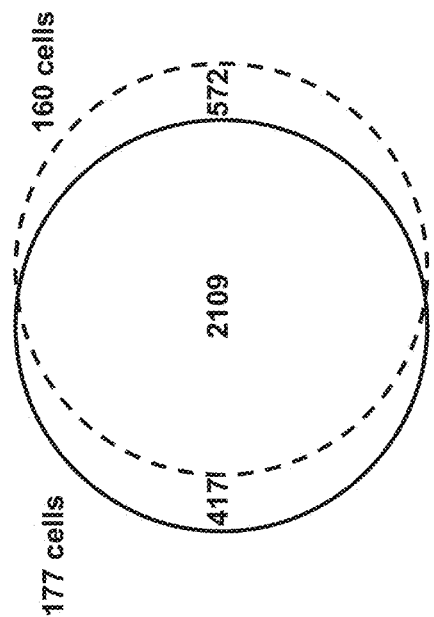
Figure 11B:
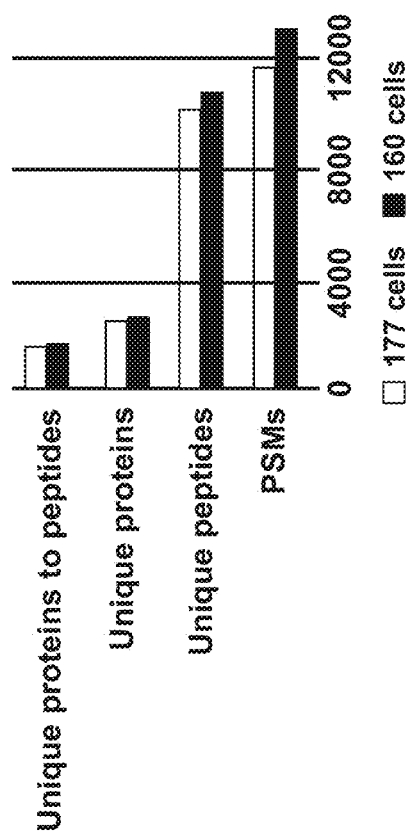

In an embodiment, the RapiGest-based one-pot protocol (Waters, Milford, USA) was adapted for proteomic sample preparation with minimal modification (FIGS. 7-8). Briefly, after cells or other tissue samples were deposited into each chamber of the array, microscopic imaging was used for sample size quantification (cell number, tissue dimensions, etc.). A cocktail containing RapiGest and dithiothreitol was added and incubated at 70° C. to lyse cells, extract and denature proteins, as well as reduce disulfide bonds in a single step. The proteins were alkylated and digested using a two-step enzymatic hydrolysis. Finally, the solution was acidified to cleave and inactivate the RapiGest surfactant. Manipulations were conducted in a humidified chamber, and the cover plate was sealed to the nanowell chip during extended incubation steps to minimize evaporation of the nanoliter droplets. The prepared sample was collected into a fused-silica capillary, followed by a two-step wash of the nanowell to maximize recovery (FIG. 7). The collector capillary can be fully sealed and stored in a freezer for months without observable sample loss. The capillary also simplified downstream solid-phase extraction-based cleanup and LC-MS analysis by enabling direct coupling with standard fittings.

Sensitivity and Proteome Coverage

Figures 12A, 12B, 12C, 13A, 13B, 13C:
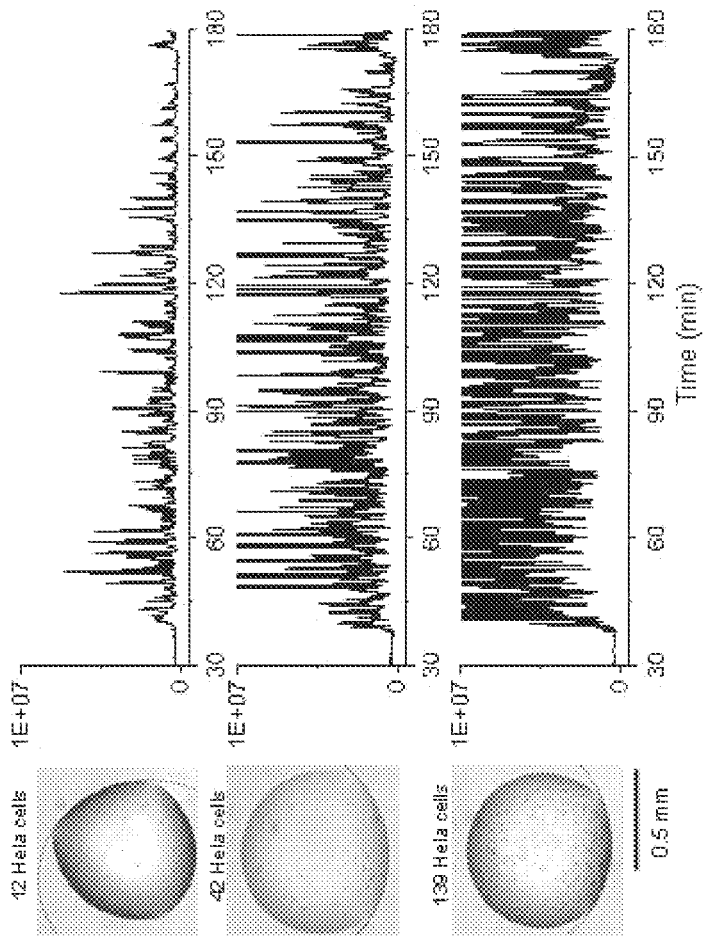
FIGS. 12A-12C are images depicting HeLa cells in nanowells.
FIGS. 13A-13C are base chromatograms of the HeLa cells in nanowells corresponding to FIGS. 12A-12C, respectively.
Figures 14A, 14B:
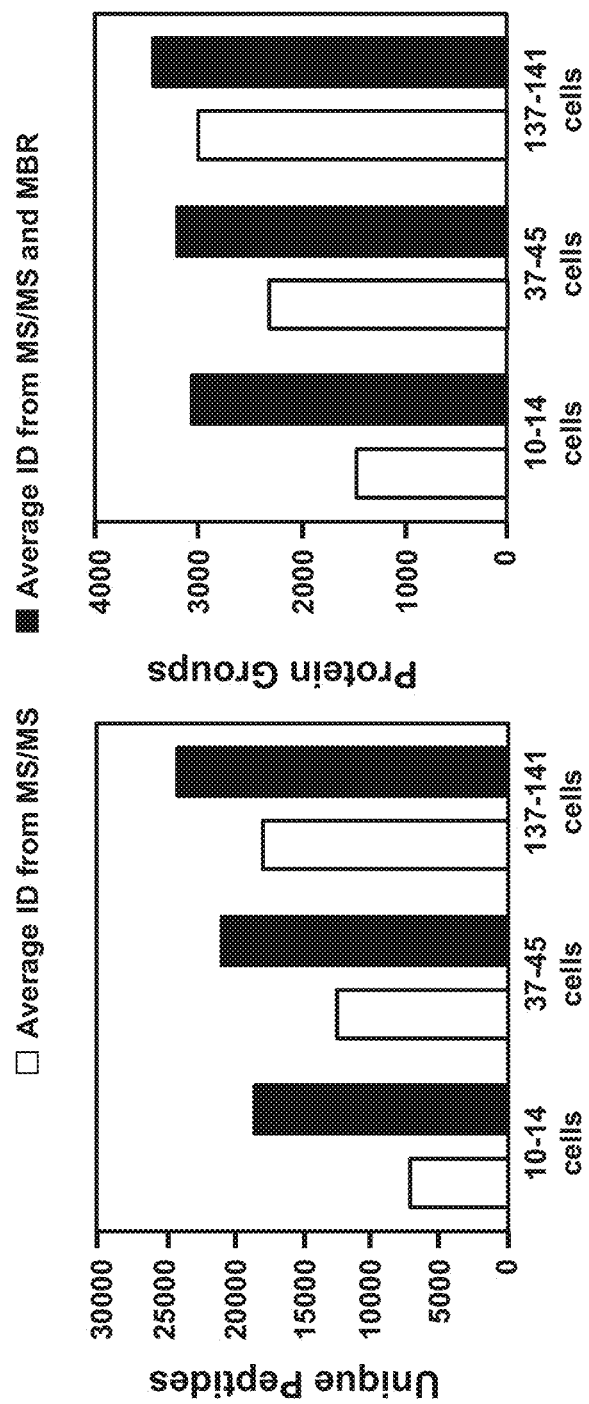
FIGS. 14A-14B show the sensitivity and reproducibility of the nanoPOTS platform.
Figure 15:
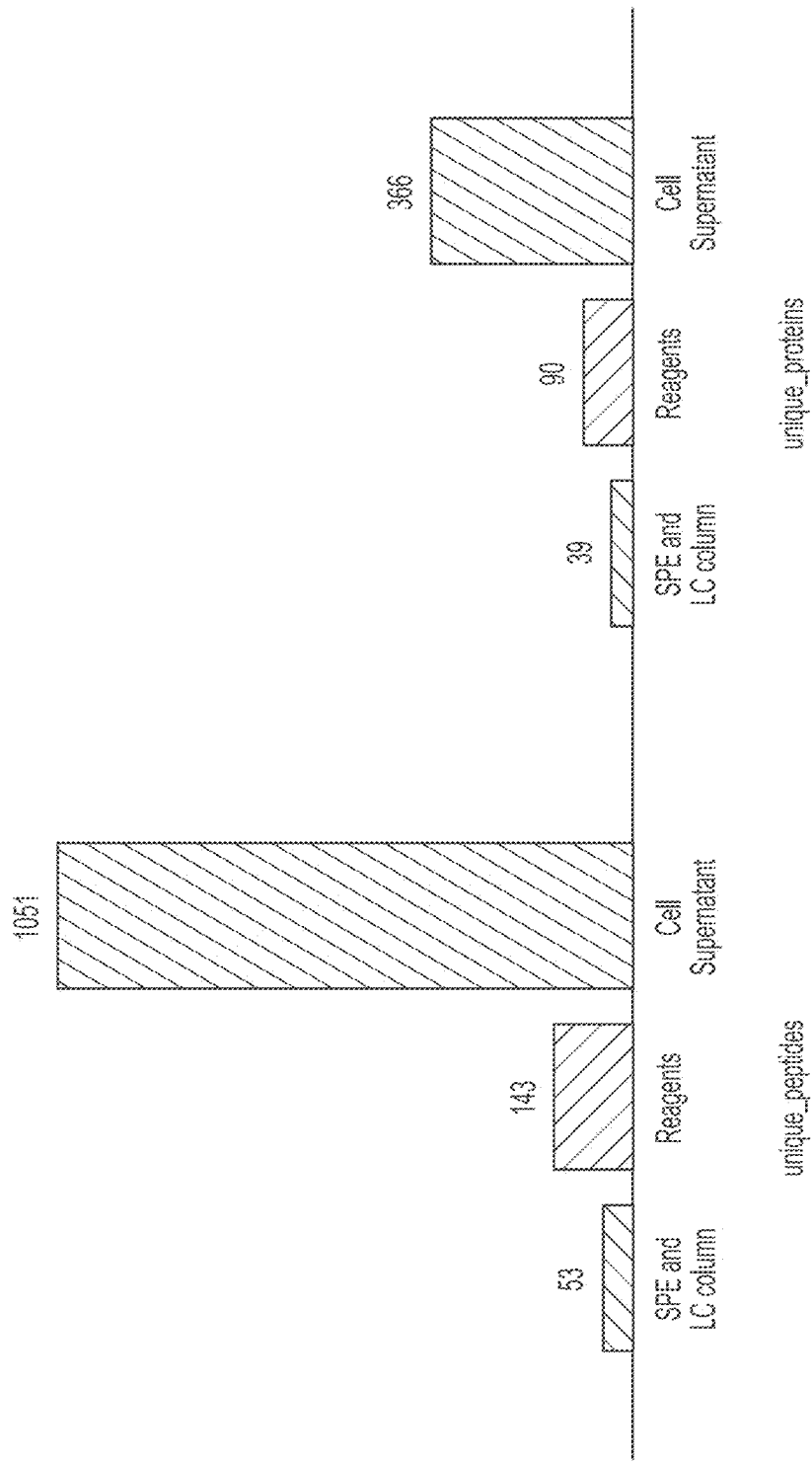
FIG. 15 presents bar graphs depicting peptide and protein identification from three blank control samples including solid phase extraction (SPE) and liquid chromatography (LC) columns, sample preparation reagents, and cell supernatant. To evaluate cross contamination from SPE and LC column, buffer A (e.g., storage buffer) was directly injected into SPE for LC-MS. To evaluate cross contamination from sample preparation reagents, PBS buffer instead of cells was dispensed into nanowells, followed by all proteomic processing steps, e.g., from FIGS. 5-7. To evaluate cross contamination from cell supernatant, cell suspension with a concentration of ~200 cell/μL was centrifuged at 2000 rpm for 10 min. The supernatant was dispensed into nanowells followed by all proteomic processing steps. All identification experiments were run after ~100-cell samples.
Figure 22:
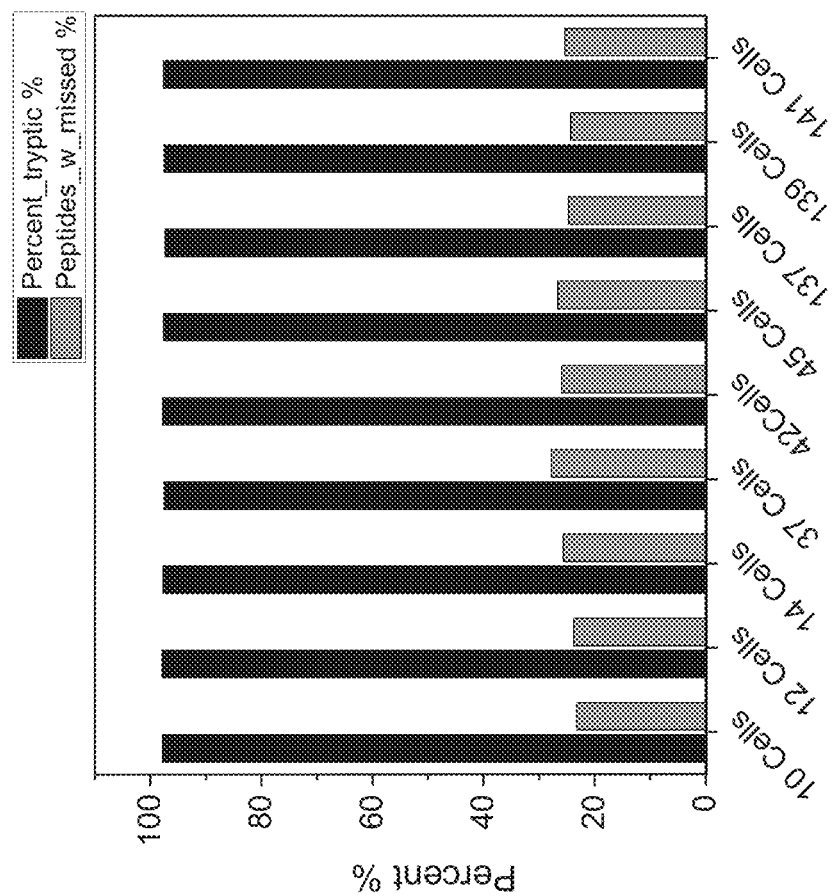
FIG. 22 depicts a bar graph depicting the evaluation of trypsin digestion efficiency. Percentages of full tryptic peptides and peptides with missed-cleavage sites for samples with cell numbers from 10 to 141.
Figure 23A:
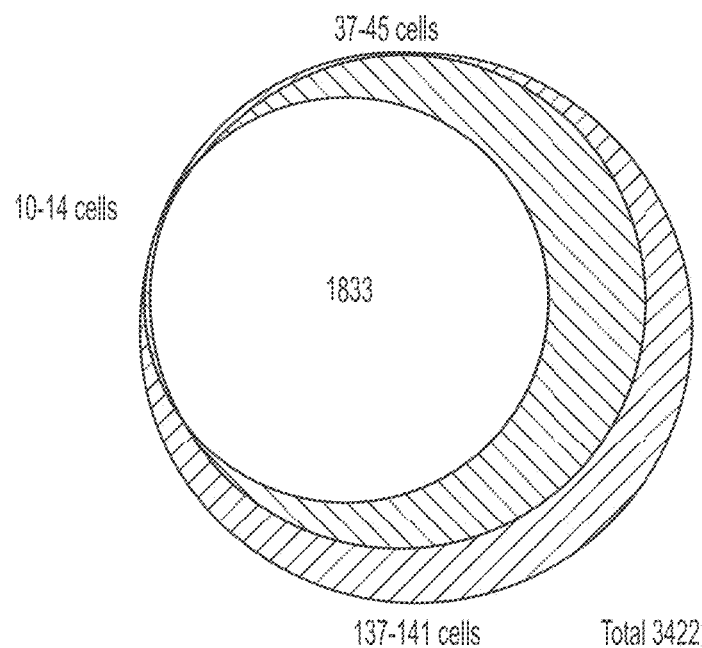
FIGS. 23A-23D depicts images of (a-b) overlap of identified protein groups from three cell loading groups with (FIG. 23A) MS/MS only method, and (FIG. 23B) combined MS/MS and MBR method.
Figure 23B:
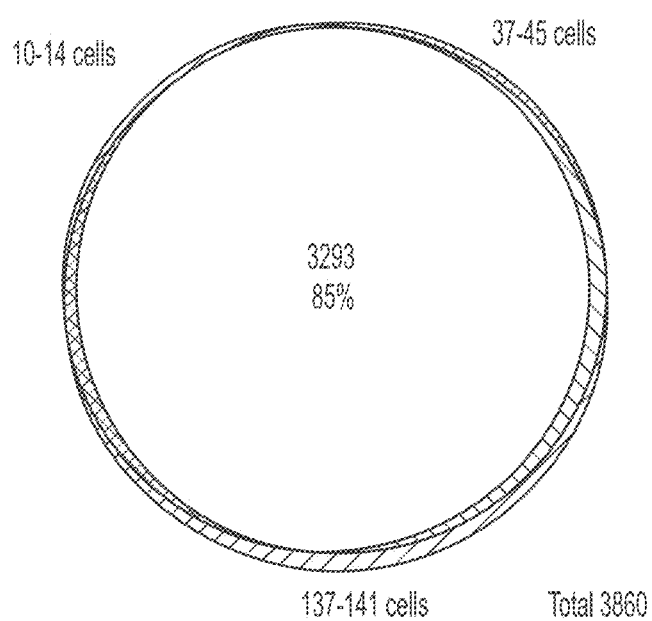
Figure 23C:
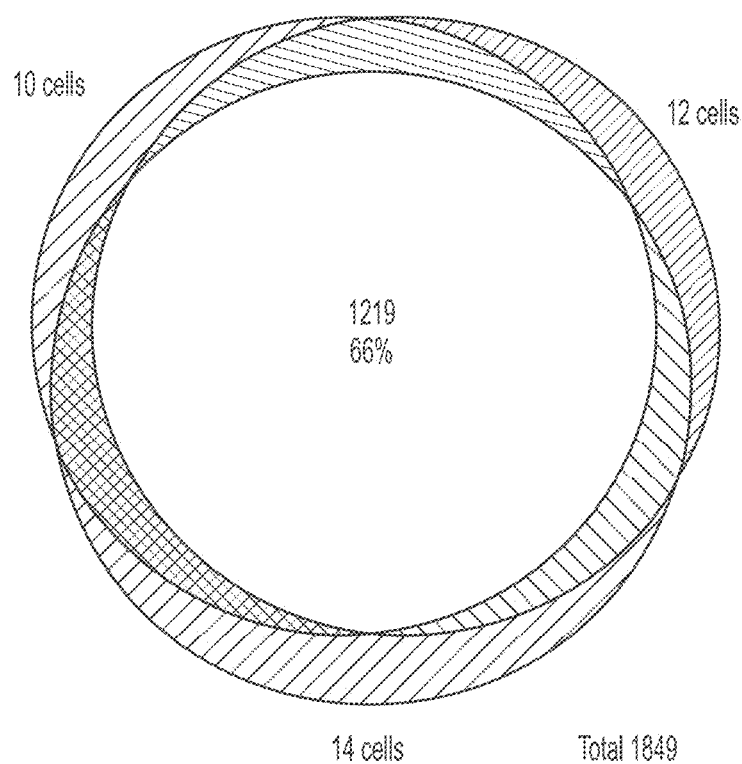
Figure 23D:
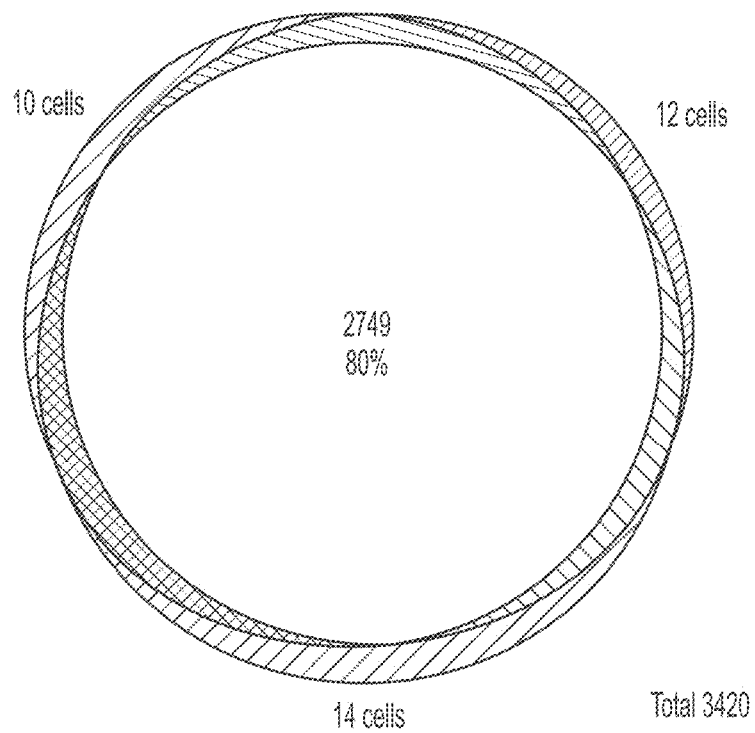

The sensitivity by processing 10-141 cultured HeLa cells with nanoPOTS (FIG. 1) was evaluated. Three different blank controls were used to confirm negligible carryover and contamination from the SPE and LC columns, reagents, and cell supernatant, respectively (FIG. 15). In contrast to the control samples, all cell-containing samples showed feature-rich base peak chromatogram profiles, and the number of peaks and their intensities increased with the number of cells (FIG. 13A-13C). The percentage of peptides having tryptic cleavage sites ranged from 97.4% to 97.9%, while the percentage of peptides having tryptic missed cleavage sites ranged from 23.2% to 27.8% (FIG. 22), indicating a digestion efficiency that is on par with conventional bulk processing (Wang, N. et al). The average peptide coverage based on MS/MS identification ranged from 7,364 to 17,836, and protein coverage ranged from 1,517 to 3,056 for triplicate groups comprising 10-14, 37-45 and 137-141 cells, respectively (FIGS. 14A and 14B). When the Match Between Runs (MBR) algorithm of Maxquant (Shen, Y et al.) was used, 85% of the identified proteins were found to be common to all samples (FIG. 24A-24C), indicating more proteins could likely be identified and quantified from the smaller samples if a larger reference library were used, or an appropriate accurate mass and time (AMT) tag database (Tyanova S, et al. 2016) were available. The ability to identify an average of 3,092 proteins in as small as ~10 cells (FIG. 24A-24C) represents a >500-fold decrease in sample size to achieve similar proteome coverage relative to previously reported methods (Sun, X et al, Chen, W et al., Wannders, L. et al, Huang, E. et al, and Wang, N. et al) (Table 1, below).

TABLE 1

Reported protein identification results with cell number lower than 2,000

| Cell # | Cell type | Identified protein # | Sample preparation method |
|---|---|---|---|
| 100 | DLD-1 | 635 | High temperature trypsin digestion[1] |
| 250 | DLD-1 | 759 | High temperature trypsin digestion[1] |
| 500 | DLD-1 | 1060 | High temperature trypsin digestion[1] |
|  | MCF-7 | 187 | Acetone precipitation[2] |
|  | Hela | 905 | FASP[3] |
| 1000 | MCF-7 | 271 | Acetone precipitation[2] |
|  | Hela | 1536 | FASP[3] |
| 2000 | HEK 239T | 1270 | Spin tip[4] |

To understand the absolute sensitivity of the nanoPOTS-LC-MS platform, the proteins were matched identified from 10-14 cells to the reported databases containing protein copy numbers per HeLa cell (Wisniewski, J. et al 2014, and Volpe, P. et al). In the first database, the absolute copy numbers of 40 proteins in HeLa cell were precisely quantified using spiked-in protein epitope signature tags (PrEST) in combination with SILAC-based isotopic labeling (Volpe, P. et al). Thirty-four of the 40 proteins were identified, and the 6 missed proteins were low in abundance. The corresponding protein copy number per cell ranged from about $5 \times 10^4$ to about $2 \times 10^7$ (Table 2), with 3 expressed at $<10^5$ copies/cell. Considering the highly reliable values obtained using the PrEST-SILAC method, the detection limit of nanoPOTS for protein is $<5 \times 10^5$ copies, or $<830$ zmol.

TABLE 2

Copy numbers per HeLa cell for proteins identified from 10-14 cells (copy number obtained from PrEST-SILAC method (Li, et al. and Zeiler, M. et al.).

| Protein Name | Gene Names | Protein copy number per HeLa cell |
|---|---|---|
| Pre-mRNA-splicing regulator WTAP | WTAP | 49,143 |
| ATPase family AAA domain-containing protein 2 | ATAD2 | 63,835 |
| Poly [ADP-ribose] polymerase 4 | PARP4 | 63,971 |
| Carbonyl reductase [NADPH] 3 | CBR3 | 79,823 |
| Endoplasmic reticulum lipid raft-associated protein 2 | ERLIN2 | 149,867 |
| THO complex subunit 1 | THOC1 | 204,962 |
| 28S ribosomal protein S23, mitochondrial | MRP S23 | 223,198 |
| Hepatocellular carcinoma-associated antigen 59 | C9orf78 | 265,003 |
| COP9 signalosome complex subunit 5 | COPS5 | 323,791 |
| Nucleoprotein TPR | TPR | 357,637 |
| AFG3-like protein 2 | AFG3L2 | 369,737 |
| 28S ribosomal protein S35, mitochondrial | MRP S28 | 422,825 |
| Prefoldin subunit 1 | PFDN1 | 476,849 |
| Cytosolic acyl coenzyme A thioester hydrolase | ACOT7 | 512,746 |
| Cytochrome b-c1 complex subunit 1, mitochondrial | UQCRC1 | 1,022,450 |
| 26S protease regulatory subunit 6A | PSMC3 | 1,062,048 |
| Eukaryotic translation initiation factor 3 subunit 6 | EIF3E | 1,067,627 |
| FACT complex subunit SSRP1 | SSRP1 | 1,095,695 |

TABLE 2-continued

Copy numbers per HeLa cell for proteins identified from 10-14 cells (copy number obtained from PrEST-SILAC method (Li, et al. and Zeiler, M. et al.).

| Protein Name | Gene Names | Protein copy number per HeLa cell |
|---|---|---|
| Ras GTPase-activating-like protein IQGAP1 | IQGAP1 | 1,296,511 |
| SRA stem-loop-interacting RNA-binding protein, | SLIRP | 1,397,500 |
| Purine nucleoside phosphorylase | PNP | 1,555,814 |
| Heat shock 70 kDa protein 4 | HSPA4 | 1,646,549 |
| 14-3-3 protein sigma | SFN | 1,870,568 |
| Flap endonuclease 1 | FEN1 | 2,019,699 |
| Enoyl-CoA hydratase, mitochondrial | ECHS1 | 2,105,336 |
| Transitional endoplasmic reticulum ATPase | VCP | 2,719,254 |
| Fatty acid synthase | FASN | 3,536,145 |
| T-complex protein 1 subunit beta | CCT2 | 4,479,130 |
| ATP synthase subunit beta, mitochondrial | ATP5B | 4,511,967 |
| Peroxiredoxin 6 | PRDX6 | 8,781,079 |
| Peptidyl-prolyl cis-trans isomerase B | PPIB | 10,502,199 |
| Vimentin | VIM | 22,886,339 |

Figure 16A:
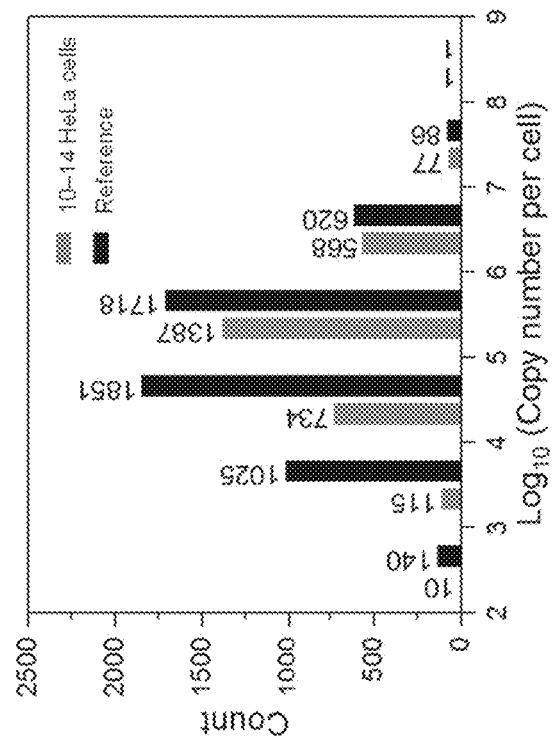
FIGS. 16A-16B are graphs depicting the distribution of copy number per cell for proteins identified from 10-14 HeLa cells by matching with previously-reported databases, containing 40 proteins obtained with PrEST-SILAC method (Tyanova et al.) (FIG. 16A), and 5443 proteins using the histone-based "proteomic ruler" method (FIG. 16B).
Figure 16B:
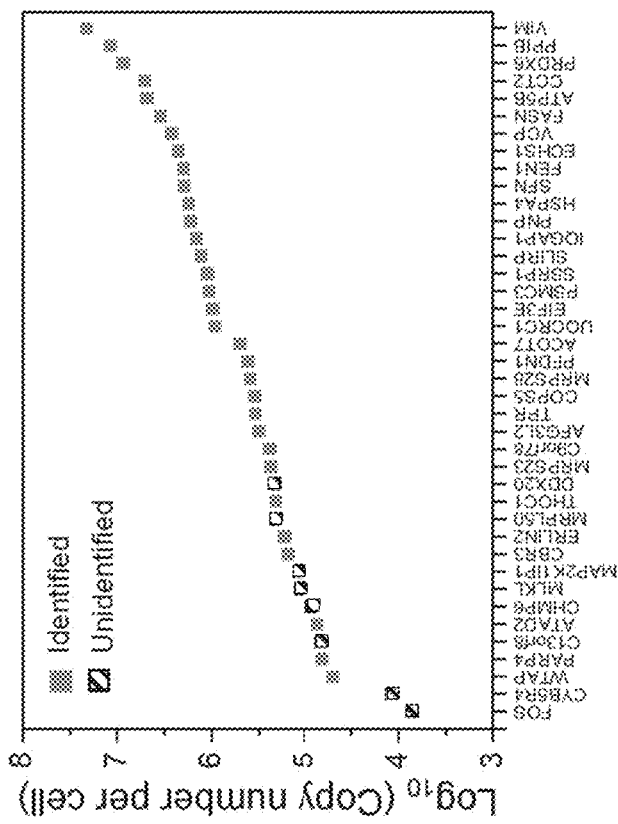

In the second database, a total of >5,000 proteins in HeLa cells were quantified using a histone-based 'proteomic ruler' and label-free quantitation based on MS intensities (Wisniewski, J. 2014). 2,892 of these proteins matched the proteins identified in the 10-14-cell samples, and the distribution of copy number per cell are shown in FIGS. 16A and 16B. The results are biased to high-abundance proteins due to the use of only ~10 cells. The median copy number within our samples was ~$2.5 \times 10^5$, which is approximately 4 times higher than the reference value (Wisniewski, J. et al 2014). Importantly, a number of low-abundance proteins were identified, including 125 proteins with copy numbers below 10,000 and 10 proteins below 1,000 (FIGS. 16A and 16B). These results indicate that the detection limit of the nanoPOTS-LC-MS platform may below 16 zmol. The results also show the great potential of the nanoPOTS platform for single cell proteomics with further improvement in sensitivity by optimizing processing volumes, miniaturizing the LC separation, and improving MS instrumentation.

Reproducibility and Quantitation

Figure 24A:
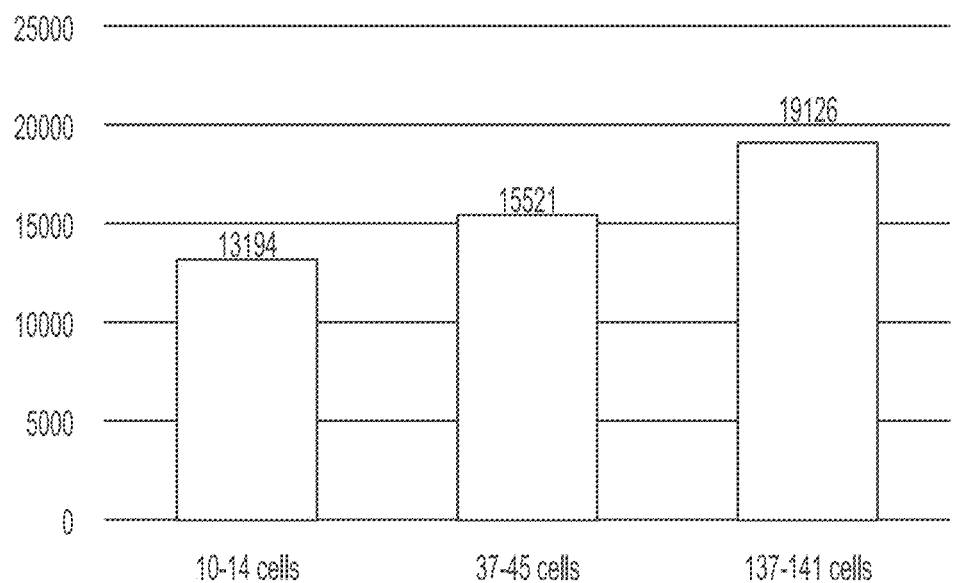
FIGS. 24A-24C are bar graphs depicting the quantifiable numbers of (FIG. 24A) peptide numbers and (FIG. 24B and FIG. 24C) protein group numbers for three cell loading groups. Peptides and proteins having intensities in all 3 samples with similar cell numbers were counted as quantifiable identifications.
Figure 24B:
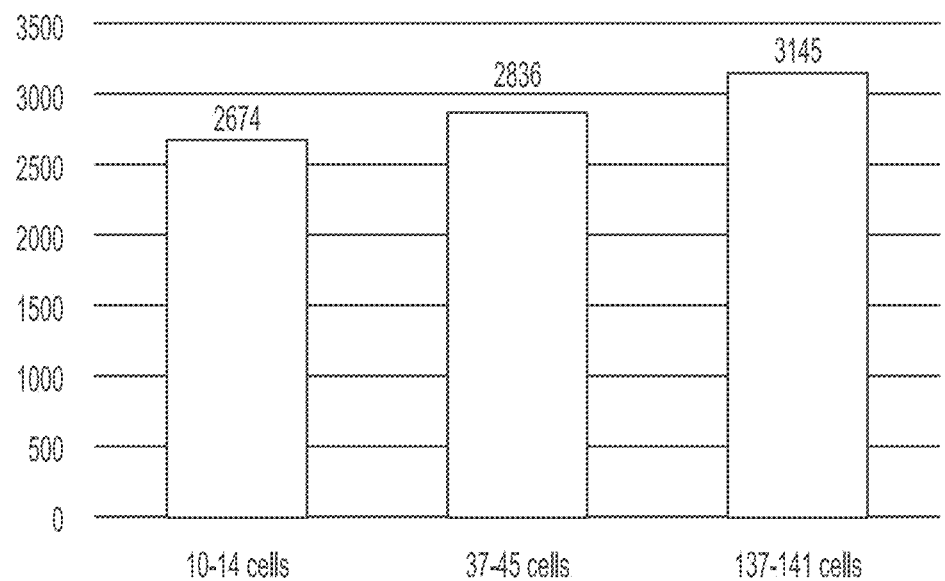
Figure 24C:
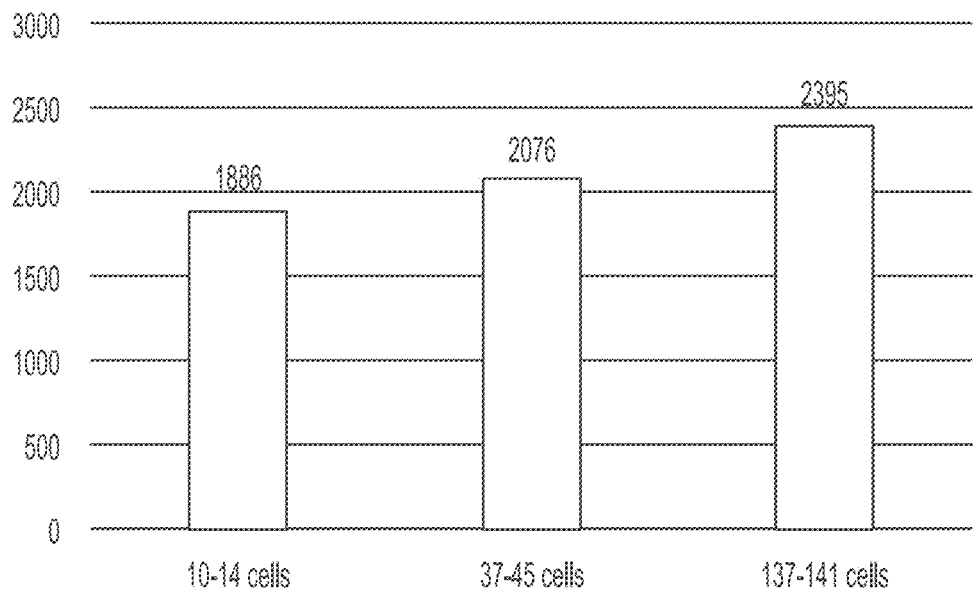
Figure 25A:
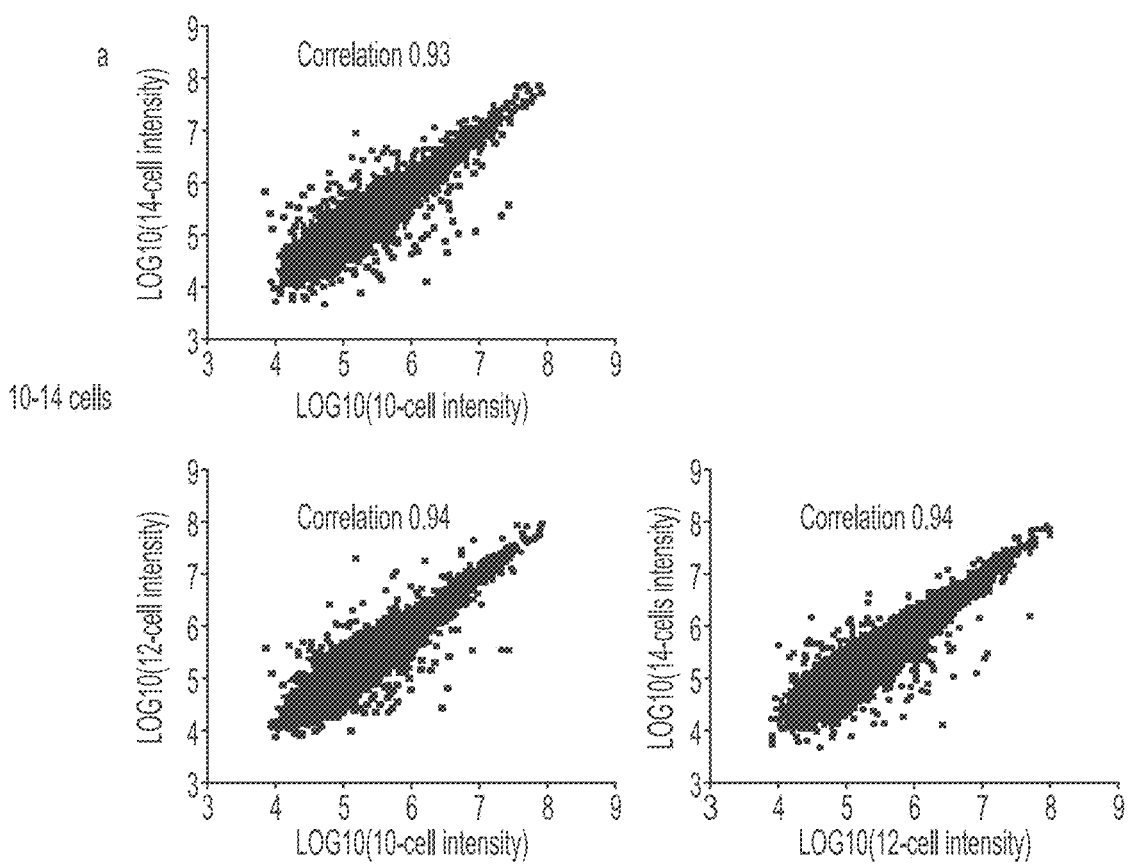
FIGS. 25A-25C depicts a pairwise correlation analysis of any two samples in peptide intensity level with cell loadings groups of (FIG. 25A) 10-14 cells, (FIG. 25B) 37-45 cells, and (FIG. 25C) 137-141 cells.
Figure 25B:
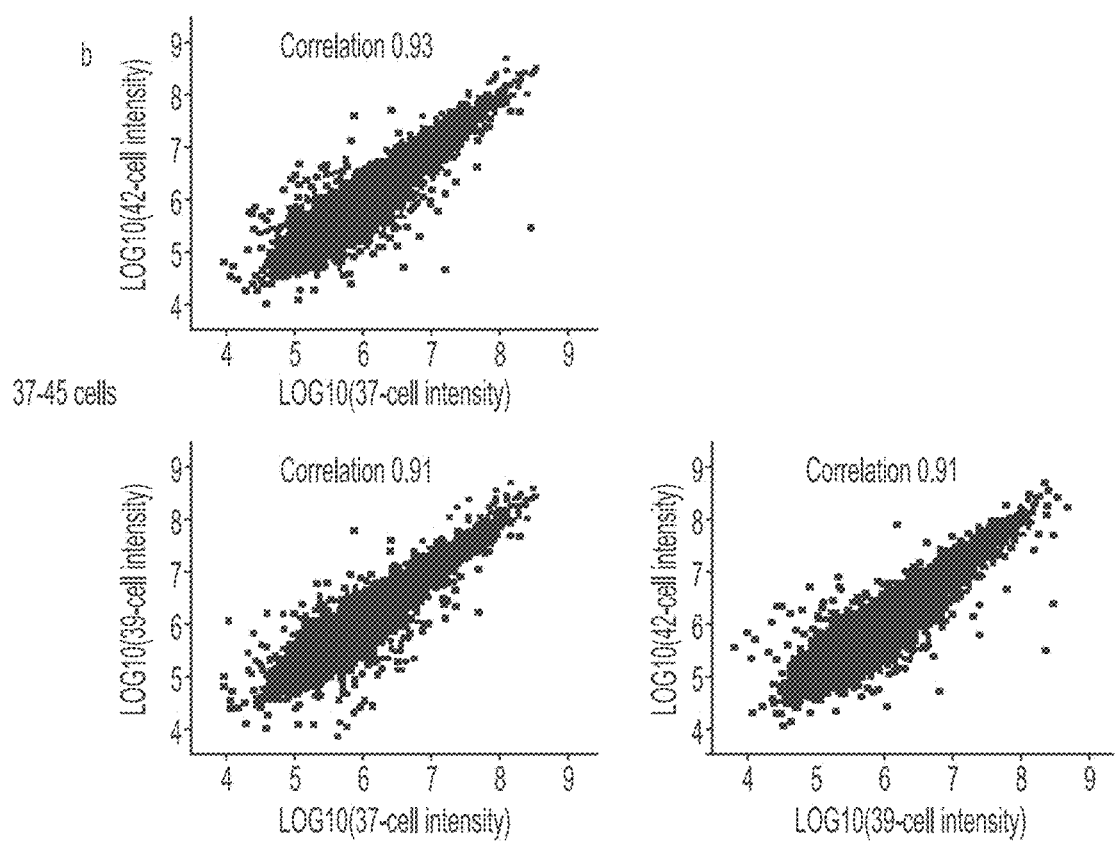
Figure 25C:
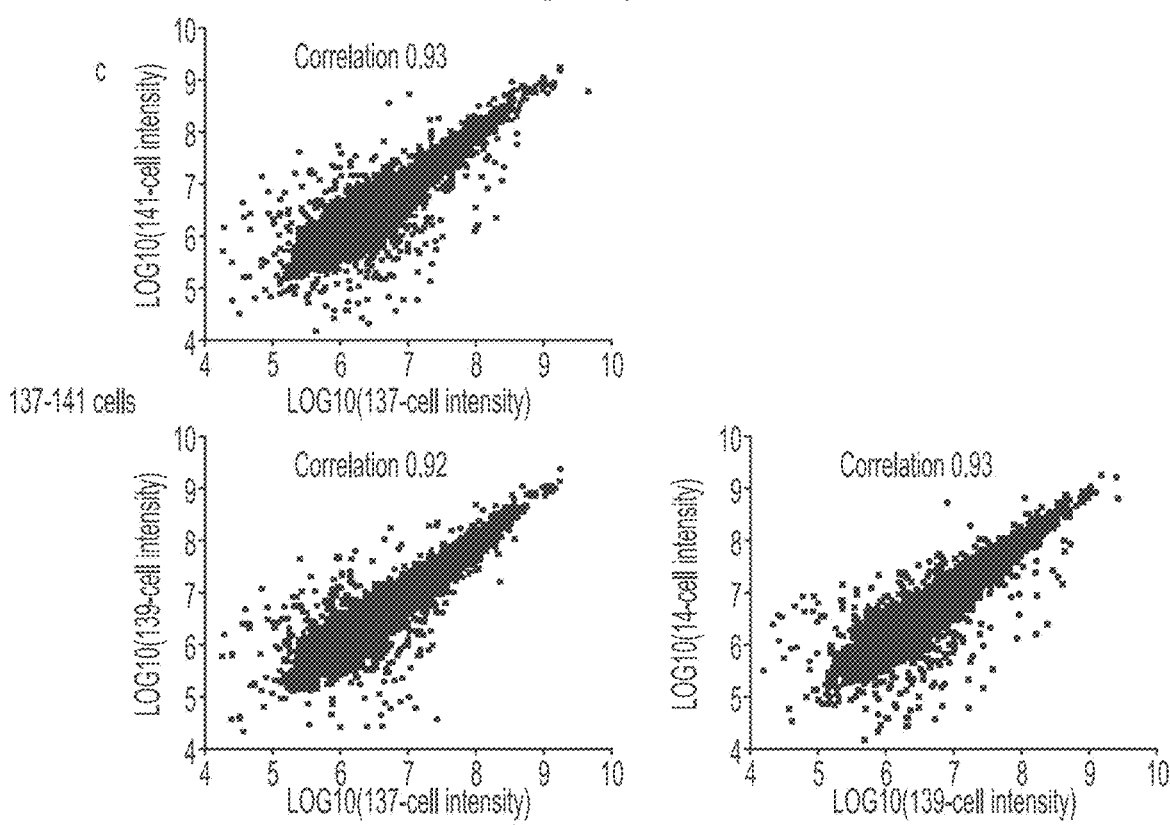
Figures 26A, 26B:
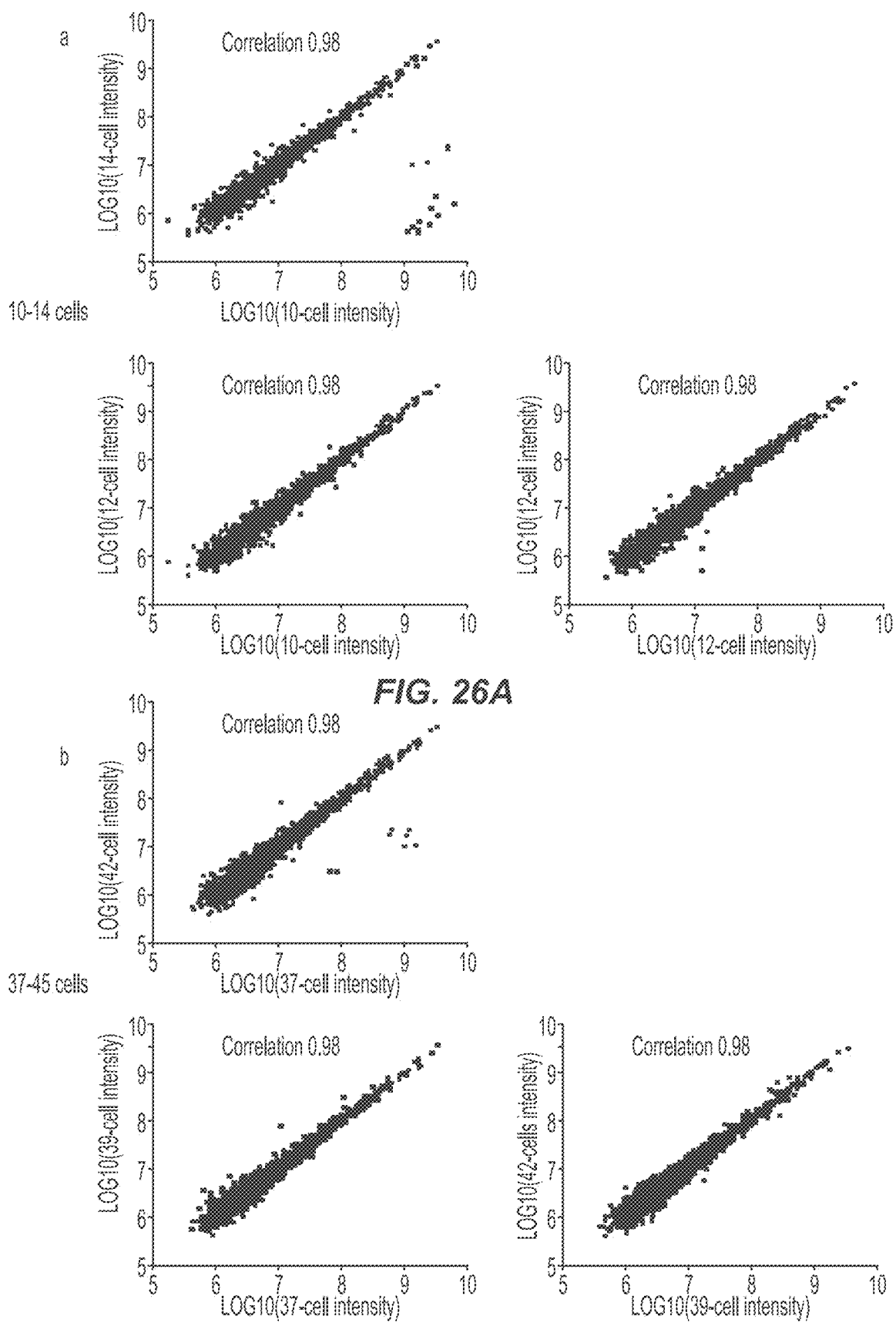
FIGS. 26A-26C depicts a pairwise correlation analysis of any two samples in protein intensity level with cell loadings groups of (FIG. 26A) 10-14 cells, (FIG. 26B) 37-45 cells, and (FIG. 26C) 137-141 cells. LFQ intensity generated from Maxquant was used for protein intensity calculation.
Figure 26C:
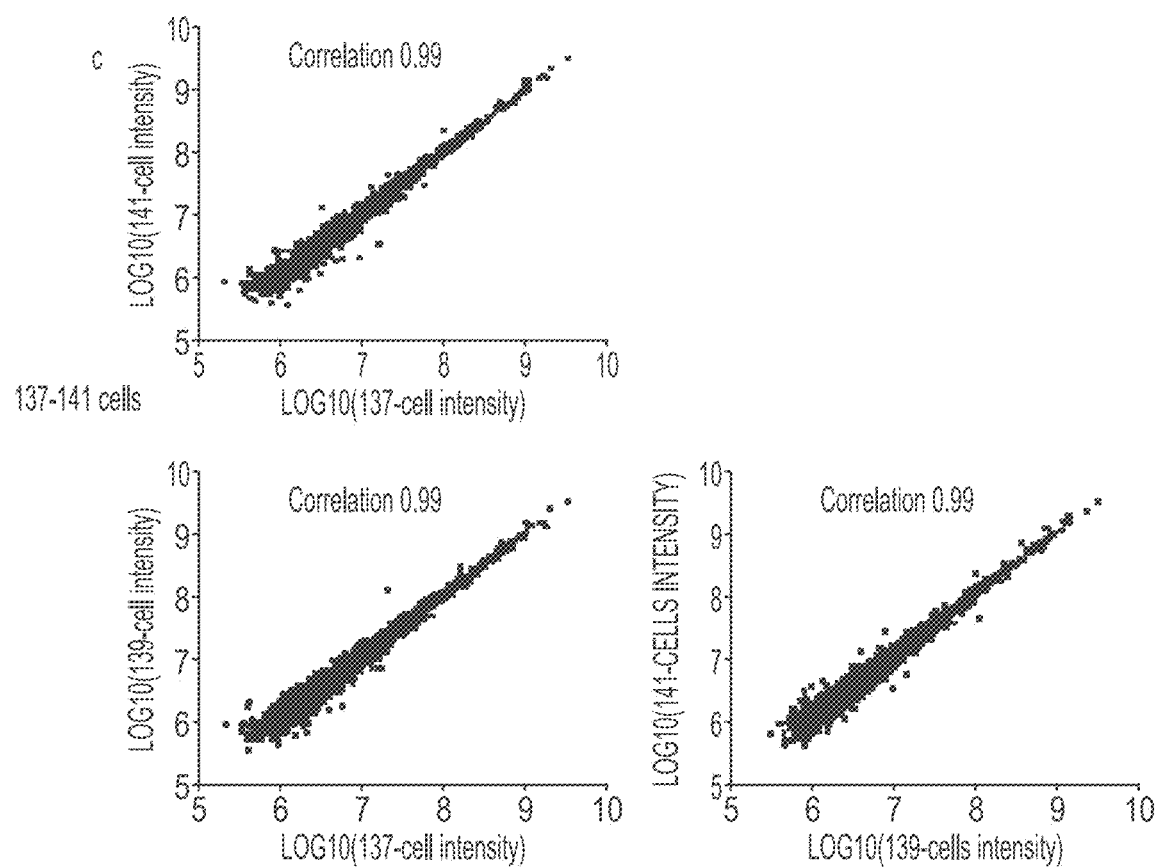

The reproducibility of nanoPOTS processing was evaluated using MS' intensity-based label-free quantification at both the peptide and the protein levels. The MBR analysis produced over 13,194 quantifiable peptides and 2,674 protein groups (FIG. 24A-24C). Median coefficients of variance (CVs) were ≤20.4% (peptide level) and 21.6% (protein level) for all the three cell loading groups (FIG. 17A-17D). Peptide and protein intensities spanning more than 4 orders of magnitude were observed (FIG. 17A-17D), indicating that dynamic range and proteome depth were substantially retained relative to bulk analyses. Pairwise analysis of any two samples with similar cell loadings showed Pearson correlation coefficients from 0.91 to 0.93 (FIG. 17A-17D) at the peptide level. Protein LFQ intensity revealed higher correlations with coefficients of 0.98 to 0.99 (FIG. 17A-17D). These data suggest that label-free quantification is feasible for far smaller proteomic samples than have been previously accessible.

Methods

Reagents and Chemicals:

Deionized water (18.2 MΩ) was purified using a Barnstead Nanopure Infinity system (Los Angeles, USA). Dithiothreitol (DTT) and iodoacetamide (IAA) were purchased from Thermo Scientific (St. Louis, USA) and freshly prepared in 50 mM ammonium bicarbonate buffer each day before use. RapiGest SF surfactant (Waters, Milford, USA) was dissolved in 50 mM ammonium bicarbonate buffer with a concentration 0.2% (m/m), aliquoted, and stored at −20° C. until use. Trypsin (MS grade) and Lys-C (MS grade) were products of Promega (Madison, USA). Other unmentioned reagents were obtained from Sigma-Aldrich (St. Louis, USA).

Fabrication and Assembly of the Nanowell Chip:

The photomask was designed with AutoCAD and printed with a direct-write lithography system (SF-100, Intelligent Micro Patterning LLC, St. Petersburg, USA). An array of 3×7 spots with diameters of 1 mm and a spacing of 4.5 mm was designed on a 25 mm×75 mm glass slide (soda lime) that was pre-coated with chromium and photoresist (Telic Company, Valencia, USA). After photoresist exposure (FIG. 3A), development, and chromium etching (Transene, Danvers, USA; FIG. 3B), the glass slide was hard baked at 110° C. for 10 min. The back side of the slide was protected with packing tape and the glass substrate surface was etched around the patterned photoresist/Cr features using wet etching solution containing 1 M HF, 0.5 M $NH_4F$, and 0.75 M $HNO_3$ at 40° C. for 10 min to reach a depth of 10 μm (FIG. 3C). The remaining photoresist was removed using AZ 400T stripper. The glass slide was thoroughly rinsed with water, dried using compressed nitrogen, and further dried in an oven at 120° C. for 2 h. The chip surface was then cleaned and activated with oxygen plasma treatment for 3 minutes using a March Plasma Systems PX250 (Concord, USA). The glass surface that was not protected with Cr was rendered hydrophobic with a fluorosilane solution containing 2% (v/v) heptadecafluoro-1,1,2,2-tetrahydrodecyl)dimethylchlorosilane (PFDS) in 2,2,4-trimethylpentane (FIG. 3D) for 30 min. The residual silane solution was removed by immersing the chip in 2,2,4-trimethylpentane followed by ethanol. Remaining chromium was removed using chromium etchant (Transene), leaving elevated hydrophilic nanowells on a hydrophobic background (FIG. 3E).

The glass spacer was fabricated by milling a standard microscope slide (25 mm×75 mm×1 mm) with a CNC machine (Minitech Machinery Corporation, Norcross, USA). Epoxy was used to glue the patterned chip and the glass spacer together. The glass cover was fabricated by spin coating a thin layer of polydimethylsiloxane (PDMS) membrane (10-μm thickness) onto a standard glass microscope slide of the same dimensions. Briefly, Dow Corning Sylgard 184 silicone base was mixed with its curing reagent at a ratio of 10:1 (w/w) and degassed for 20 min. The mixture was coated on the slide by spinning at 500 rpm for 30 s followed by 3000 rpm for 5 min (WS-650, Laurell Technologies, North Wales, USA). Finally, the PDMS membrane was cured at 70° C. for 10 hours. A piece of Parafilm (Bemis Company, Oshkosh, USA) was precisely cut to serve as moisture barrier between the glass spacer and the glass cover.

Nanoliter-Scale Liquid Handling System:

All sample and reagent solutions were delivered to the nanowells using a home-built liquid handling system with a metering precision of 0.3 nL. The liquid handling system is similar to those described previously (Zhu, Y. et al 2013, Zhu Y. et al 2015, and Zhu, Y. et al. 2014) and was composed of four parts including a 3D translation stage (SKR series, THK, Japan) for automated position control, a home-built high-precision syringe pump (KR series, THK, Japan) for liquid metering, a microscopic camera system (MQ013MG-ON, XIMEA Corp., Lakewood, USA) for monitoring the liquid handling process, and a tapered capillary probe for liquid dispensing. The capillary probe was fabricated by heating pulling a fused silica capillary (200 μm i.d., 360 μm o.d., Polymicro Technologies, Phoenix, USA) to generate a tapered tip (30 μm i.d., 50 μm o.d.). A home-built program with LabView (Version 2015, National Instruments, Austin, USA) was used to synchronously control the movement of the 3D stages and the liquid dispensing of the syringe pump. To minimize evaporation during the liquid handling procedure, the whole system was enclosed in a Lexan chamber maintained at 95% relative humidity.

The syringe pump was set at a withdraw rate of 9 μL/min and an infusion rate of 3 μL/min. The translation stages were operated at a start speed of 1 cm/s, a maximum speed of 30 cm/s, and an acceleration time of 0.5 s. In the typical setup, it took total ~2 min to dispense one reagent to all the 21 droplets in single chip including the time for withdrawing reagent into the capillary probe, moving of the robotic stages, and dispensing 50 nL reagent into each droplet.

To meet the requirement of processing large number of samples in single experiment, the nanowells can be scaled up with the present photolithography-based microfabrication technique. Up to 350 nanowells can be fabricated on a 25 mm×75 mm microscope slide and further scale-up is possible with larger substrates. The robot can be simply configured to fit different formats of nanowell array. Because of the high liquid handling speed, 350 droplets could be addressed in <30 min.

Cell Culture:

All cells were cultured at 37° C. and 5% $CO_2$ and split every 3 days following standard protocol. HeLa was grown in Eagle's Minimum Essential Medium (EMEM) supplemented with 10% fetal bovine serum (FBS) and 1× penicillin streptomycin.

Laser Capture Microdissection of Human Pancreatic Islets:

Ten-μm-thick pancreatic tissue slices were cut from OCT blocks using a cryo-microtome and mounted on PEN slides for islet dissection. Slides were briefly fixed with methanol, rinsed with $H_2O$ to remove OCT, and dehydrated using an alcohol gradient before placing in a desiccator to dry (8 minutes). Dehydrated and dried slides were placed on the stage of a laser microdissection microscope (Leica LMD7000). Islets were identified based on autofluorescence and morphology. Dissections were performed under a 10× objective. Laser dissected islets were collected in the cap of a 0.6-mL tube mounted underneath the slides. After dissection, samples were stored at −80° C. until further analysis.

Proteomic Sample Preparation in Eppendorf Low-Binding Vial:

HeLa cells were collected in a 10 mL tube and centrifuged at 1200 rpm for 10 minutes to remove culture media. The cell pellet was further washed three times with 10 mL of 1×PBS buffer. The cells were then suspended in 1 mL PBS buffer and counted to obtain cell concentration. Eppendorf protein low-binding vials (0.5 mL) were used throughout the process. Cells were lysed at a concentration of $5 \times 10^5$/mL in 0.1% RapiGest and 5 mM DTT in 50 mM ammonium bicarbonate (ABC). After heating at 70° C. for 30 min, the cell lysate was diluted in 50 mM ABC buffer and aliquoted to different vails with a volume of 5 μL. 5 μL of IAA solution (30 mM in 50 mM ABC) was dispensed to alkylate sulfhydryl groups by incubating the vials in the dark for 30 minutes at room temperature. 5 μL of Lys-C (0.25 ng in 50 mM ABC) was added and incubated at 37° C. for 4 h. 5 μL of Trypsin (0.25 ng in 50 mM ABC) was added and incubated overnight at 37° C. Finally, 5 μL of formic acid solution (30%, v/v) were dispensed and allowed to incubate for 1 h at room temperature to cleave RapiGest surfactant for downstream analysis.

Proteomic Sample Preparation in Nanodroplets:

Before use, the chip was washed with isopropanol and water to minimize contamination. The liquid handling system was configured to minimize cross contamination by adjusting the vertical distance between the probe tip and the nanowell surface, which was previously termed semi-contact dispensing (Zhu, Y. et al 2014).

For cultured cell samples, cells were collected in a 10 mL tube and centrifuged at 1200 rpm for 10 minutes to remove culture media. The cell pellet was further washed three times with 10 mL of 1×PBS buffer. The cells were then suspended in 1 mL PBS buffer and counted to obtain cell concentration. Cell concentrations were adjusted by serially diluting them in PBS to obtain different cell numbers in nanowells. After dispensing 50 nL of cell suspension into each nanowell, we observed that the distribution of cell numbers in nanowell was stochastic, especially for low-concentration cell suspensions. Thus, the accurate cell number in each nanowell was counted using an inverted microscope and indexed to the two-dimensional spatial position of the corresponding nanowell. For LCM tissues, a high precision tweezer with a tip of 20 μm (TerraUniversal, Buellton, USA) was used to transfer tissue pieces from collection tubes into individual nanowells under a stereomicroscope (SMZ1270, Nikon, Japan). ImageJ software[37] was used to measure the area of LCM islets to calculate islet equivalents (IEQ) and cell numbers.

For sample preparation of cultured cells, 50-nL RapiGest (Yu et al. 2003) (0.2%) solution with 10 mM DTT in 50 mM ammonium bicarbonate (ABC) was added into the nanodroplets that had been preloaded with cells. For LCM tissue samples, 100 nL of RapiGest solution (0.1% in 50 mM ABC) containing 5 mM DTT was added. The cover was then sealed to the nanodroplet chip, which was incubated in 70° C. for 30 min to achieve cell lysis, protein denaturation, and disulfide reduction. In the second step, 50 nL of IAA solution (30 mM in 50 mM ABC) was dispensed to alkylate sulfhydryl groups by incubating the chip in the dark for 30 minutes at room temperature. In the third step, 50 nL enzyme solution containing 0.25 ng Lys-C in 50 mM ABC was added and incubated at 37° C. for 4 h for predigestion. In the fourth step, 50 nL of enzyme solution containing 0.25 ng trypsin in 50 mM ABC was added into each droplet and incubated overnight at 37° C. for tryptic digestion. Finally, 50 nL of formic acid solution (30%, v/v) was dispensed and allowed to incubate for 1 h at room temperature to cleave RapiGest surfactant for downstream analysis. To minimize liquid evaporation in nanowells, the chip was completely sealed during cell counting, incubation, and transfer procedures. During each dispensing step, the chip was opened and closed within the humidity chamber to minimize droplet evaporation. However, as the total dispensed volume in each droplet was 300 nL, and the final volume was typically <200 nL, some evaporative losses clearly occurred. Some of these water losses were observed as condensation on the contactless cover upon cooling from the 70° C. protein extraction step, and the extended digestions at 37° C. also resulted in minor volume reductions. Such water losses have no negative effect on the performance of nanoPOTS platform, but could become limiting when further downscaling processing volumes.

Nanoliter-Volume Sample Collection and Storage:

Digested peptide samples in each nanowell were collected and stored in a section of fused silica capillary (5 cm long, 150 µm i.d., 360 µm o.d.). Before sample collection, the capillary was connected to the syringe pump and filled with water containing 0.1% formic acid (LC Buffer A) as carrier. A plug of air (10 nL, 0.5 mm in length) was aspirated into the front end of the capillary to separate sample from carrier. The capillary-to-nanowell distance was adjusted to ~20 µm to allow majority of sample to be aspirated into the capillary. To achieve highest sample recovery, the nanowell was twice washed with 200-nL buffer A and the wash solutions were also collected in the same capillary. A section of capillary containing a train of plugs consisting of carrier, air bubble, sample, and wash solutions was then cut from the syringe pump. The capillary section was sealed with Parafilm at both ends and stored at −20° C. for short-term storage or −70° C. for long-term storage.

SPE-LC-MS Setup:

The SPE precolumn and LC column were slurry-packed with 3-µm C18 packing material (300-Å pore size, Phenomenex, Terrence, USA) as described previously (Shen, Y. et al 2004, and Shen, Y. et al. 2003). The SPE column was prepared from a 4-cm-long fused silica capillary (100 µm i.d., 360 µm o.d., Polymicro Technologies, Phoenix, Ariz.). The LC column was prepared from a 70-cm Self-Pack PicoFrit column with an i.d. of 30 µm and a tip size of 10 µm (New Objective, Woburn, USA). The sample storage capillary was connected to the SPE column with a PEEK union (Valco instruments, Houston, USA). Sample was loaded and desalted in the SPE precolumn by infusing buffer A (0.1% formic acid in water) at a flow rate of 500 nL/min for 20 minutes with an nanoACQUITY UPLC pump (Waters, Milford, USA). The SPE precolumn was reconnected to the LC column with a low-dead-volume PEEK union (Valco, Houston, USA). The LC separation flow rate was 60 nL/min, which was split from 400 nL/min with a nanoACQUITY UPLC pump (Waters, Milford, USA). A linear 150-min gradient of 5-28% buffer B (0.1% formic acid in acetonitrile) was used for separation. The LC column was washed by ramping buffer B to 80% in 20 minutes, and finally re-equilibrated with buffer A for another 20 minutes.

An Obitrap Fusion Lumos Tribrid MS (ThermoFisher) was employed for all data collection. Electrospray voltage of 1.9 kV was applied at the source. The ion transfer tube was set at 150° C. for desolvation. S-lens RF level was set at 30. A full MS scan range of 375-1575 and Obitrap resolution of 120,000 (at m/z 200) was used for all samples. The AGC target and maximum injection time were set as 1E6 and 246 ms. Data-dependent acquisition (DDA) mode was used to trigger precursor isolation and sequencing. Precursor ions with charges of +2 to +7 were isolated with an m/z window of 2 and fragmented by high energy dissociation (HCD) with a collision energy of 28%. The signal intensity threshold was set at 6000. To minimize repeated sequencing, dynamic exclusion with duration of 90 s and mass tolerance of ±10 ppm was utilized. MS/MS scans were performed in the Obitrap. The AGC target was fixed at 1E5. For different sample inputs, different scan resolutions and injection times were used to maximize sensitivity (240 k and 502 ms for blank control and ~10-cell samples; 120 k and 246 ms for ~40-cell samples; 60 k and 118 ms for ~140-cell samples).

Data Analysis:

All raw files were processed using Maxquant (version 1.5.3.30) for feature detection, database searching and protein/peptide quantification (Tyanova, S. et al 2016). MS/MS spectra were searched against the UniProtKB/Swiss-Prot human database (Downloaded in Dec. 29, 2016 containing 20,129 reviewed sequences). N-terminal protein acetylation and methionine oxidation were selected as variable modifications. Carbamidomethylation of cysteine residues was set as a fixed modification. The peptide mass tolerances of the first search and main search (recalibrated) were <20 and 4.5 ppm, respectively. The match tolerance, de novo tolerance, and deisotoping tolerance for MS/MS search were 20, 10, and 7 ppm, respectively. The minimum peptide length was 7 amino acids and maximum peptide mass was 4600 Da. The allowed missed cleavages for each peptide was 2. The second peptide search was activated to identify co-eluting and co-fragmented peptides from one MS/MS spectrum. Both peptides and proteins were filtered with a maximum false discovery rate (FDR) of 0.01. The Match Between Runs feature, with a match window of 0.7 min and alignment window of 20 min, was activated to increase peptide/protein identification of low-cell-number samples. LFQ calculations were performed separately in each parameter group that containing similar cell loading. Both unique and razor peptides were selected for protein quantification. Requiring MS/MS for LFQ comparisons was not activated to increase the quantifiable proteins in low-cell-number samples. Other unmentioned parameters were the default settings of the Maxquant software.

Perseus (Tyanova, S. et al. 2016) was used to perform data analysis and extraction. To identify the significantly changed proteins from a non-diabetic donor and a T1D donor, the datasets were filtered to contain 3 valid LFQ intensity values in at least one group. The missing values were imputed from normal distribution with a width of 0.3 and a down shift of 1.8. Two sample T-test with a minimal fold change of 2 and a FDR of 0.01 was performed for statistical analysis. The extracted data were further processed and visualized with OriginLab 2017. Global scaling normalization was achieved using scaling coefficients calculated as the ratio of peptide abundance to the median peptide abundance measured for each loading set. Coefficients of variation were calculated by dividing the standard deviation of normalized intensities by the mean intensity across the datasets of similar loading. The Violin plot was generated with an online tool (BoxPlotR, http://shiny.chemgrid.org/boxplotr/) (Spitzer, M. et al).

nanoPOTS Platform Results and Conclusions

The nanoPOTS platform provided a robust, semi-automated nanodroplet-based proteomic processing system for handling extremely small biological samples down to as few as 10 cells with high processing efficiency and minimal sample loss. This capability opens up many potential biomedical applications from small cell populations and clinical specimens such as tissue sections for characterizing tissue or cellular heterogeneity. Reproducible quantitative proteome measurements with coverage of 2000-3,000 protein groups from as few as 10 mammalian cells or single human islet cross sections (~100 cells) from clinical specimens were demonstrated. While several previous efforts have pursued the analysis of <2000 cells, most of these methods lacked the robustness and reproducibility for biological applications because of the highly manual processes involved (Li, S. et al 2015, Chen, Q. et al 2015, Chen, W. et al. 2016, and Waanders, L. et al). The nanoPOTS platform not only provided unparalleled proteome coverage for analyzing 10-100 cells, but also offered a number of technical advantages for achieving a high degree of robustness and reproducibility for high throughput processing and quantitative measurements when coupled with LC-MS. First, the platform effectively addressed the bottleneck of sample losses during proteomics sample preparation by performing all of the multi-step reactions within a single nanodroplet of <200 nL volume, while all previous methods still suffer from a significant degree of protein/peptide losses during processing. Second, the nanodroplet processing mechanism allowed us to perform each reaction at optimal concentrations. For example, by preserving the 20-50:1 ratio (Vandermarlier, E. et al) of protein to protease within the nanodroplet, the digestion rate and efficiency is potentially increased by orders of magnitude relative to a standard-volume preparation for the same number of cells. Finally, in addition to label-free quantification, other stable isotope-based quantification methods are readily adaptable to the workflow.

Compared with other microfluidic platforms having closed microchannels and chambers (White, A. et al. 2011, and Zhu, Y. et al. 2010), the nanoPOTS has an open structure, which is inherently suitable for integration with upstream and downstream proteomic workflows, including sample isolation for processing and transfer for LC-MS analysis.

Figure 19:
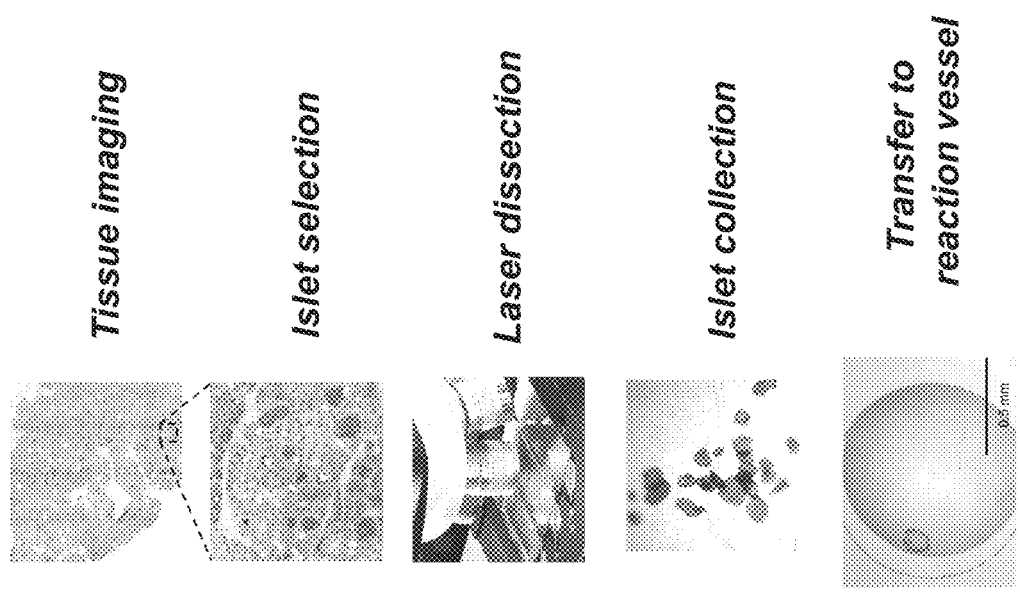
FIG. 19 depicts a schematic showing the workflow of the isolation of laser microdissected of human pancreatic islets into nanowells.

Laser Microdissected Samples—Profiling of Protein Expression in Thin Sections of Human Islets To further explore potential applications involving characterization of substructures or molecular phenotyping of heterogeneous tissues such as human pancreas, the method was used to analyze cross-sections of individual human islets having a thickness of 10 µm (FIG. 19) that were isolated by laser microdissection from clinical pancreatic specimens (FIG. 18A-18D). The islet equivalents (IEQ) were calculated to be from 0.06 to 0.17, corresponding to approximately 91 to 266 cells based on their volumes and a previous quantitative study (Zeiler, M. et al.) (Table 3).

TABLE 3

Calculation of cell number and islet equivalents with islet areas (Pisania, A. et al 2010).

| | Islet Area ($\mu m^2$) | Islet volume ($\mu m^3$) | Cell Number | Islet equivalents (IEQ) |
|---|---|---|---|---|
| No1 | 30197 | 301973 | 266 | 0.17 |
| No2 | 16200 | 162004 | 143 | 0.09 |
| No3 | 21286 | 212862 | 188 | 0.12 |
| No4 | 11133 | 111330 | 98 | 0.06 |
| No5 | 14235 | 142354 | 125 | 0.08 |
| No6 | 22428 | 224280 | 198 | 0.13 |
| No7 | 10365 | 103654 | 91 | 0.06 |
| No8 | 15186 | 151860 | 134 | 0.09 |
| No9 | 21474 | 214738 | 189 | 0.12 |

Figure 20A:
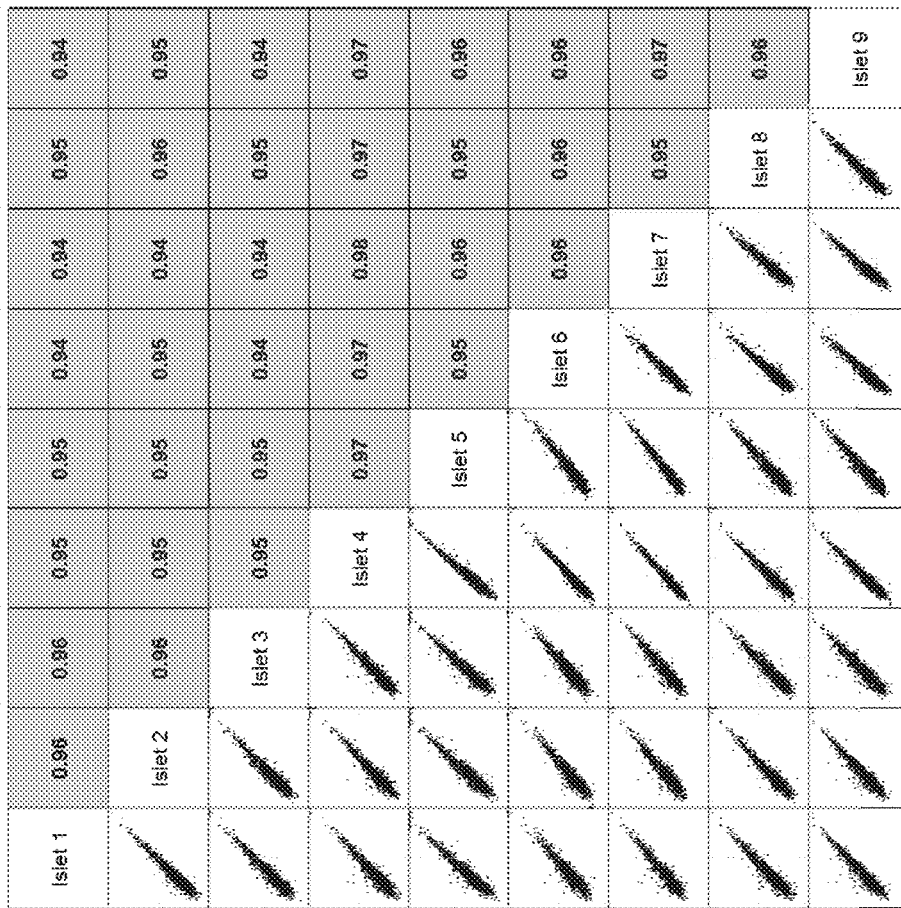
FIG. 20A depicts images showing the pairwise correlation analysis of protein expression level in nine human islet slices.
Figure 20B:
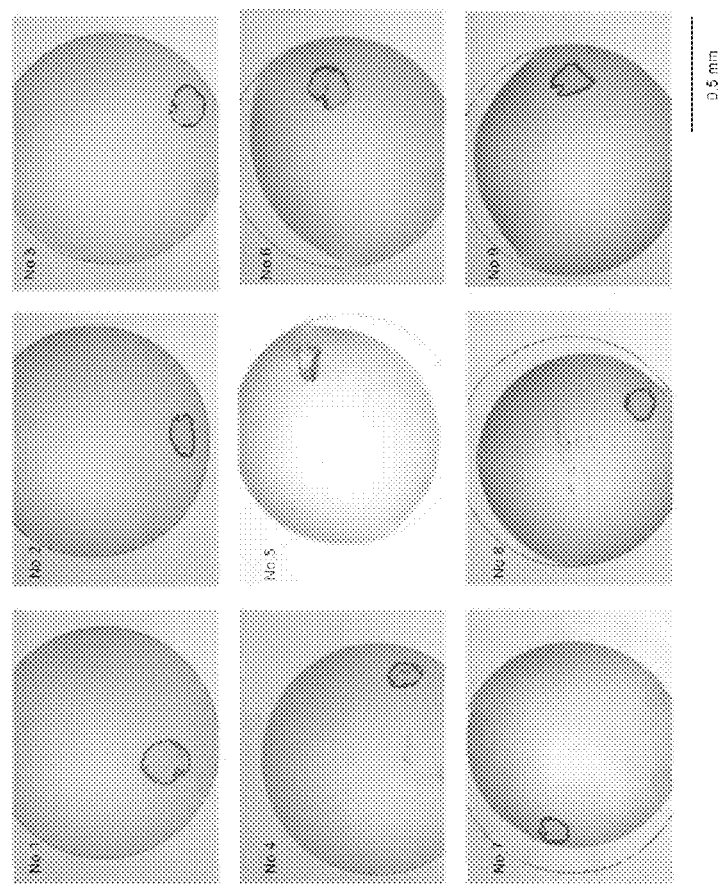
FIG. 20B depicts images of the nine islet sections used as described herein.
Figure 21:
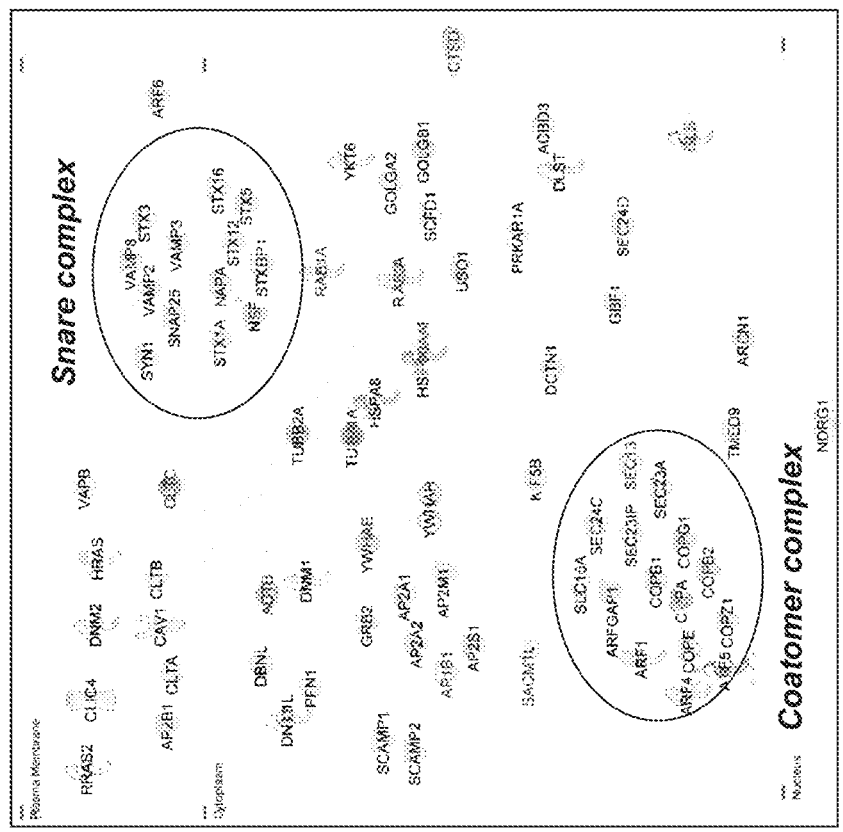
FIG. 21 depicts an image showing the protein coverage of a network involved in vesicular transport.
Figure 27:
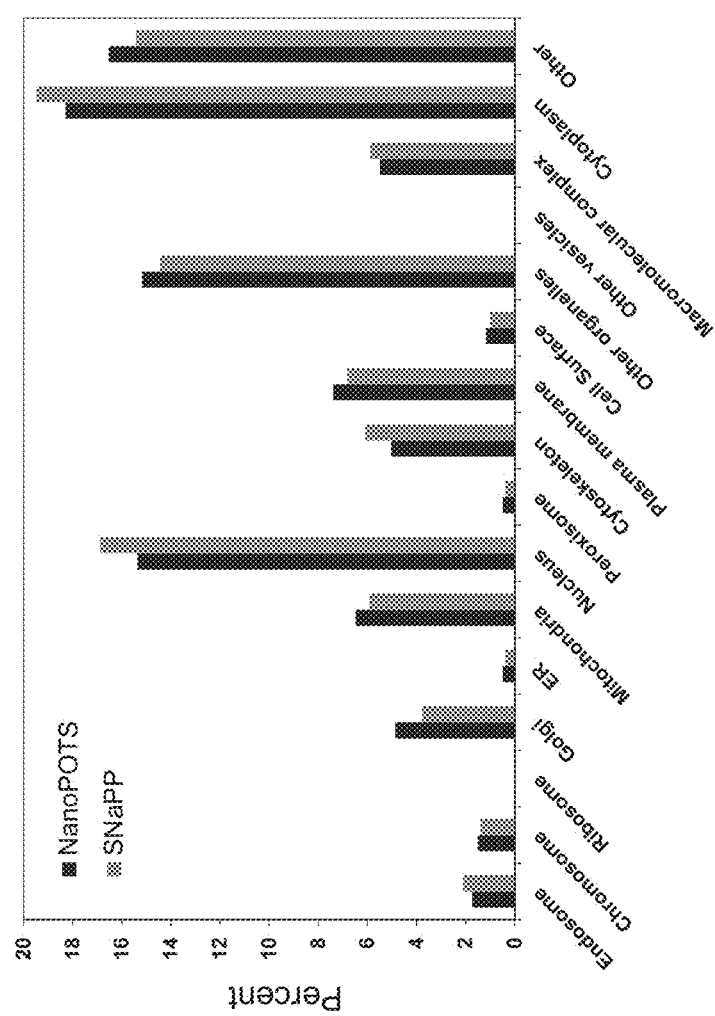
FIG. 27 is a bar graph depicting the comparison of Gene Ontology annotations for Cellular Component showing the protein identified from nanoPOTS and SNaPP platforms (Sun, L. et al.). In nanoPOTS platform, datasets were generated 9 slices of LCM islets. In SNaPP platform, datasets were generated from triplicate runs of more than 100 islets.
Figure 28:
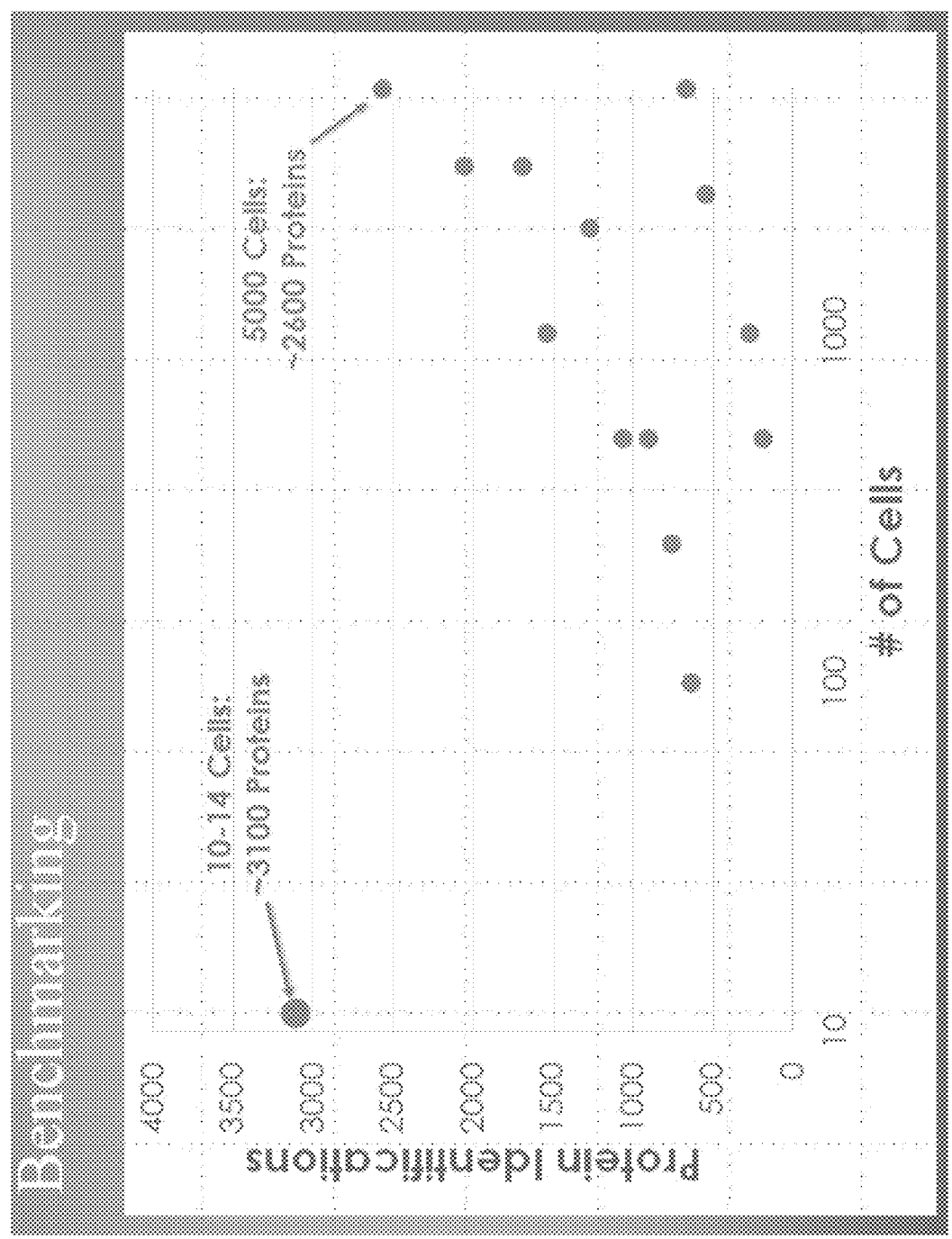
FIG. 28 depicts a graph showing the number of proteins identified versus the number of mammalian cells for previously published platforms (blue) and the present platform (red), indicating that the present platform has achieved greater proteome coverage from just 10-14 cells than was achieved previously from much larger samples.

An average of 2,511 and a total of 2,834 protein groups were identified for the nine single islet slices; 2,306 protein groups were quantifiable with valid intensities and >2 unique peptides in 5 out of 9 samples. The protein group identifications exceed those of previously reported single intact islets (Huang, E. et al 2016). Pairwise correlation analysis of protein LFQ intensity resulted in coefficients ranging from 0.93 to 0.97 (FIGS. 20A and 20B), indicating a degree of islet heterogeneity. Gene Ontology analysis indicated that the proteome data provided coverage of cellular compartments similar to bulk analyses (FIG. 27), demonstrating the nanoPOTS avoid biases in protein extraction from different compartments. FIG. 21 further illustrated the coverage of a network of proteins involved in vesicular transport, including the SNARE and Coatomer complex (Clair, G. et al.), an important function for secreting islet cells. This initial study indicates nanoPOTS will specifically enable studies of single islet heterogeneity using clinical specimens to explore islet pathology of type 1 or type 2 diabetes (Pisania, A. et al.), and more broadly enable clinical analysis of many otherwise inaccessible samples.

Currently, there is no residue/adhesive-free method available to transfer samples from LMD to small-volume reactor vessel for effective sample preparation of small samples. This method is broadly applicable and transferrable in the fields of proteomics, metabolomics, lipidomics, peptidomics, genomics, transcriptomics, etc., as analysis of small samples isolated by LMD is limited by interference of the adhesive capture material and by the large volumes require by the process.

Example 2: nanoPOTS Interface with FACS

Additionally, experiments showed that the nanoPOTS chip directly interfaced with fluorescence-activated cell sorting (FACS) for cell isolation. With the photolithography-based microfabrication technique, the nanodroplet array size and density can be easily scaled for increased preparation throughput.

While the current demonstrated limit is to analyze of as few as 10 cells, nanoPOTS represented a highly promising platform towards single mammalian cell proteomics with optimized processing volumes and further refinements to the LC-MS platform. To maximize the overall sensitivity of nanoPOTS for single cells, the total processing volume could be reduced to the low-nanoliter range to further minimize sample loss. FACS or other cell isolation techniques should be used to isolate single cells into nanowells without the minimal exogenous contamination from, e.g., secreted proteins or lysed cells. NanoLC columns with narrower bore (Shen, Y. et al. 2004, and Shen, Y. 2003), and ESI emitter technology accommodating the lower resulting flow rates (Smit, R. et al.) could be employed to improve the detection sensitivity of the LC-MS system. Finally, in addition to single cell analysis, nanoPOTS should also provide a viable path towards tissue imaging at the proteome level by performing in-depth spatially resolved proteome measurements for specific cellular regions.

Example 3: nanoPOTS with LCM and Capture Liquid

Nanowells are prepopulated with DMSO droplets to serve as a sacrificial capture medium for small tissue samples in the nanoPOTS chip (FIGS. 29A-29E) as described below in detail.

Reagents and chemicals. Deionized water (18.2 MΩ) generated from a Barnstead Nanopure Infinity system (Los Angeles, Calif.) was used throughout. Dithiothreitol (DTT) and iodoacetamide (IAA) were from ThermoFisher Scientific (St. Louis, Mo.), and their working solutions were freshly prepared in 50 mM ammonium bicarbonate buffer before use. n-dodecyl-β-D-maltoside (DDM), Mayer's hematoxylin, eosin Y (alcoholic solution), Scott's Tap Water Substitute, DMSO were purchased from Sigma-Aldrich. Trypsin (MS grade) and Lys-C (MS grade) were from Promega (Madison, Wis.). Other unmentioned reagents were obtained from ThermoFisher.

Nanowell chip fabrication. The nanowell chip consisted of three parts including a nanowell-containing substrate, a spacer, and a cover plate. The nanowell substrate was fabricated with the similar procedures described previously. (Liu, Anal. Chem. 2017, 89(1), 822-829; Zhu, Anal. Chem. 2010, 82 (19), 8361-8366) Briefly, a glass slide (25 mm×75 mm) with pre-coated chromium and photoresist (Telic company, Valencia, Calif.) was used as starting material. Standard photolithography and wet etching procedures were employed to generate an array of pedestals with a diameter of 1.2 mm, a height of 10 μm, and a spacing of 4.5 mm between adjacent pedestals on the slide. The exposed surfaces surrounding the pedestals were treated to be hydrophobic with 2% (v/v) heptadecafluoro-1,1,2,2-tetrahydrodecyl)dimethylchlorosilane (PFDS) (Sigma Aldrich) in 2,2, 4-trimethylpentane. After removing the chromium layer, the pedestals maintained the hydrophilicity of untreated glass and served as nanoliter-scale wells for tissue collection and proteomic sample processing. The glass spacer was laser-machined (Coherent Inc., Santa Clara, Calif.) on a standard 1.2-mm-thick microscope slide. The machining process removed the center region of the slide, leaving a thin frame of ~5 mm in width. The machined slide was glued to the nanowell substrate using a silicone adhesive, and served as a spacer to limit the headspace of the nanowells after reversibly sealing to a cover plate to minimize evaporation during incubation steps, while prevent contact of the droplet reactors with the cover plate. The cover plate was produced by spin coating of a thin layer of Sylgard 184 and its curing reagent (10/1, v/v) (Dow Corning) at a spin speed of 500 rpm for 30 s followed by 3000 rpm for 5 min. The cover plate was baked at 70° C. for 10 hours to generate a ~30-μm-thick polydimethylsiloxane (PDMS) layer.

Tissue preparation. Rats were anesthetized by intra-peritoneal injection of chloral hydrate. Rat brain was dissected and snap frozen in liquid nitrogen. The brains were stored at −80° C. until use. A cryostat (NX-70, Thermo Scientific, St. Louis, Mo.) was used to cut tissues to a thickness of 12 μm. The chuck and blade temperatures were set as −16° C. and −20° C., respectively. The tissue sections were deposited on PEN membrane slides (Carl Zeiss Microscopy, Germany) and stored at −80° C.

Before the hematoxylin and eosin (H&E) staining procedures, the tissue section was removed from the freezer or dry ice box and immediately immersed into 70% ethanol to fix proteins. The tissue was then rehydrated in deionized water for 30 s and stained in Mayer's hematoxylin solution for 1 min. Excess dye was rinsed with water and the tissue was blued in Scott's Tap Water Substitute for 15 s. Next, 70% ethanol was used to dehydrate the tissue and a 50% dilution of eosin Y solution (v/v in ethanol) was applied for 1-2 s by a quick dip. The tissue sample was further dehydrated by immersion twice in 95% ethanol for 30 s, twice in 100% ethanol for 30 s, and finally in xylene for 2 min. All the procedures were performed in a fume hood and the slide was blotted on absorbent paper between different solutions to minimize carry over. The processed tissue could be directly used for LCM or stored at −80° C. until use.

Figure 29A:
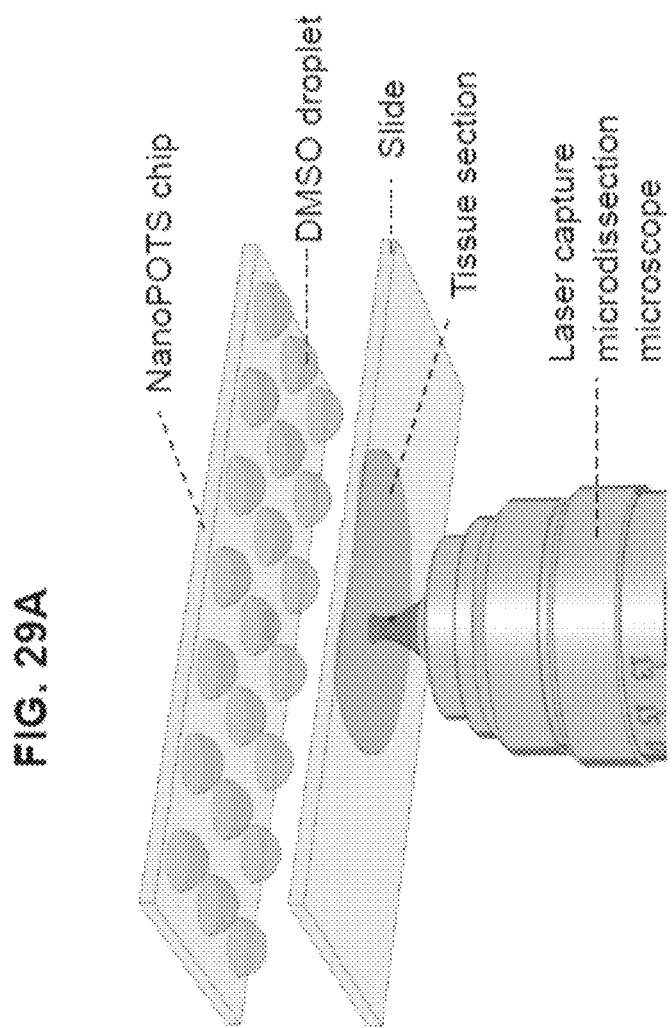
FIGS. 29A-29E (FIG. 29A) Schematic diagram showing the direct integration of laser capture microdissection (LCM) with a nanowell chip using dimethyl sulfoxide (DMSO) droplets for tissue capture.
Figure 29B:
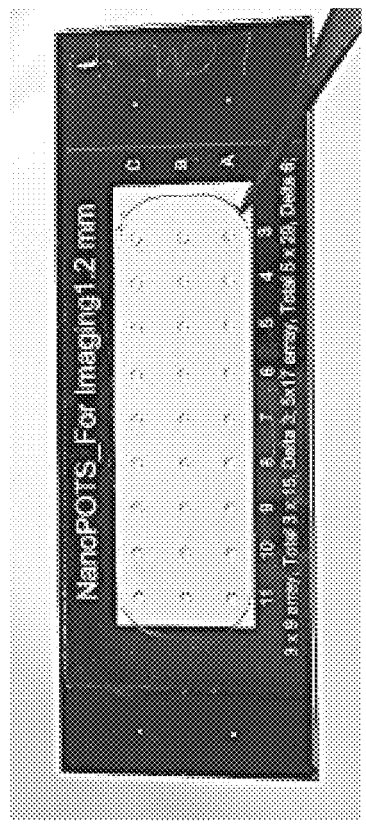
Figure 29C:
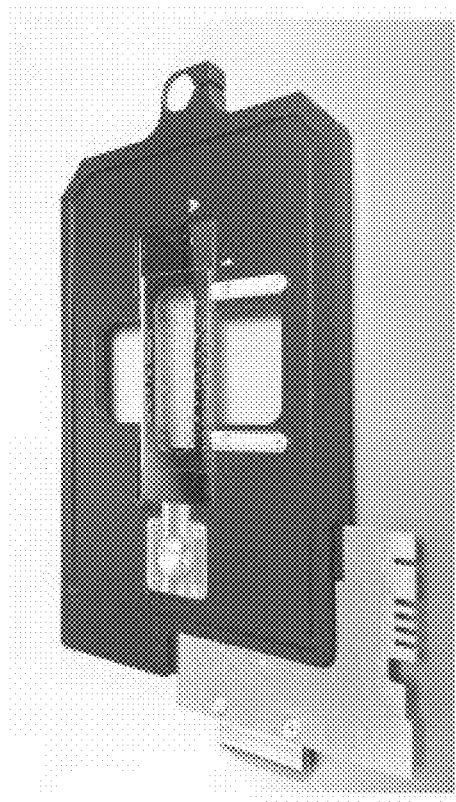
Figure 29D:
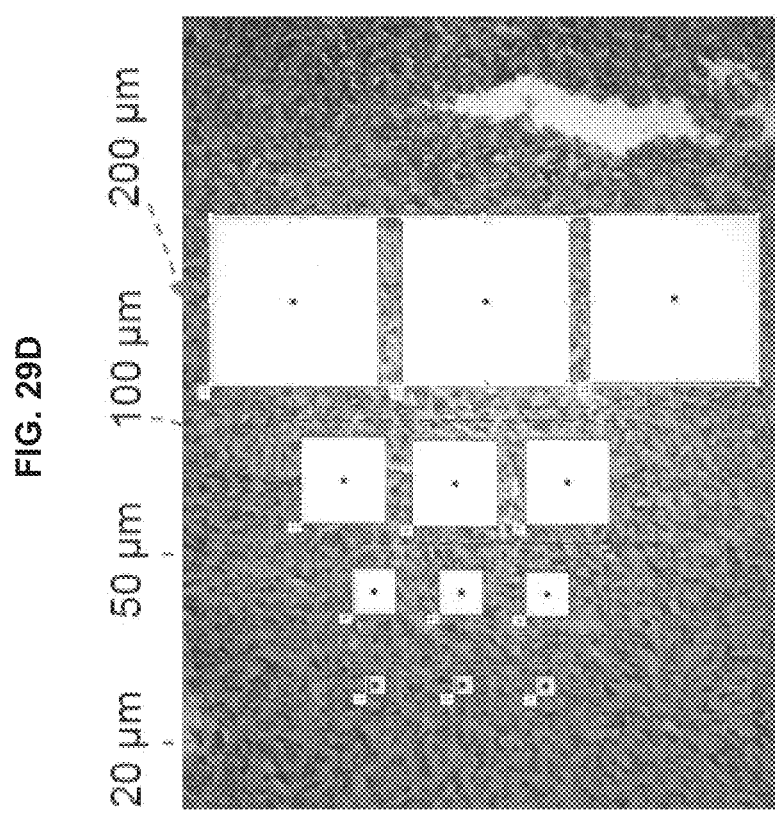

Laser capture microdissection. Unless mentioned otherwise, an array of DMSO droplets with a volume of 200 nL were deposited on nanowells using a nanoliter-dispensing robotic system (FIG. 29B). A PALM microbeam laser capture microdissection system (Carl Zeiss Microlmaging, Munich, Germany) was employed. The nanowell chip was fixed on a standard adapter for microscope slide (SlideCollector 48, Carl Zeiss Microlmaging) and then mounted on the robotic arm of the LCM system (FIG. 29C). The brain tissues were cut at an energy level of 42, and catapulted into DMSO droplet using the "CenterRoboLPC" function with an energy level of delta 15 and a focus level of delta 10. Tissue samples in the nanowell chip could be processed directly or stored at −20° C.

Figure 29E:
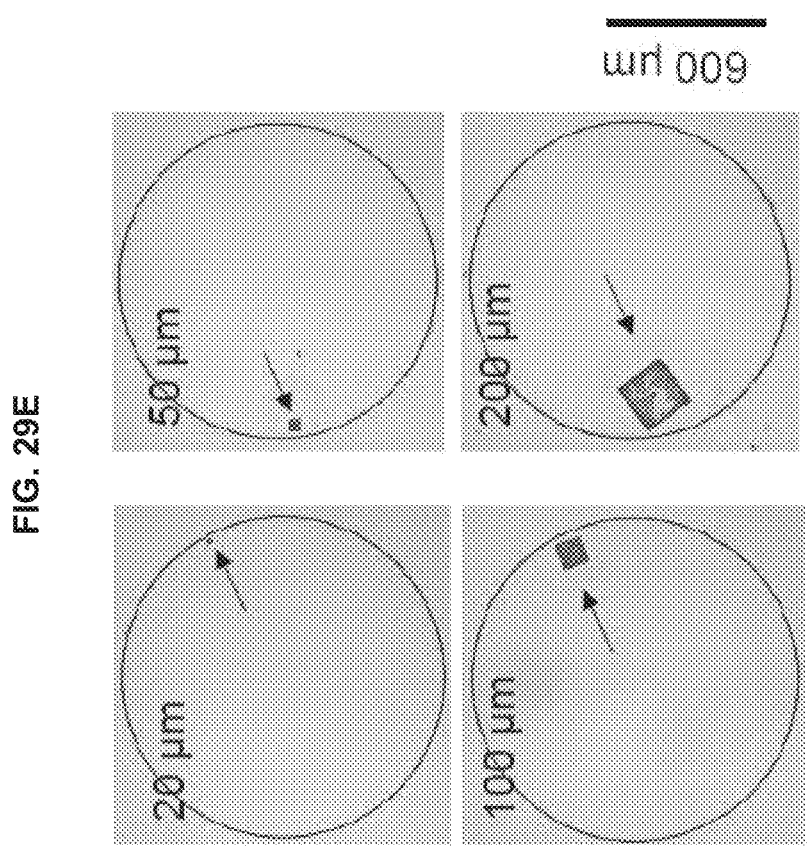

NanoPOTS proteomic sample processing. Before processing, DMSO droplets were evaporated to dryness by keeping the nanowell chip in a vacuum desiccator for 10 to 15 min (FIG. 29E). Reagent dispensing was performed using the robotic system as described previously. (Zhu, Anal. Chem. 2013, 85 (14), 6723-6731; Zhu, Sci. Rep. 2015, 5, 9551; Zhu, Sci. Rep. 2014, 4, 5046) Briefly, 100 nL 1×PBS buffer containing 0.2% DDM surfactant and 5 mM DTT was added into each nanowell. The chip was incubated at 70° C. for 1 h for protein extraction and denaturation. Proteins were then alkylated by adding 50 nL of 30 mM IAA in 50 mM ammonium bicarbonate (ABC) in each reaction and then incubating for 40 min in the dark. A two-step digestion was performed at 37° C. with Lys-C and trypsin for 4 h and 8 h, respectively. Finally, the digested peptide samples were collected and stored in a fused silica capillary (4 cm long, 200 μm i.d., 360 μm o.d.). Each nanowell was washed twice with 200 nL, 0.1% formic acid aqueous buffer and the wash solution was also collected into the same capillary to maximize sample recovery. To prevent residual PEN membrane pieces be drawn into the collection capillary, the distance between the capillary distal end and the nanowell surface was kept at 100 μm during the sample aspiration process. The capillary was sealed with Parafilm at both ends and stored at −70° C. until analyzed.

NanoLC-MS/MS for protein identification. Samples in the collection capillary were desalted and concentrated on a solid phase extraction (SPE) column (75-μm-i.d. fused silica capillary packed with 3 μm, 300 Å pore size C18 particles, Phenomenex, Terrence, Calif.). Peptides were separated using a 60-cm-long, 30-μm-i.d. nanoLC column (3 μm, 300 Å pore size C18 particles, Phenomenex) with an integrated electrospray emitter (Self-Pack PicoFrit column, New Objective, Woburn, Mass.). A nanoUPLC pump (Dionex UltiMate NCP-3200RS, Thermo Scientific, Waltham, Mich.) was used to deliver mobile phase to the LC column. To obtain reproducible and smooth gradient profiles, a tee interface was used to split the LC flow rate from 300 nL/min to 50 nl/min for the 30-μm-i.d. LC column. A linear 100-min gradient starting from 8% buffer B (0.1% formic acid in acetonitrile; buffer A: 0.1% formic acid in water) to 22%, followed by a 15-min linear increase to 35% buffer B. The column was washed with 90% buffer B for 5 min and re-equilibrated with 2% buffer B for 20 min prior to the subsequent analysis.

Peptides were ionized at the nanospray source using a potential of 2 kV. An Obitrap Fusion Lumos Tribrid MS (ThermoFisher) operated in data dependent mode to automatically switch between full scan MS and MS/MS acquisition with a cycle time of 2 s. The ion transfer capillary was heated to 250° C. to accelerate desolvation, and the S lens was set at 30. Full-scan MS spectra (m/z 375-1600) were acquired in the Orbitrap analyzer with 120,000 resolution (m/z 200), and AGC target of $3\times10^6$, and a maximum ion accumulation time of 246 ms. Precursor ions with charges from +2 to +7 were isolated with an m/z window of 2 and were sequentially fragmented by high energy dissociation (HCD) with a collision energy of 30%. The AGC target was set at $1\times10^5$. MS/MS scan spectra were acquired in the Orbitrap with an ion accumulation time of 502 ms and resolution of 240,000 for 50-μm-diameter tissue sample, an ion accumulation time of 246 ms and 120,000 resolution for 100-μm-diameter tissue sample, or an ion accumulation time of 118 ms and 60,000 resolution for 200-μm-diameter tissue samples, respectively.

Data Analysis. Raw data were analyzed by MaxQuant 1.5.3.30 as previously described. Briefly, Andromeda engine was used to search MS/MS spectra against a UniProtKB/Swiss-Prot mouse database containing 16,935 reviewed entries. Carbamidomethylation was set as a fixed modification, and n-terminal protein acetylation and methionine oxidation were set as variable modifications. Recalibrated MS/MS spectra were matched with a tolerance of 5 ppm on precursor mass and 20 ppm on fragment mass. The minimum peptide length was set at 6 amino acids, and maximum peptide mass was 4600 Da. Two missed cleavages were allowed for each peptide. A false discovery rate (FDR) of 1% was applied for both peptide and protein filtering. For the spatially resolved study of brain tissue samples, Match Between Runs (MBR) was activated to enhance identification sensitivity. The time widows for feature alignment and match were 20 min, and 0.7 min, respectively. Label-free relative protein quantification (LFQ) was performed in each parameter group containing tissue samples of similar size.

Contamination and reverse identification was filtered with Perseus (version 1.5.6.0). For relative quantification, the LFQ intensities were transformed with log 2 function, and then filtered to contain >70% valid values in at least one group. The missing values were imputed by normal distribution in each column with a width of 0.3 and a down shift of 1.8. To identify significant differences, ANOVA multiple sample test with permutation-based FDR control approach was used. P-value <0.01, q-value <0.05, and fold change >4 (S0=2) were required to obtain significant proteins. The results were exported to a table and visualized with OriginPro 2017 and an online tool powered by R language.

The capture efficiency with square tissues having side lengths of 20 µm, 50 µm, 100 µm, and 200 µm using a 12-µm-thick breast cancer tissue section from a previous study was evaluated. For smaller tissue samples with square side lengths from 20 µm to 100 µm, a total of 75 cuts were collected into three droplets for each size. For the largest tissue samples (200 µm), a total of 27 cuts were collected. The "CenterRoboLPC" function, in which the catapult laser pulse was applied at the centroid of pre-cut tissue piece, was used instead of commonly-used "RoboLPC". The "CenterRoboLPC" function provided better control on the catapult trajectory of tissue pieces from slide to DMSO droplets. Under the optimized condition, the capture efficiencies ranged from 92% to 97% for smaller tissue samples (20 µm to 100 µm), indicating the majority of LCM tissues can be collected (FIG. 30B). When tissue diameters were equal to or larger than 200 µm, all were successfully collected. With the increase of tissue sizes, the dissection time increased from 6 s to 15 s for each tissue sample. The high-speed dissection and high capture efficiencies, along with batch sample processing, should enable many applications requiring high-throughput proteomic studies such as large-scale mapping of heterogeneous tissues. It should also be noted that tissue pieces with a diameter of 20 µm correspond to single cells in most of mammalian tissues, demonstrating the potential of the present approach for single-cell isolation and analysis.

Figure 31B:
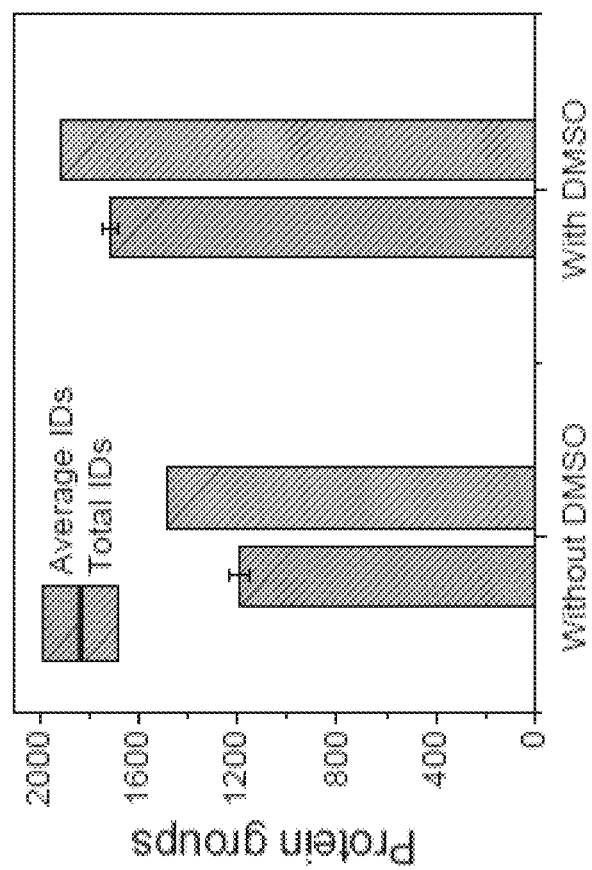
Figure 31C:
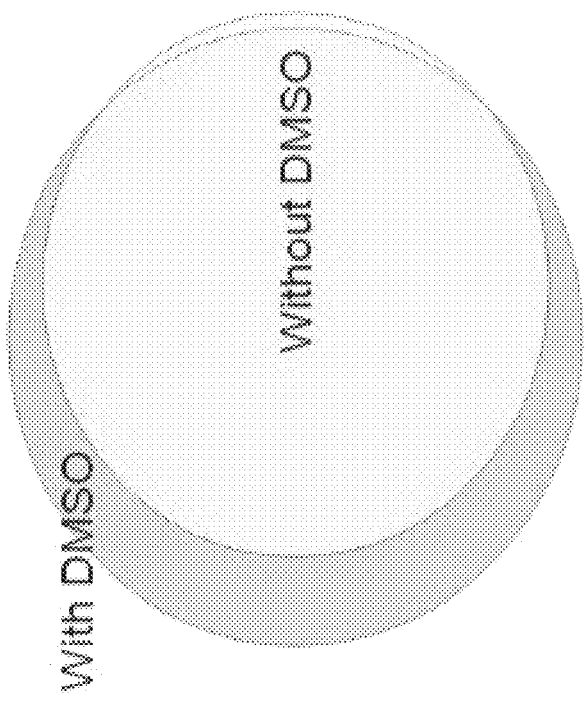

Proteomic analysis of LCM isolated rat brain tissues. To determine whether DMSO adversely affected tissue analysis, rat cortex tissue samples collected with DMSO droplets were analyzed, and compared with that obtained using manual transfer without DMSO. Surprisingly, a 71% and 69% increase in average and total unique peptide identifications was observed, respectively, resulting in the corresponding 44% and 29% increase in protein identifications, when DMSO was used for tissue collection (FIG. 31A). A Venn diagram of total protein identifications indicates that most of the proteins obtained from DMSO-free samples were included in that of DMSO-collected samples (FIG. 31B). This demonstrates that the use of DMSO droplets did not generate any negative effects on the proteomic analysis. On the contrary, proteome coverage significantly increased for small tissue samples. A possible explanation for this result is that protein extraction efficiency was improved after hydrophobic lipids were removed by DMSO in the brain tissue. Protein extraction from tissue samples was found to be more challenging than for cultured cells, especially for tissue containing high lipid content such as brain. Various approaches have been developed to address this challenge by employing strong detergents or organic solvent in the extraction buffer. As a type of organic solvent, DMSO is expected to have high solubility for most lipids, and thus could dissolve them prior to protein extraction. Compared with commonly used detergent approaches, sample losses in detergent removing steps including buffer exchange and spin columns was avoided using the inventive approach described herein. These merits of DMSO have thus provided an added benefit in the workflow of spatially-resolved proteomic analysis.

Figure 31E:
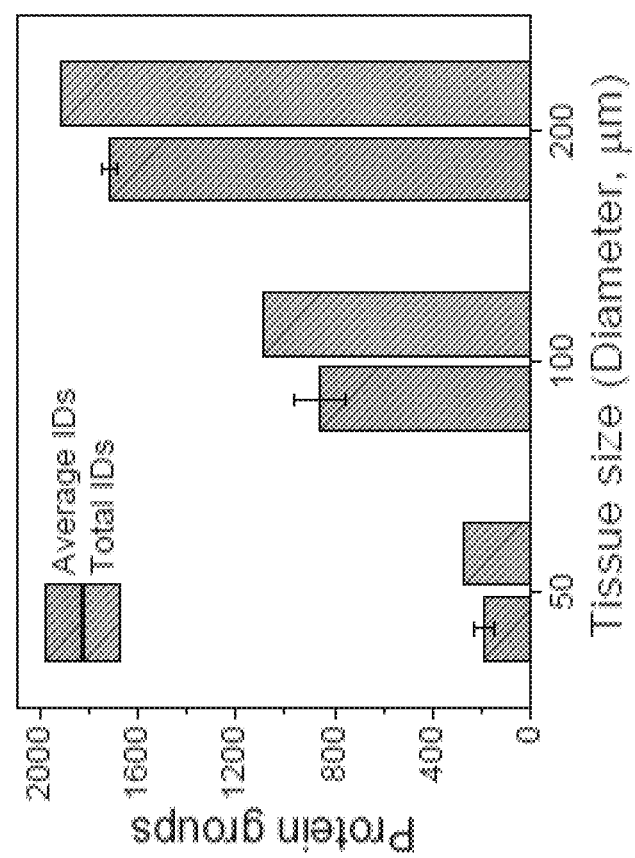
Figure 31F:
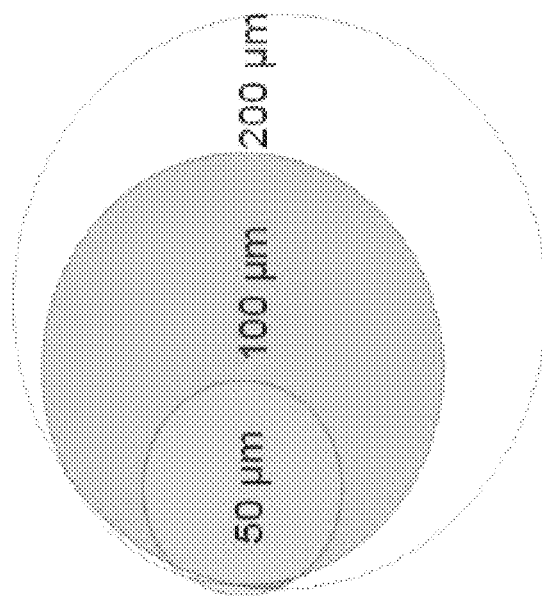

The sensitivity of the LCM-DMSO-nanoPOTS system on proteomic analysis of small tissue samples was tested. Rat cortex tissue with diameters of 50 µm, 100 µm, and 200 µm were used as model samples. Based on hematoxylin staining of cell nuclei provided by Allen brain atlas project, the corresponding cell numbers were ~3-10, 20-40, and 40-100, for the different tissue diameters, respectively. FIGS. 31D and 31E show the linear increase of unique peptide and protein identifications with tissue size. As expected, nearly all peptides and proteins identified in the smaller tissues were also identified in larger tissues (FIG. 31D), demonstrating analytical sensitivity dominated the proteome coverage. The present system is capable of identifying an average of 159±40, 857±104, and 1717±33 protein groups (n=3) from cortex tissues with diameters of 50 µm, 100 µm, and 200 µm, respectively. Compared with previous spatially-resolved proteomic studies, in which at least millimeter-sized tissues were required to obtain a depth >1000 proteins, the LCM-DMSO-nanoPOTS system provided >25 times better spatial resolution with higher proteome coverage.

Figure 31G:
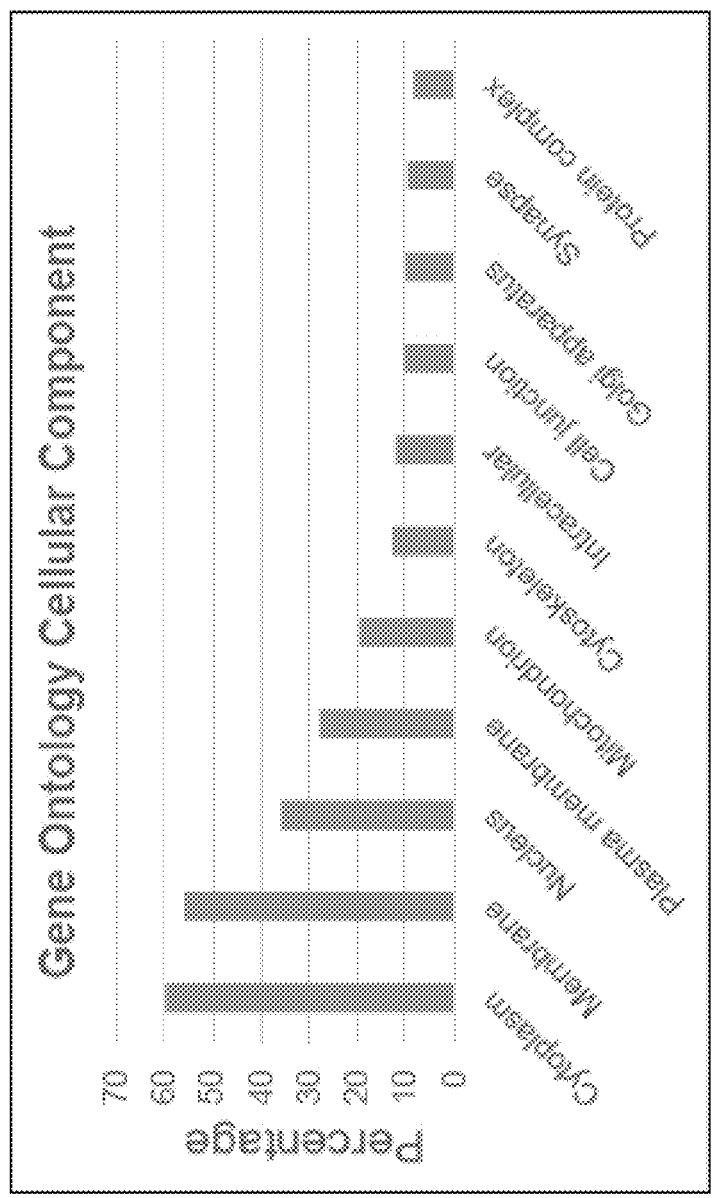

The 1918 total proteins identified from 200-µm-diameter cortex tissues were submitted for Gene Ontology Cellular Component (GOCC) analysis. As shown in FIG. 31G, we observed a high percentage (56%) of membrane proteins and half of them (28%) were localized in plasma membrane, although no specific sample preparation procedures were used for membrane proteins. 10% synapse proteins and 7% axon proteins (not shown in FIG. 31G), which are vital for brain function, were also observed. In brain, the major neurotransmitters are glutamate and GABA, which play excitatory and inhibitory functions, respectively. In the plasma protein category, we identified three types of GABA receptors (GABRA1, GABRA2, GABRB1, GABRB2, GABRB2, and GABRG2), and a large family of glutamate receptors including DRIA1, DRIA2, DRIA3, DRIA4, GRM2, GRM3, GRM5, GPR158, GRIK3, GRIN1, GRIN2a, and GRIN2b.

Quantitative, spatially-resolved proteomic study of rat brain tissues. The performance of the LCM-DMSO-nanoPOTS system was evaluated for quantitative and spatially-resolved proteomic studies, we dissected and analyzed three different rat brain regions (cerebral cortex (CTX), corpus callosum (CC), and caudoputamen (CP)) from a 12-µm-thick coronal section (FIGS. 32A-32C). Tissue samples were dissected with a diameter of 100 µm, corresponding to an area of ~0.008 mm². The spatial distances (center to center) were from 116 µm to 716 µm between the same regions, and from 424 µm to 1,727 µm between different regions (FIG. 32A), showing the high spatial resolution of the present measurement. For each region, six samples were processed and four of them were submitted for LC-MS analysis (FIG. 32B).

To increase the quantifiable proteins, the Match Between Runs (MBR) algorithm of Maxquant was used, wherein the peptides were identified based on accurate intact masses and LC retention times (AMTs). A total 1896 protein groups were identified and 1393 (73.5%) were common across all the three brain regions. After stringent filtering for valid log 2-transformed LFQ values, 1,003 protein groups were quantifiable. A high correlation with Pearson's correlation coefficients from 0.97 to 0.99 was observed between biological replicates of the same tissue regions, demonstrating excellent technical and biological reproducibility of the present system for quantification (FIG. 32C). Between different tissue regions, CTX and CP shows lower in correlation coefficients from 0.94 to 0.97, while CC has lowest correlations (from 0.83 to 0.91) with the other two regions. Such differences are also indicated in the morphology of the brain tissue (FIG. 32A).

The LCM-DMSO-nanoPOTS system was tested to see if it could be applied to distinguish different tissue types. Unsupervised principal component analysis (PCA) was used to process the LFQ intensity data from the 12 tissue samples. As shown in FIG. 33A, the three tissue regions were segregated based on component 1 and component 2, which accounted for 65.5% and 15.6%, respectively. All four biological replicates were well clustered within the corresponding tissue region without overlap with other regions, suggesting the present system can efficiently distinguish tissue types based on their protein expressions.

To identify significant differences in protein expression among the three tissue regions, a multiple sample ANOVA test was employed with a permutation-based FDR algorithm, which is embedded in Perseus data analysis platform. Using a difference (S0) of 2, p-value of 0.01, and a FDR level of 0.05, 233 out of total 1003 quantifiable protein groups were identified to have significant differences. The most abundant proteins, such as Tuba1b, Tubb2a, Actb, Sptan1, Cltc, and Atp5b, were found to have no difference in LFQ intensity, which agrees well with previous report. For the 233 significant proteins, 32, 27, 43 proteins groups enriched in CTX, CC, and CP regions with fold change >2 over their mean values were observed, respectively. To visualize the difference, we used unsupervised hierarchical clustering analysis (HCA) of the significant proteins (FIG. 33B). Similar to PCA plot, each four replicates from the same regions were clustered together. In addition, each region has distinct hot spots in protein abundance relative to other regions, indicating different biological functions existed in these regions.

The results described herein demonstrate that the LCM-capture liquid-nanoPOTS platform significantly advances spatially-resolved proteomics by improving the resolution and increasing the sensitivity. The use of DMSO droplets not only served to efficiently capture dissected tissue pieces as small as 20-µm diameter (single-cell scale) into nanowells, but also significantly improved the proteome coverage. The whole workflow can be fully automated without manual transfer, and thus sample loss and protein contamination is minimized. This platform may play an important role in proteomic analyses and may be applied to various fields including biomedical research, clinical diagnosis, microbial community, and plant science. Finally, the LCM-capture liquid-nanoPOTS platform should be readily extended to other omics studies requiring tissue isolation and nanoscale processing, such as transcriptomics, lipidomics, and metabolomics.

nanoPOTS with Automated Proteome Analysis and Imaging

In embodiments, aspects of the sample preparation, processing, and/or transfer are configured to facilitate automation and/or performance by robotic sub-systems. For example, systems and methods for proteome analysis enable high-throughput processing and/or protein imaging that utilizes label-free nanoproteomics to analyze tissue voxels. Quantitative images for thousands of proteins with very fine spatial resolution can be generated. At least twenty-five-fold increases can be obtained in protein coverage compared to other technologies.

While high-throughput analysis and imaging without labels exists for some biological molecules, there are significant limitations in their application to protein molecules. For example, mass spectrometry imaging (MSI) is a powerful tool for mapping the spatial distribution of biological molecules across an area of interest. In an MSI experiment, a probe (e.g., laser, ion beam, liquid junction) serially moves across a surface to desorb or extract biomolecules that are then directly analyzed by mass spectrometry. This allows for the creation of detailed spatial maps that reveal the native distribution of biomolecules at the surface without labels or pre-treatments. However, molecules are transmitted directly from the tissue to the mass spectrometer without separation, limiting the dynamic range of observed analyte concentrations and restricting detection to the most abundant species. Furthermore, the ionization process for a given analyte is impacted by other constituents in the mixture (so-called "matrix"), and since ionization efficiency is strongly influenced by the sample matrix, quantitative comparisons are often challenging. These factors are compounded when imaging proteins, many of which are present in significantly lower abundances than many metabolites and lipids. Additionally, MS detection of intact protein species is challenging due to poor ionization efficiency, and larger isotopomer envelopes, further reducing the achievable signal-to-noise ratio. As a result, MSI techniques are not sufficiently capable of imaging at the proteome level.

Proteomics methods based on LC-MS/MS have become an indispensable tool in biological research. Significant investment has been made in developing robust methodologies for quantitative proteomics to monitor changes in the proteome between different patients and treatment conditions. This powerful approach offers a highly comprehensive molecular profile of the specimen of interest. To achieve this level of coverage and measurement accuracy, proteins need to be extracted, digested into peptides, and separated by LC-MS for effective MS analysis. This processing creates a significant challenge however, as it requires a relatively large amount of starting material for analysis. Consequently, the requisite bulk extraction process blurs spatial information about differing cell types and tissue context, critical to obtaining a systems-level understanding of the specimen. Proteomic approaches have been combined with isolation techniques such as laser capture microdissection (LCM) and fluorescence assisted cell sorting; however, applications have been limited to date due to technical challenges. Furthermore, deep protein coverage requires the use of time consuming liquid chromatography separations which challenges the achievable sample throughput.

Described herein are methods and systems that can address the limitations associated with proteome-level analysis and imaging. A schematic of one embodiment is shown in FIG. 35. A biological sample 3503 is placed in one of a plurality of nanoPOTS reactor vessels 3502 on a nanoPOTS plate. The biological sample can be a tissue sample 3505 obtained by an LCM laser 3504, as illustrated. In a bottom-up proteomics approach, a complement of proteins in the biological sample can be digested 3506 to yield a processed sample comprising peptides 3507 related to the complement of proteins. In a top-down proteomics approach (not illustrated), a complement of proteins in the biological sample can be extracted and/or purified to yield a processed sample. The processed sample 3507 is extracted from the nanoPOTS reactor vessel with a syringe 3510, leaving minimal amounts of the processed sample 3509 in the substantially empty NanoPOTS reactor vessel 3508. The extracted processed sample is dispensed into a well 3511 on a well plate 3512 having a plurality of wells. The well can be pre-loaded with a volume of liquid carrier buffer to receive the extracted processed sample. In the illustrated embodiment, a syringe 3513 dispenses a volume of a wash solution into the NanoPOTS reactor vessel 3508. Residual amounts of the processed sample are incorporated into the wash solution. The contents of the NanoPOTS reactor vessel 3514 are transferred in a syringe 3515 to the well 3511, thereby diluting the contents of the well and yielding a diluted sample. The washing of the nanoPOTS reactor vessel and transferal of the vessel contents can be repeated to ensure that the maximum amount of processed sample is transferred into the well. The diluted sample is then transferred 3516 from the well to a MS-based analytical instrument 3517. As illustrated, the transfer may be accomplished using a syringe tip 3519 having a notch 3518 in the proximal end at the face surface. The syringe is inserted into the well such that the tip contacts, or nearly contacts, the well plate. The notch enables maximum extraction from the well by preventing a seal between the syringe tip and the well surface.

Referring to FIGS. 36A and 36B, an embodiment of the notched syringe tip is illustrated. The notch 3518 is located at the end 3606 of a syringe tip 3519 and is not located on the side 3605 of the syringe tip. The notch is aligned with at least a portion of the aperture 3604 at the end to allow fluid flow via the notch into the channel 3603 in the syringe. During extraction, the syringe tip is inserted in a well and the tip contacts the well surface 3601. In certain embodiments, the tip can nearly contact the well surface without actual contact. The notch 3518 prevents a seal from preventing extraction of the liquid contents 3602 of the well. In one embodiment, the notch is created by using a copper electrode from an electrical discharge machining tool (EDM) to remove a portion of the syringe tip from the end of the tip. In certain embodiments, the syringe can have a plurality of notches in the end of the syringe tip.

Referring to FIG. 37, spatial regions of a biological sample can be co-registered with NanoPOTS reactor vessels and/or well plate wells in order to facilitate proteome mapping and imaging. In the illustrated embodiment, a tissue sample 3708 can be taken from a section of tissue 3701. The tissue sample can be voxelated and each voxel 3702 can be co-registered with a NanoPOTS reactor vessel 3704 and a well plate well 3705. In one example, voxelation can be achieved by overlaying a grid on the tissue sample and using a LCM laser to dissect voxels according to the grid. After protein identification using the MS-based analytical instrument, a protein image map can be generated correlating the presence, and in some embodiments the quantity, of each of a plurality of proteins with the voxel (i.e., spatial region of the tissue sample) from which the protein originated (see image maps in element 3709). In certain embodiments, the tissue sample voxel has dimensions less than or equal to 500 µm. In other embodiments, the tissue sample voxel has dimensions less than or equal to 100 µm.

In some embodiments, the generation of a visual representation of the protein identifications mapped to a spatial region of a tissue sample utilizes software executed by processing circuitry to search, process and visualize the data. For example, each peptide can be identified by comparing the experimental tandem mass spectra to theoretical tandem mass spectra of a collection of peptides in a protein. Relative protein quantifications can be calculated based on the MS peak intensities for the collection of peptides associated with the identified protein. The identified and quantified proteins can then be assigned to the spatial region with which the originating well and nanoPOTS reactor vessel was co-registered.

Example: Mouse Uterine Tissue Proteome Analysis and Imaging

Utilizing the LoxP-Cre system, transgenic mice with uterine specific inactivation of $Wnt5a^{d/d}$($Wnt5a^{loxP/loxP}$) were generated. This transgenic mouse model of impaired embryo implantation contains morphological, cellular, and molecular changes in the uterus including disrupted luminal epithelial evaginations (crypts) at the antimesometrial domain. These crypts are an essential step in the receptive uterus prior to embryo attachment. Uterine tissue from one $Wnt5a^{d/d}$ mouse was sectioned with a thickness of 12 µm using a cryostat. The temperatures of chuck and blade were set at −16° C. and −20° C. for liver tissues and −16° C. and −20° C. for uterus tissues. The tissue sections were deposited on PEN membrane slides and stored in a freezer at −80° C.

Tissue fixative solution (70% ethanol) were pre-cooled in 4° C. before use. Tissue sections were immediately immersed into 70% ethanol for 15 s after removal from the −80° C. freezer or dry-ice box. Rehydration was performed for 30 s in deionized water. Next, the tissue sections were immersed in Mayer's hematoxylin solution (Sigma-Aldrich, St. Louis, USA) for 1 min, dipped twice in deionized water to remove excess dye solution, and immersed in Scott's Tap Water Substitute (Sigma-Aldrich) for 15 s to dye the tissues. Finally, tissue dehydration was performed by sequentially immersing the tissue sections in 70% ethanol for 1 min, 95% ethanol for 1 min, 100% ethanol for 1 min, and xylene for 2 min. The sections were dried in a fume hood for 10 min, which can be directly used or stored in −80° C. until use.

Fabrication of Nanowell Chip

NanoPOTS plates comprising nanowell chips were fabricated from glass slides with precoated chromium and photoresist layers (Telic company, Valencia, USA) using standard photolithography and wet chemical etching procedures. An array of 3×9 nanowells (i.e., NanoPOTS reactor vessels) with a diameter of 1.2 mm and a center-to-center spacing of 4.5 mm was designed in AutoCAD and printed with a Direct-Write Lithography (DWL) System (SF-100, Intelligent Micro Patterning LLC, St. Petersburg, USA). After exposure, development, and chromium etching, the slides were etched in a solution of 2:4:4 (v:v:v) buffered hydrofluoric acid, hydrochloric acid, and water at an etch rate of 1 µm/min for 10 min. After drying in 120° C. for 2 h, the slides were treated with 2% (v/v) heptadecafluoro-1, 1,2,2-tetrahydrodecyldimethylchlorosilane in 2,4-trimethylpentane. After removing the remaining chromium layer, an array of hydrophilic spots was formed on a hydrophobic background. A glass frame (machined by Coherent Inc., Santa Clara, Calif.) with a thickness of 1 mm and a width of 5 mm was affixed to the nanowell slide using silicone adhesive. Finally, a sealing cover plate was fabricated by spin-coating a layer of polydimethylsiloxane (PDMS, 30-μm in thickness). The sealing cover slide was used to reversibly seal the nanowell chip during reaction incubation.

Laser Capture Microdissection of Tissue Sections

Before experiments, nanowells were prepopulated with 200 nL DMSO droplets serving as capture media. Laser capture microdissection (LCM) was performed on a PALM MicroBeam system (Carl Zeiss MicroImaging, Munich, Germany). A slide adapter (SlideCollector 48, Carl Zeiss MicroImaging) was used to mount a nanowell chip on the LCM microscope. Voxelation of the tissue section was achieved by first drawing a grid on the tissue using Palm-Robo software, followed by tissue cutting and catapulting. Both liver and uterine tissues were cut at an energy level of 42, and an iteration cycle of 2 to completely separate 100 μm×100 μm tissue voxels. The "CenterRoboLPC" function with an energy level of delta 10 and a focus level of delta 5 was used to catapult tissue voxels into DMSO droplets. The "CapCheck" function was activated to confirm successful sample collection from tissue sections to DMSO droplets.

Proteomic Sample Processing

The nanowell chip was heated to 70° C. for 10 min to evaporate the DMSO droplet. A nanoliter-resolution robotic liquid handling platform was employed to dispense reagents into nanowells. First, a cell lysis buffer containing 0.2% (w/v) n-dodecyl-β-D-maltoside (DDM, Sigma-Aldrich), 5 mM Dithiothreitol (DTT) and 1×PBS was applied into each nanowell with a volume of 100 nL. The chip was incubated at 70° C. for 1 h for cell lysis, protein extraction and denaturation. Next, 50 nL of 30 mM iodoacetamide (IAA) in 50 mM ammonium bicarbonate (ABC) buffer (pH 8.0) were added to each well and incubated in the dark for 30 min. Protein digestion was performed by dispensing 50 nL of 0.01 ng/nL Lys-C (MS grade, Promega, Madison, USA) and trypsin (Promega) in ABC buffer, and incubated for 4 h and 8 h, respectively. Finally, the enzymatic reaction was terminated by adding 50 nL of 0.5% trifluoroacetic acid (TFA) in aqueous buffer and incubated for 30 min.

The processed samples were transferred into 96-well PCR well plates for LC-MS analysis. The 96-well plate was prefilled with 25 μL of 0.1% TFA and 0.02% DDM aqueous buffer. The robotic platform was used to aspirate nanoliter samples from the nanowells and dispense the samples into the 25-4, buffer. Each nanowell was washed twice with 200 nL of a wash solution that comprised the same buffer to maximize sample recovery. Finally, the 96-well plates were sealed with sealing tape (Nunc, Thermo Scientific) and stored at −20° C.

Sample Analysis with SPE-LC-MS/MS

A LC cart was employed to automatically perform sample injection, sample cleanup, and LC separation. The cart consisted of a PAL autosampler (CTC ANALYTICS AG, Zwingen, Switzerland), two Cheminert six-port injection valves (Valco Instruments, Houston, USA), a binary nanoUPLC pump (Dionex UltiMate NCP-3200RS, Thermo Scientific), and a HPLC sample loading pump (1200 Series, Agilent, Santa Clara, USA). Both SPE precolumn (150 μm i.d., 4 cm length) and LC column (50 μm i.d., 70-cm Self-Pack PicoFrit column, New Objective, Woburn, USA) were slurry-packed with 3-μm C18 packing material (300-Å pore size, Phenomenex, Terrence, USA). Sample was injected in a 20-4, loop and loaded on SPE column using Buffer A (0.1% formic acid in water) at a flow rate of 5 μL/min for 20 min. The purified sample was separated at a flow rate of 150 nL/min and a 75 min gradient of 8-35% Buffer B (0.1% formic acid in acetonitrile). LC column was washed using 80% Buffer B for 10 min and equilibrated using 2% Buffer B for 20 min.

A QExactive Plus Orbitrap MS (Thermo Scientific) was used to analyze the separated peptides. A 2.2 kV high voltage was applied at the ionization source to generate electrospray and ionize peptides. The ion transfer capillary was heated to 250° C. to desolvate droplets. The S-lens RF level was set at 70. Data dependent mode was employed to automatically trigger precursor scan and MS/MS scans. Precursors were scanned at a resolution of 35,000, an AGC target of 3E6, a maximum ion trap time of 50 ms, and mass range of 375-1800. Top-12 precursors were isolated with an isolation window of 2, an AGC target of 1E5, a maximum ion trap time of 150 ms, and then fragmented by high energy collision (HCD) with an energy level of 32%. A dynamic exclusion of 30 s was used to minimize repeated sequencing. MS/MS spectra were scanned at a resolution of 17,500.

Data Analysis.

All data files were processed using MaxQuant (version 1.5.3.30) for feature detection, database searching and protein/peptide quantification. Mass spectra were searched against the Uniprot Mus Musculus database downloaded in October 2016, containing 16,825 sequence entries. Carbamidomethylation of cysteine was set as a fixed modification and N-terminal acetylation and oxidation of methionine were allowed as variable modifications. A peptide length >6 was required with a maximum of two missed cleavages allowed, and a false discovery rate of 0.01. The searches were completed twice with these settings, first with the match-between-runs feature enabled and then without, for comparison. Contaminants and reverse sequences were removed from the peptides.txt file prior to use for downstream statistical analysis and image display.

Data Pre-Processing and Statistical Analysis.

The dominant cell population study contained 15 LC-MS/MS instrument runs associated with 15 unique biological samples, 5 stromal (S) samples, 5 luminal epithelium (LE) samples, 5 glandular epithelium (GE) samples, where 100-200 ng of these unique cell populations were captured from 3-5 sections for each of the 15 unique biological samples. From the Maxquant match-between-run search 19,952 peptides had at least 2 observations across the 15 analyses. The algorithm RMD-PAV was used to identify any outlier biological samples. Samples were also examined via Pearson correlation. No samples were identified as outliers.

Peptides with inadequate data for either qualitative or quantitative statistical tests were also removed from the dataset, resulting in a final dataset ready for normalization that included 15 unique biological samples and 17,387 measured unique peptides corresponding to 2,940 unique proteins. Median centering based on rank invariant peptides (0.2) was used for normalization Protein quantification was performed using r-rollup, which scales the peptides associated with each protein by a reference peptide and then sets their median as the protein abundance. The reference peptide is the peptide with the least missing data.

Pairwise univariate statistical comparisons were carried out between each of the three cell types using a Tukey-adjusted ANOVA or a Holm-corrected g-test to compare each pair of dominant cell types for each of the 2,940 proteins. The three statistical comparisons of interest were (1) LE vs GE, (2) S vs GE, and (3) S vs LE. The number of significant proteins for each of the three comparison based on the ANOVA adjusted p-values, were (1) 1,220 proteins increasing in the LE and 46 proteins increasing in the GE, (2) 1,673 proteins increasing in the S and 42 proteins increasing in the GE, and (3) 777 proteins increasing in the S and 196 proteins increasing in the LE.

The nanoPOTS imaging MS study was used to create 2D protein images of tissue sections comprised of our three cell types of interest. Imaged areas were taken from the center of uterine sections, enabling visualization of the uterine proteomic landscape orchestrating embryo implantation. The S dominant section, Image 1, contained 24 LC-MS/MS instrument runs associated with 24 unique biological samples, 4 containing GE & S, 8 containing LE, and 12 containing S. The LE dominant section, Image 2, contained 24 LC-MS/MS instrument runs associated with 24 unique biological samples, 2 containing GE & S, 14 containing LE, and 8 containing S. MaxQuant analysis of Image 1 characterized 8,065 measured unique peptides corresponding to 1,658 unique proteins that had at least 2 observations across the 24 runs. Employing match-between-runs characterized 9,411 measured unique peptides corresponding to 1,764 unique proteins that had at least 2 observations across the 24 runs. MaxQuant analysis of Image 2 characterized 11,803 measured unique peptides corresponding to 2,212 unique proteins that had at least 2 observations across the 24 runs. Employing match-between-runs characterized 13,797 measured unique peptides corresponding to 2,357 unique proteins that had at least 2 observations across the 24 runs. Median centering based on rank invariant peptides (0.2) was used for normalization. Trelliscope enable data visualization as bar graphs for our dominate cell-type data and virtual color-scaled protein images for our Image 1 and Image 2 experiments.

Proteins discussed in the manuscript were statistically significant (<0.05 adjusted p-value) in our dominate cell-type analysis and had complimentary spatial distributions in both Image 1 and Image 2.

All references throughout this application, for example patent documents including issued or granted patents or equivalents; patent application publications; and non-patent literature documents or other source material; are hereby incorporated by reference herein in their entireties, as though individually incorporated by reference.

The specific embodiments provided herein are examples of useful embodiments of the disclosure and it will be apparent to one skilled in the art that the disclosed embodiments can be carried out using a large number of variations of the devices, device components, methods steps set forth in the present description. As will be obvious to one of skill in the art, methods and devices useful for the present methods can include a large number of optional composition and processing elements and steps.

Every formulation or combination of components described or exemplified herein can be used to practice the disclosed embodiments, unless otherwise stated.

Whenever a range is given in the specification, for example, a temperature range, a time range, or a composition or concentration range, all intermediate ranges and sub-ranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any sub-ranges or individual values in a range or sub-range that are included in the description herein can be excluded from the claims herein.

One of ordinary skill in the art will appreciate that starting materials, biological materials, reagents, synthetic methods, purification methods, analytical methods, assay methods, and biological methods other than those specifically exemplified can be employed in the practice of the disclosed embodiments without resort to undue experimentation. All art-known functional equivalents, of any such materials and methods are intended to be included in the disclosed embodiments.

The terms and expressions which have been employed are used as terms of description and not of limitation, and there is no intention that in the use of such terms and expressions of excluding any equivalents of the features shown and described or portions thereof, but it is recognized that various modifications are possible within the scope of the claimed embodiments. Thus, it should be understood that although the disclosure can include discussion of preferred embodiments and optional features, modification and variation of the concepts herein disclosed may be resorted to by those skilled in the art, and that such modifications and variations are considered to be within the scope of the disclosure as defined by the appended claims.

The following non-patent literature documents are incorporated by reference in their entirety.

1. Achim, K. et al. High-throughput spatial mapping of single-cell RNA-seq data to tissue of origin. *Nat. Biotechnol.* 33, 503-509 (2015).
2. Jaitin, D. A. et al. Massively parallel single-cell RNA-seq for marker-free decomposition of tissues into cell types. *Science* 343, 776-779 (2014).
3. Shapiro, E., Biezuner, T. & Linnarsson, S. Single-cell sequencing-based technologies will revolutionize whole-organism science. *Nat. Rev. Genet.* 14, 618-630 (2013).
4. Bendall, S. C. et al. Single-cell mass cytometry of differential immune and drug responses across a human hematopoietic continuum. *Science* 332, 687-696 (2011).
5. Smith, R. D., Shen, Y. & Tang, K. Ultrasensitive and quantitative analyses from combined separations-mass spectrometry for the characterization of proteomes. *Acc. Chem. Res.* 37, 269-278 (2004).
6. Shen, Y. et al. Ultrasensitive proteomics using high-efficiency on-line micro-spe-nanolc-nanoesi ms and ms/ms. *Anal. Chem.* 76, 144-154 (2004).
7. Sun, L. et al. Ultrasensitive and fast bottom-up analysis of femtogram amounts of complex proteome digests. *Angew. Chemie-Int. Ed.* 52, 13661-13664 (2013).
8. Kelly, R. T., Tolmachev, A. V, Page, J. S., Tang, K. & Smith, R. D. The ion funnel: Theory, implementations, and applications. *Mass Spectrom. Rev.* 29, 294-312 (2010).
9. Li, S. et al. An integrated platform for isolation, processing, and mass spectrometry-based proteomic profiling of rare cells in whole blood. *Mol. Cell. Proteomics* 14, 1672-1683 (2015).
10. Sun, X., Kelly, R. T., Tang, K. & Smith, R. D. Ultrasensitive nanoelectrospray ionization-mass spectrometry using poly(dimethylsiloxane) microchips with monolithically integrated emitters. *Analyst* 135, 2296-2302 (2010).
11. Wang, H. et al. Development and evaluation of a micro- and nanoscale proteomic sample preparation method. *J. Proteome Res.* 4, 2397-403 (2005).
12. Wiśniewski, J. R., Ostasiewicz, P. & Mann, M. High recovery FASP applied to the proteomic analysis of microdissected formalin fixed paraffin embedded cancer tissues retrieves known colon cancer markers. *J. Proteome Res.* 10, 3040-3049 (2011).

13. Chen, Q., Yan, G., Gao, M. & Zhang, X. Ultrasensitive proteome profiling for 100 living cells by direct cell injection, online digestion and nano-lc-ms/ms analysis. *Anal. Chem.* 87, 6674-6680 (2015).
14. Chen, W. et al. Simple and integrated spintip-based technology applied for deep proteome profiling. *Anal. Chem.* 88, 4864-4871 (2016).
15. Waanders, L. F. et al. Quantitative proteomic analysis of single pancreatic islets. *Proc. Natl. Acad. Sci U.S.A* 106, 18902-18907 (2009).
16. Huang, E. L. et al. Snapp: Simplified nanoproteomics platform for reproducible global proteomic analysis of nanogram protein quantities. *Endocrinology* 157, 1307-1314 (2016).
17. Wang, N., Xu, M., Wang, P. & Li, L. Development of mass spectrometry-based shotgun method for proteome analysis of 500 to 5000 cancer cells. *Anal. Chem.* 82, 2262-2271 (2010).
18. Lombard-Banek, C., Moody, S. A. & Nemes, P. Single-cell mass spectrometry for discovery proteomics: quantifying translational cell heterogeneity in the 16-cell frog (*xenopus*) embryo. *Angew. Chemie-Int. Ed.* 55, 2454-2458 (2016).
19. Sun, L. et al. Single cell proteomics using frog (*Xenopus laevis*) blastomeres isolated from early stage embryos, which form a geometric progression in protein content. *Anal. Chem.* 88, 6653-6657 (2016).
20. Wiśniewski, J. R., Hein, M. Y., Cox, J. & Mann, M. A 'proteomic ruler' for protein copy number and concentration estimation without spike-in standards. *Mol. Cell. Proteomics* 13, 3497-506 (2014).
21. Goebel-Stengel, M., Stengel, A., Taché, Y. & Reeve, J. R. The importance of using the optimal plasticware and glassware in studies involving peptides. *Anal. Biochem.* 414, 38-46 (2011).
22. Zhu, Y., Zhang, Y.-X., Cai, L.-F. & Fang, Q. Sequential operation droplet array: an automated microfluidic platform for picoliter-scale liquid handling, analysis, and screening. *Anal. Chem.* 85, 6723-6731 (2013).
23. Vandermarliere, E., Mueller, M. & Martens, L. Getting intimate with trypsin, the leading protease in proteomics. *Mass Spectrom. Rev.* 32, 453-465 (2013).
24. Shen, Y. et al. Coupling to 15-150-µ m-i. d. column liquid chromatography for proteomic analysis. *Anal. Chem.* 75, 3596-3605 (2003).
25. Tyanova, S., Temu, T. & Cox, J. The MaxQuant computational platform for mass spectrometry-based shotgun proteomics. *Nat. Protoc.* 11, 2301-2319 (2016).
26. Volpe, P. & Ereememko-Volpe, T. Quantitative studies on cell proteins in suspension cultures. *Eur. J. Biochem.* 12, 195-200 (1970).
27. Zeiler, M., Straube, W. L., Lundberg, E., Uhlen, M. & Mann, M. A Protein Epitope Signature Tag (PrEST) library allows SILAC-based absolute quantification and multiplexed determination of protein copy numbers in cell lines. *Mol. Cell. Proteomics* 11, 0111.009613 (2012).
28. Clair, G. et al. Spatially-resolved proteomics: rapid quantitative analysis of laser capture microdissected alveolar tissue samples. *Sci. Rep.* 6, 39223 (2016).
29. Pisania, A. et al. Quantitative analysis of cell composition and purity of human pancreatic islet preparations. *Lab. Investig.* 90, 1661-1675 (2010). [[SUPPORTING #7]]
30. Rodriguez-calvo, T. et al. Heterogeneity and lobularity of pancreatic pathology in type 1 diabetes during the prediabetic phase. *J. Histochem. Cytochem.* 63, 626-636 (2015).
31. Richardson, S. J. et al. Islet cell hyperexpression of HLA class I antigens: a defining feature in type 1 diabetes. *Diabetologia* 59, 2448-2458 (2016).
32. Rowe, P. A., Campbell-Thompson, M. L., Schatz, D. A. & Atkinson, M. A. The pancreas in human type 1 diabetes. *Semin. Immunopathol.* 33, 29-43 (2011).
33. White, A. K. et al. High-throughput microfluidic single-cell RT-qPCR. *Proc. Natl. Acad. Sci. U.S.A* 108, 13999-14004 (2011).
34. Zhu, Y. & Fang, Q. Integrated droplet analysis system with electrospray ionization-mass spectrometry using a hydrophilic tongue-based droplet extraction interface. *Anal. Chem.* 82, 8361-8366 (2010).
35. Zhu, Y. et al. Printing 2-dimentional droplet array for single-cell reverse transcription quantitative per assay with a microfluidic robot. *Sci. Rep.* 5, 9551 (2015).
36. Zhu, Y. et al. Nanoliter-scale protein crystallization and screening with a microfluidic droplet robot. *Sci. Rep.* 4, 5046 (2014).
37. Schneider, C. a, Rasband, W. S. & Eliceiri, K. W. NIH Image to ImageJ: 25 years of image analysis. *Nat. Methods* 9, 671-675 (2012).
38. Yu, Y. Q., Gilar, M., Lee, P. J., Bouvier, E. S. P. & Gebler, J. C. Enzyme-friendly, mass spectrometry-compatible surfactant for in-solution enzymatic digestion of proteins. *Anal. Chem.* 75, 6023-6028 (2003).
39. Tyanova, S. et al. The Perseus computational platform for comprehensive analysis of (prote)omics data. *Nat. Methods* 13, 731-740 (2016).
40. Spitzer, M., Wildenhain, J., Rappsilber, J. & Tyers, M. BoxPlotR: a web tool for generation of box plots. *Nat. Methods* 11, 121-2 (2014).

What is claimed is:

1. A method of proteome analysis comprising the steps of:
obtaining a biological sample, wherein the biological sample is an animal tissue sample, animal biopsy, animal cell homogenate, animal cell fraction, cultured animal cells, non-cultured animal cells, animal whole blood, animal plasma, animal biological fluids, or a single cell organism;
transferring a first volume of the biological sample to a platform, wherein the platform comprises a substrate comprising at least one reactor vessel having one or more hydrophilic surfaces configured for containment of a biological sample, wherein the hydrophilic surfaces have a non-zero total surface area less than 25 mm$^2$, a spacer plate containing a spacer plate aperture, wherein the spacer plate aperture is dimensioned to surround the at least one reactor vessel when the spacer plate is positioned on the substrate, a cover positioned on the spacer plate, and a membrane interposed between the spacer plate and the cover and containing a membrane aperture that is dimensioned to surround the at least one reactor vessel when the membrane is positioned on the spacer plate, wherein the substrate, spacer plate and cover are each formed from a material that is transparent to optical light and wherein transferring the first volume of the biological sample comprises transferring the first volume of the biological sample to the at least one reactor vessel, wherein the first volume is a non-zero amount less than 1000 nL;
processing the biological sample in the at least one reactor vessel;
extracting from the at least one reactor vessel a processed sample comprising less than 500 ng of a complement of proteins, peptides related to the complement of proteins, or both;

dispensing the processed sample into one well on a well plate having a plurality of wells, wherein the one well is pre-loaded with a volume of a liquid carrier buffer and the volume of the processed sample that is transferred into one well on the well plate is a non-zero amount that is less than 50 µL;

diluting the processed sample, thereby yielding in the one well a diluted sample, wherein the diluted sample has a volume of at least 5 µL, and the diluting comprises dispensing a volume of a wash solution into the at least one reactor vessel and subsequently transferring the at least one reactor vessel's contents to the one well;

transferring the diluted sample from the one well to a mass-spectrometry-based analytical instrument; and providing protein identification for each of a plurality of proteins composing the complement of proteins.

2. The method of claim 1, wherein the complement of proteins, peptides related to the complement of proteins, or both are unlabeled.

3. The method of claim 1, further comprising the step of co-registering a spatial region of a tissue sample with a reactor vessel, and with a well.

4. The method of claim 3, wherein the spatial region has dimensions less than or equal to 500 µm.

5. The method of claim 3, wherein the spatial region has dimensions less than or equal to 100 µm.

6. The method of claim 1, wherein the liquid carrier buffer comprises a mass spectrometry-compatible surfactant.

7. The method of claim 6, wherein the MS-compatible surfactant comprises ProteaseMAX, RapiGest, PPS Silent Surfactant, oxtyl β-D-glucopyranoside, n-dodecyl β-D-maltoside (DDM), digitonin, Span 80, Span 20, sodium deoxycholate, or a combination thereof.

8. The method of claim 1, wherein the plurality of proteins comprises at least 1000 proteins.

9. The method of claim 1, wherein the plurality of proteins comprises at least 2000 proteins.

10. The method of claim 1, further comprising generating a visual representation of the protein identifications.

11. The method of claim 10, wherein the visual representation comprises one or more of the protein identifications mapped to a spatial region of a tissue sample.

12. The method of claim 11, wherein the visual representation further comprises a quantification of protein amount for the one or more protein identifications.

13. The method of claim 1, further comprising repeating said steps of dispensing a volume of a wash solution and said transferring the at least one reactor vessel's contents at least once.

14. The method of claim 1, wherein said transferring the diluted sample from the one well to a mass-spectrometry-based analytical instrument comprises contacting the well plate with a notched tip of a syringe, extracting the diluted sample from the one well into the syringe, and dispensing into the mass-spectrometry-based analytical instrument via the syringe.

15. The method of claim 1, wherein the biological sample is less than 100 nL.

16. The method of claim 1, wherein the liquid carrier buffer is phosphate-buffered saline, ammonium bicarbonate, tris(hydroxymethyl)aminomethane, liquid chromatography mobile phase, or a combination thereof.

17. The method of claim 7, wherein the liquid carrier buffer is phosphate-buffered saline, ammonium bicarbonate, tris(hydroxymethyl)aminomethane, liquid chromatography mobile phase, or a combination thereof.

18. The method of claim 1, wherein the volume of the liquid carrier buffer is a non-zero amount that is less than 50 µL.

19. The method of claim 1, wherein the biological sample is less than 100 nL, and the volume of the liquid carrier buffer is a non-zero amount that is less than 50 µL.

20. A method of proteome analysis comprising:

obtaining a biological sample, wherein the biological sample is an animal tissue sample, animal biopsy, animal cell homogenate, animal cell fraction, cultured animal cells, non-cultured animal cells, animal whole blood, animal plasma, animal biological fluids or a single cell organism;

transferring a first volume of the biological sample to a platform, wherein the platform comprises a substrate comprising at least one reactor vessel having one or more hydrophilic surfaces configured for containment of a biological sample, wherein the hydrophilic surfaces have a non-zero total surface area less than 25 $mm^2$, a spacer plate containing a spacer plate aperture, wherein the spacer plate aperture is dimensioned to surround the at least one reactor vessel when the spacer plate is positioned on the substrate, a cover positioned on the spacer plate, and a membrane interposed between the spacer plate and the cover and containing a membrane aperture that is dimensioned to surround the at least one reactor vessel when the membrane is positioned on the spacer plate, wherein the substrate, spacer plate and cover are each formed from a material that is transparent to optical light and wherein transferring the first volume of the biological sample comprises transferring the first volume of the biological sample to the at least one reactor vessel, wherein the first volume is a non-zero amount less than 1000 nL;

processing the biological sample in the at least one reactor vessel;

extracting from the at least one reactor vessel a processed sample comprising less than 500 ng of a complement of proteins, peptides related to the complement of proteins, or both;

dispensing the processed sample into one well on a well plate having a plurality of wells and the volume of the processed sample that is transferred into one well on the well plate is a non-zero amount that is less than 50 µL;

dispensing a volume of a wash solution into the at least one reactor vessel and subsequently transferring the at least one reactor vessel's contents to the one well on the well plate, thereby yielding in the one well a diluted sample, wherein the diluted sample has a volume of at least 5 µL;

transferring the diluted sample from the one well to a mass-spectrometry-based analytical instrument; and providing protein identification for each of a plurality of proteins composing the complement of proteins.

21. The method of claim 20, further comprising obtaining a biological sample, transferring a first volume of the biological sample to the at least one reactor vessel, wherein the first volume is a non-zero amount less than 1000 nL, and processing the biological sample to obtain the processed sample.

22. The method of claim 21, wherein the biological sample is a tissue sample, and the method further comprises co-registering a spatial region of the tissue sample with the one reactor, and with the one well.

23. The method of claim 22, wherein the spatial region has dimensions less than or equal to 500 µm.

24. The method of claim 1, wherein transferring the diluted sample from the one well to a mass-spectrometry-based analytical instrument comprises transferring the diluted sample via a syringe to an autosampler associated with the mass-spectrometry-based analytical instrument.

25. The method of claim 20, wherein transferring the diluted sample from the one well to a mass-spectrometry-based analytical instrument comprises transferring the diluted sample via a syringe to an autosampler associated with the mass-spectrometry-based analytical instrument.

26. The method of claim 1, wherein the biological sample is a mammalian sample.

27. The method of claim 20, wherein the biological sample is a mammalian sample.

28. The method of claim 1, wherein the biological sample is of primate origin.

29. The method of claim 20, wherein the biological sample is of primate origin.

30. The method of claim 1, wherein the biological sample is a human sample.

31. The method of claim 1, wherein the biological sample is a human sample.

32. The method of claim 1, wherein the biological sample is obtained from a subject that is at risk of, or has acquired, a particular condition or disease.

33. The method of claim 20, wherein the biological sample is obtained from a subject that is at risk of, or has acquired, a particular condition or disease.

34. The method of claim 1, wherein the biological sample is cells isolated from whole blood or cell isolated from histological thin sections.

35. The method of claim 20, wherein the biological sample is cells isolated from whole blood or cell isolated from histological thin sections.

36. The method of claim 1, wherein the biological sample is an animal tissue sample, and obtaining the animal tissue sample comprises laser-capture microdissection.

37. The method of claim 20, wherein the biological sample is an animal tissue sample, and obtaining the animal tissue sample comprises laser-capture microdissection.

38. The method of claim 1, wherein the substrate comprises a plurality of reactor vessels, and the spacer plate aperture and the membrane aperture are each dimensioned to surround the plurality of reactor vessels.

39. The method of claim 20, wherein the substrate comprises a plurality of reactor vessels, and the spacer plate aperture and the membrane aperture are each dimensioned to surround the plurality of reactor vessels.

* * * * *